US008367727B2

(12) United States Patent
Bassaganya-Riera et al.

(10) Patent No.: US 8,367,727 B2
(45) Date of Patent: *Feb. 5, 2013

(54) METHOD OF USING ABSCISIC ACID TO TREAT DISEASES AND DISORDERS

(75) Inventors: Josep Bassaganya-Riera, Blacksburg, VA (US); Amir Guri, Blacksburg, VA (US); Raquel Hontecillas, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 216 days.

This patent is subject to a terminal disclaimer.

(21) Appl. No.: 12/712,899

(22) Filed: Feb. 25, 2010

(65) Prior Publication Data

US 2010/0216883 A1 Aug. 26, 2010

Related U.S. Application Data

(63) Continuation-in-part of application No. 11/672,223, filed on Feb. 7, 2007, now Pat. No. 7,741,367.

(60) Provisional application No. 60/771,033, filed on Feb. 8, 2006, provisional application No. 60/821,720, filed on Aug. 8, 2006.

(51) Int. Cl.
*A61K 31/19* (2006.01)
(52) U.S. Cl. ..................................................... 514/557
(58) Field of Classification Search .................. 514/557, 514/560
See application file for complete search history.

(56) References Cited

U.S. PATENT DOCUMENTS

| 3,958,025 | A | 5/1976 | Livingston |
| 7,741,367 | B2 * | 6/2010 | Bassaganya-Riera et al. ............................ 514/557 |
| 2004/0052922 | A1 | 3/2004 | Pistolesi |
| 2004/0216194 | A1 | 10/2004 | Hauptmann et al. |
| 2005/0260181 | A1 | 11/2005 | Girsh |

FOREIGN PATENT DOCUMENTS

| GB | EP0240257 | 10/1987 |
| JP | 03169811 A | 7/1991 |
| WO | 02052955 A1 | 7/2002 |

OTHER PUBLICATIONS

Tanaka, et al., "Therapeutic potential of thiazolidinediones in activation of peroxisome proliferator-activated receptor g for monocyte recruitment and endothelial regeneration", European Journal of Pharmacology, 2005, pp. 255-265.
Tsuchida, et al., "Peroxisome Proliferator-Activated Receptor (PPAR) a Activation Increases Adiponectin Receptors and Reduces Obesity-Related Inflamation in Adipose Tissue Comparison of Activation of PPARa, PPARg, and Their Combination", Diabetes, vol. 54, Dec. 2005, pp. 3358-3370.

He, et al., "Adipose-specific peroxisome proliferator-activated receptor g knockout causes insulin resistance in fat and liver but not in muscle.", PNAS, vol. 100, No. 26, Dec. 23, 2003, pp. 15712-15717.
Hanauer, et al., "Inflammatory Bowel Disease: Epidemiology, Pathogenesis, and Therapeutic Opportunities", Inflamm Bowel Dis, vol. 12, Supplement 1, Jan. 2006, pp. 3-9.
Hanauer, et al., "The State of the Art in the Management of Inflammatory Bowel Disease", Reviews in Gastroenterological Disorders, vol. 3, No. 3, 2003, pp. 81-92.
Mackner, et al., "Review: Psychosocial Issues in Pediatric Inflammatory Bowel Disease", Journal of Pediatric Psychology, 2004, pp. 243-257.
Odegaard, et al., "Macrophage-specific PPAR gamma controls alternative activation and improves insulin resistance", Nature Publishing Group, vol. 447, Jun. 28, 2007, pp. 1116-1121.
Guri, et al., "Loss of PPAR gamma in immune cells impairs the ability of abscisic acid to improve insulin sensitivity by suppressing monocyte chemoattractant protein-1 expression and macrophage infiltration into white adipose tissue", Journal of Nutritional Biochemistry, 2008 pp. 216-228.
Guri, et al., "Abscisic acid ameliorates atherosclerosis by suppressing macrophage and CD4 T cell recruitment into the aortic wall", Journal of Nutritional Biochemistry, 2010, pp. 1-9.
Bruzzone, et al., "Abscisic Acid Is an Endogenous Stimulator of Insulin Release from Human Pancreatic Islets with Cyclic ADP Ribose as Second Messenger", Journal of Biological Chemistry, vol. 283, No. 47, Nov. 21, 2008, pp. 32188-32197.
Watanabe, et al., "Regulation of PPAR gamma transcriptional activity in 3T3-L1 adipocytes", Biochemical and Biophysical Research Communications, 2003, vol. 300, pp. 429-436.
Magnone, et al., "Abscisic Acid Release by Human Moncytes Activates Monocytes and Vascular Smooth Muscle Cell Response Involved in Atherogenesis", The Journal of Biological Chemistry, vol. 284, No. 26, Jun. 26, 2009, pp. 17808-17818.
Marder, et al., "The Impact of Costimulatory Molecule Gene Polymorphisms on Clinical Outcomes in Liver Transplantation", American Journal of Transplantation, 2003, pp. 424-431.
Garg, et al., "Matrix metalloproteinase-9-mediated tissue injury overrides the protective effect of matrix metalloproteinase-2 during colitis", American Journal of Physiological Gastrointestinal Liver Physiology, 2009, pp. 175-184.
Bassaganya-Riera et al., "PPAR gamma is highly expressed in F4/80hi adipose tissue macrophages and dampens adipose-tissue inflammation", Cellular Immunology, 2009, pp. 138-146.
Soedamah-Muthu et al., "Soluble vascular cell adhesion molecule-1 and soluble E-selectin are associated with micro- and macrovascular complications in Type 1 diabetic patients", Journal of Diabetes and Its Complications, 2006, pp. 188-195.

(Continued)

*Primary Examiner* — Kevin E Weddington
(74) *Attorney, Agent, or Firm* — Blank Rome LLP

(57) ABSTRACT

Methods and compositions for treating inflammatory bowel disease, gastrointestinal inflammation and maintaining normal gut health are described. These methods of the invention involve the administration of abscisic acid in amounts sufficient to alter the expression or activity of PPAR gamma in a cell. Also described are methods for suppressing the expression of cellular adhesion molecules in the gut and methods for increasing CTLA-4 expression on CD4+ T cells through administration of abscisic acid.

8 Claims, 26 Drawing Sheets

OTHER PUBLICATIONS

Klimiuk, et al., "Effect of etanercept on serum levels of soluble cell adhesion molecules (sICAM-1, sVCAM-1, and sE-selectin) and vascular endothelial growth factor in patients with rheumatoid arthritis", Scandinavian Journal of Rheumatology, 2009, pp. 439-444.

Nowak, et al., "Blood serum levels of vascular cell adhesion molecule (sVCAM-1), intercellular adhesion molecule (sICAM-1) and endothelial leucocyte adhesion molecule-1 (ELAM-1) in diabetic retinopathy", Clinical Exp Med, 2008, pp. 159-164.

Douroudis, et al., "Association of CTLA4 but not ICOS polymorphisms with type 1 diabetes in two populations with different disease rates", Human Immunology, 2009, pp. 536-539.

Sakthivel, et al., "Bench to Bedside of CTLA-4: A Novel Immuno-Therapeutic Agent for Inflammatory Disorders", Recent Patents on Inflammation & Drug Discovery, 2009, pp. 84-95.

Song, et al., "Increased Expression of Intercellular Adhesion Molecule-1 and Vascular Cell Adhesion Molecule-1 in Rat Cardiac Allografts", Transplantation Proceedings, 2008, pp. 2720-2723.

Kamoun, Malek, "Cellular and molecular parameters in human renal allograft rejection", Clinical Biochemistry, 2001, pp. 29-34.

Dedrick, et al., "Adhesion molecules as therapeutic target for autoimmune diseases and transplant rejection", Vaccines and Antibodies, 2003, pp. 85-95.

Tapirdamaz O, "The Influence of CTLA-4 Gene Polymorphisms on Liver Transplant Outcomes", Liver Transplantation, 2006, pp. 1552-1556.

Lintig, et al., "Towards a better understanding of carotenoid metabolism in animals", Biochimica et Biophysica Acta, 2005, pp. 122-131.

Guri, et al., "Dietary abscisic acid ameliorates glucose tolerance and obesity-related inflammation in db/db mice fed high-fat diets" Clinical Nutrition, Churchill Livingstone, London, GB vol. 26 No. 1, Feb. 2007, pp. 107-116.

Guri, et al., "Loss of PPAR gamma in immune cells impairs the ability of abscisic acid to improve insulin sensitivity by suppressing monocyte chemoattractant protein-1 expression and macrophage infiltration into white adipose tissue" Journal of Nutritional Biochemistry, Butterworth Publishers, Stoneham, GB bol. 19, No. 4 Mar. 1, 2008, pp. 216-228.

Lehrke, M. and M.A. Lazar, "The Many Faces of PPAR gamma", Cell 123 pp. 993-999, Dec. 16, 2005.

Nesto, R.W. et al., "Thiazolidiniedione Use, Fluid Retention, and Congestive Heart Failure", Diabetes Care 27(1) pp. 256-263, Jan. 2004.

Author Unknown, "National Diabetes Fact Sheet," 2005, 10 pp., U.S. Department of Health and Human Services, Centers for Disease Control and Prevention, Atlanta, GA, USA.

Narayan, et al., "Lifetime risk for diabetes mellitus in the United States," JAMA, 2003, pp. 1884-1890, vol. 290, No. 14, American Medical Association, Chicago, IL, USA.

Lehmann, et al., "An antidiabetic thiazolidinedione is a high affinity ligand for peroxisome proliferator-activated receptor gamma (PPAR gamma)," Journal of Biological Chemistry, 1995, pp. 12953-12956, vol. 270, No. 2, The American Society for Biochemistry and Molecular Biology, Inc., Bethesda, MD, USA.

Braissant, et al., "Differential expression of peroxisome proliferator-activated receptors (PPAR s): tissue distribution of PPAR-alpha, -beta, and -gamma in the adult rat," Endocrinology, 1996, pp. 354-366, vol. 137, No. 1, The Endocrine Society, Chevy Chase, MD, USA.

Chawla, et al., Peroxisome proliferator-activated receptor (PPAR) gamma: adipose-predominant expression and induction early in adipocyte differentiation. Endocrinology, 1994, pp. 798-800, vol. 135, No. 2, The Endocrine Society, Chevy Chase, MD, USA.

McKenna, et al., "Combinatorial control of gene expression by nuclear receptors and coregulators," Cell, 2002, pp. 465-474, vol. 108, Elsevier, Maryland Heights, MO, USA. Ltd., Maryland Heights, MO, USA.

Bassaganya-Riera, et al., "Peroxisome Proliferator-Activated Receptors: the Nutritionally Controlled Molecular Networks that Integrate Inflammation, Immunity and Metabolism," Current Nutrition & Food Science, 2005, pp. 179-187, vol. 1, Bentham Science Publishers Ltd., Oak Park, IL, USA.

Olefsky, "Treatment of insulin resistance with peroxisome proliferator-activated receptor gamma agonists," Journal of Clinical Investigation, 2000, pp. 467-472, vol. 106, No. 4, Ann Arbor, Michigan, USA.

Bogacka, et al., "The effect of pioglitazone on peroxisome proliferator-activated receptor-gamma target genes related to lipid storage in vivo," Diabetes Care, 2004, pp. 1660-1667, vol. 27, No. 7, The American Diabetes Association, Alexandria, VA, USA.

Rajala, et al., "Minireview: The adipocyte—at the crossroads of energy homeostasis, inflammation, and atherosclerosis," Endocrinology, 2003, pp. 3765-3773, vol. 144, No. 9, The Endocrine Society, Chevy Chase, MD, USA.

Trayhurn, "Endocrine and signalling role of adipose tissue: new perspectives on fat," Acta Physiologica Scandinavica, 2005, pp. 285-293, vol. 184, Scandinavian Physiological Society, Stockholm, Sweden.

Yamauchi T. et al. "Adiponectin stimulates glucose utilization and fatty-acid oxidation by activating AMP-activated protein kinase", Nature Medicine vol. 8 pp. 1288-1295, 2002.

Arner P. "Regional adiposity in man." Journal of Endocrinology, vol. 155: pp. 191-192; 1997.

Luo Y, et al., Cytotoxic T lymphocyte antigen-4 promoter -658CT gene polymorphism is associated with ulcerative colitis in Chinese patients. Int J Colorectal Dis 2009;24:489-93.

Kuryliszyn-Moskal A, Klimiuk PA, "Serum soluble adhesion molecules—sICAM-1, sVCAM-1, sE-selectin—in patients with systemic rheumatoid arthritis", Pol Merkur Lekarski 2004; vol. 17 pp. 353-356.

Ogden, et al., "Prevalence of Overweight and Obesity in the United States, 199-2004", Apr. 5 ,2006, Journal of the American Medical Association, vol. 295, No. 13, pp. 1549-1555.

Pi--Sunyer, et al., "Clinical Guidelines on the Identification, Evaluation, and Treatment of Overweight and Obesity in Adults", National Institute of Health-National Heart, Lung and Blood Institute, Publication No. 98-4083 1998, pp. 1-228.

Walczak, et al., "PPARadigms and PPARadoxes: expanding roles for PPAR gamma in the control of lipid metabolism", Journal of Lipid Research, vol. 43, 2002, pp. 177-186.

Kang, et al., "Adipocyte-Derived Th2 Cytokines and Myeloid PPAR delta Regulate Macrophage Polarization and Insulin Sensitivity", Cell Metabolism vol. 7, 2008, pp. 485-495.

Hersoug, et al., "The link between the epidemics of obesity and allergic diseases: does obesity induce decreased immune tolerance?", Allergy, 2007, pp. 1205-1213.

Bassaganya-Riera, et al., "F4/80hiCCR2hi macrophage infiltration into the intra-abdominal fat worsens the severity of experimental IBD in obese mice with DSS colitis", The European E-Journal of Clinical Nutrition and Metabolism vol. 4, 2009, pp. 90-97.

Yamauchi, et al., "Adiponectin stimulates glucose utilitization and fatty-acid oxidation by activating AMP-activated protein kinase" Natural Medicine, vol. 8, No. 11 Nov. 2002; pp. 1288-1295.

Zick, "Insulin resistance: a phosphorylation-based uncoupling of insulin signaling", Trends in Cell Biology, vol. 11, No. 11 Nov. 2001; pp. 437-441.

Weisberg, et al. "Obesity is associated with macrophage accumulation in adipose tissue", The Journal of Clinical Investigation, vol. 112, No. 12, Dec. 2003; pp. 1796-1808.

Xu, et al., "Chronic inflammation in fat plays a crucial role in the development of obesity-related insulin resistance", The Journal of Clinical Investigation, vol. 112, No. 12, Dec. 2003, pp. 1821-1830.

De Souza et al., "Effects of Pioglitazone on Adipose Tissue Remodeling Within the Setting of Obesity and Insulin Resistance", Diabetes, vol. 50, Aug. 2001, pp. 1863-1871.

Nesto, et al., "Thiazolidinedione Use, Fluid Retention, and Congestive Heart Failure a Consensus Statement from the American Heart Association and American Diabetes Association", Circulation, 2003, pp. 2941-2948.

Yamauchi, et al., "The molecular mechanisms by which PPAR gamma/RXR inhibitors improve insulin resistance", Nippon Rinsho, Nov. 2001, pp. 2245-2254.

Wysowski, et al., "Rapid Increase in the Use of Oral Andtidiabetic Drugs in the United States, 1990-2001", Diabetes Care, vol. 26, No. 6, Jun. 2003, pp. 1852-1855.

Lin, et al., "Abscisic acid regulation of heterophylly in *Marsilea quadrifolia* L.: effects of R-(-) and S-(+) isomers", Journal of Experimental Botany, vol. 56, No. 421, pp. 2935-2948.

Yin, et al., "Reduced Early Alcohol-Induced Liver Injury in CD14-Deficient Mice", The American Association of Immunologists, 2001, pp. 4737-4742.

Hontecillas, et al., "Nutritional Regulation of Porcine Colitis by Conjugated Linoleic Acid", American Society for Nutritional Sciences, 2002, pp. 2019-2027.

Bassaganya-Riera, et al., "Conjugated Linoleic Acid Ameliorates Viral Infectivity in a Pig Model of Virally Induced Immunosuppression", American Society for Nutritional Sciences, 2003, pp. 3204-3214.

Guan, et al., "Thiazolidinediones expand body fluid volume through PPAR gamma stimulation of ENaC -mediated renal salt absorption", Nature Medicine, vol. 11, No. 8, Aug. 2005; pp. 861-866.

Desvergne, et al., "Peroxisome Proliferator-Activated Receptors: Nuclear Control of Metabolism", Endocrine Reviews, 1999; pp. 649-688.

Nagy, et al., "Oxidized LDL Regulates Macrophage Gene Expression through Ligand Activation of PPAR gamma", Cell, vol. 93, Apr. 17, 1998, pp. 229-240.

McIntyre, et al., "Identification of an intracellular receptor for lysophosphatidic acid (LPA): LPA is a transcellular PPAR gamma agonist", PNAS, vol. 100, No. 1, Jan. 7, 2003; pp. 131-136.

Ouchi, et al., "Adiponectin, an Adipocyte-Derived Plasma Protein, Inhibits Endothelial NF-kB signalling through a cAMP-Dependent Pathway", Circulation, 2000, pp. 1296-1301.

Berg, et al., "The adipocyte-secreted protein Acrp30 enhances hepatic insulin action", Nature Medicine, vol. 7, No. 8, Aug. 2001, pp. 947-953.

Fruebis, et al., "Proteolytic cleavage product of 30-kDa adipocyte complement-related protein increases fatty acid oxidation in muscle and causes weight loss in mice", PNAS, vol. 98, No. 4, Feb. 13, 2001, pp. 2005-2010.

Trayhurn, et al., "Adipokines: inflammation and the pleiotropic role of white adipose tissue", British Journal of Nutrition, 2004, pp. 347-355.

Mudaliar, et al., "Thiazolidinediones, peripheral edema, and Type 2 diabetes: incidence, pathopysiology, and clinical implications", Endocrine Practice, vol. 9, No. 5, Sep./Oct. 2003, pp. 406-416.

Page II et al., "Possible Heart Failure Exacerbation Associated with Rosiglitazone: Case Report and Literature Review", Pharmacotherapy, 2003, pp. 945-954.

Tai, et al., "Activation of the Nuclear Receptor Peroxisome Proliferator-activated Receptor g Promotes Brown Adipocyte Differentiation", The Journal of Biological Chemistry, vol. 271, No. 47, Aug. 27, 1996; pp. 29909-29914.

Watkins, et al., "Lipid metabolome-wide effects of the PPAR gamma agonist rosiglitazone", Journal of Lipid Research, vol. 43, 2002, pp. 1809-1817.

Xu, et al., "The fat-derived hormone adiponectin alleviates alcoholic and nonalcoholic fatty liver diseases in mice", The Journal of Clinical Investigation, vol. 112, No. 1, Jul. 2003, pp. 91-100.

Gomez-Cadenas et al., "Leaf Abscission Induced by Ethylene in Water -Stressed Intact Seedlings of Cleopatra Mandarin Requires Previous Abscisic Acid Accumulation in Roots", Plant Physiology, 1996, pp. 401-408.

Gubler, et al., "Dormancy release, ABA and pre-harvest sprouting", Current Opinion in Plant Biology, 2005, pp. 183-187.

Goliber, et al., "Osmotic stress, endogenous abscisic acid and the control of leaf morphology in *Hippuris vulgaris* L. ", Cell and Environment, 1989, pp. 163-171.

Finkelstein, et al., "ABA and sugar interactions regulating development: cross-talk or voices in a crowd?", Current Opinion in Plant Biology, 2001, pp. 26-32.

Arenas-Huertero, et al., "Analysis of *Arabidopsis* glucose insensitive mutants, gin5 and gin6 reveals a cetral role of the plant hormone ABA in the regulation of plant vegetative development by sugar", Genes and Development, 2000, pp. 2085-2096.

Hir, et al., Variations in sucrose and ABA concentrations are concomitant with heteroblastic leaf shape changes in a rhythmically growing species (*Quercus robur*), Tree Physiology, 2005, pp. 229-238.

Hill, et al., "Abscisic Acid Structure-Activity Relationships in Barley Aleurone Layers and Protoplasts", Plant Physiology, 1995, pp. 573-579.

Loveys, et al., "Improved Extraction of Abscisic Acid from Plant Tissue", Aust. J. Plant Physiology, 1998, pp. 421-427.

Zhou, et al., "A New Abscisic Acid Catabolic Pathway", Plant Physiology, Jan. 2004, vol. 134, pp. 361-369, pp. 361-369.

Guri, et al., "Dietary abscisic acid ameliorates glucose tolerance and obesity-related inflammation in db/db mice fed high-fat diets", Clinical Nutrition, 2007 pp. 107-116.

Akiyama, et al., "Conditional Disruption of the Peroxisome Proliferator-Activated Receptor g Gene in Mice Results in Lowered Expression of ABCA1, ABCG1, and apoE in Macrophages and Reduced Cholesterol Efflux", Molecular and Cellular Biology, Apr. 2002, pp. 2607-2619.

Bassaganya-Riera et al., "Activation of PPAR gamma and delta by Conjugated Linoleic Acid Mediates Protection From Experimental Inflammatory Bowel Disease", Gastroenterology, 2004, pp. 777-791.

Kutlu, et al., Molecular Regulation of Monocyte Chemoattractant Protein-1 Expression in Pancreatic b-Cells, Diabetes, vol. 52, Feb. 2003, pp. 348-355.

Weisberg, et al., "CCR2 modulates inflammatory and metabolic effects of high-fat feeding", The Journal of Clinical Investigation, vol. 116, No. 1, Jan. 2006, pp. 115-124.

Kanda, et al., "MCP-1 contributes to macrophage infiltration into adipose tissue, insulin resistance, and hepatic steatosis in obesity", The Journal of Clinical Investigation, vol. 116, No. 6, Jun. 2006, pp. 1494-1505.

Kamei, et al., "Overexpression of Monocyte Chemoattractant Protein-1 in Adipose Tissues Causes Macrophage Recruitment and Insulin Resistance", Journal of Biological Chemistry, vol. 281, No. 36, Sep. 8, 2006, pp. 26602-26614.

Mokdad, et al., "The Continuing Epidemics of Obesity and Diabetes in the United States", JAMA, vol. 286, No. 10, Sep. 12, 2001, pp. 1195-1200.

Holness, et al., "Investigation of potential mechanisms regulating protein expression of hepatic pyruvate dehydrogenase kinase isoforms 2 and 4 by fatty acids and thyroid hormone," Biochemical Journal, 2003, pp. 687-695.

Boden, et al., "Fatty Acid-induced Inflammation and Insulin Resistance in Skeletal Muscle and Liver", Current Diabetes Reports, 2006, pp. 177-181.

Shoelson, et al., "Inflammation and insulin resistance", The Journal of Clinical Investigation, vol. 116, No. 7, Jul. 2006, pp. 1793-1801.

Lin, et al., "The macrophage F4/80 receptor is required for the induction of antigen-specific efferent regulatory T cells in peripheral tolerance", The Journal of Experimental Medicine, May 16, 2005, pp. 1615-1625.

Charriere, et al., "Preadipocyte Conversion to Macrophage Evidence of Plasticity", The Journal of Biological Chemistry, vol. 278, No. 11, Mar. 14, 2003, pp. 9850-9855.

Nibbering, et al., "Quantitative Immunocytochemical Characterization of Mononuclear Phagocytes", Cellular Immunology, 1987, pp. 374-385.

Phillips, et al., "Differential signaling mechanisms regulate expression of CC chemokine receptor-2 during monocyte maturation", Journal of Inflammation, 2005, pp. 1-14.

Chen, et al., "The mouse CCR2 gene is regulated by two promoters that are responsive to plasma cholesterol and peroxisome proliferator-activated receptor g ligands", Biochemical and Biophysical Research Communications, 2005. pp. 188-193.

Suzuki, et al., "Alteration in Expression Profiles of a Series of Diabetes-Related Genes in db/db Mice Following Treatment with Thiazolidinediones", Japanese Journal of Pharmacology vol. 84, 2000, pp. 113-123.

Bouhlel, et al., "PPAR gamma Activation Primes Human Monocytes into Alternative M2 Macrophages with Anti-inflammatory Properties", Cell Metabolism, vol. 6, pp. 137-143.

Dietz, et al., "Health Consequences of Obesity in Youth: Childhood Predictors of Adult Disease", Pediatrics, vol. 101; pp. 518-525.
Hotamisligil, et al., "Role of Endoplasmic Reticulum Stress and c-Jun NH2-Terminal Kinase Pathways in Inflammation and Origin of Obesity and Diabetes", Diabetes, vol. 54, Supplement 2, Dec. 2005, pp. 73-78.
Tuncman, et al., "Functional in vivo interactions between JNK1 and JNK2 isoforms in obesity and insulin resistance", PNAS, 2006, vol. 103, No. 28, pp. 10741-10746.
Yuan, et al., "Reversal of Obesity and Diet Induced Insulin Resistance with Salicylates or Targeted Disruption of Iota Kappa /kappa Beta", 2001 vol. 293, pp. 1673-1678.
Arkan, et al., "Iotta Kappa Kappa-Beta links inflammation to obesity-induced insulin resistance", Nature Medicine, 2005, vol. 11, No. 2, pp. 191-198.
Davis, et al., "Tlr-4 Deficiency Selectively Protects Against Obesity Induced by Diets High in Saturated Fat", Obesity Journal, 2008 vol. 16, No. 6, pp. 1248-1255.
Yamauchi, et al., "The Mechanism by Which Both Heterozygous Peroxisome Proliferator-activated Receptor gamma (PPAR) Deficiency and PPAR gamma Agonist Improve Insulin Resistance", Journal of Biological Chemistry, vol. 276, No. 44 pp. 41245-41254.
Bays, et al., "Pathogenic Potential of Adipose Tissue and Metabolic Consequences of Adipocyte Hypertropy and increased Visceral Adiposity", Expert Review of Cardiovascular Therapy, 2008, vol. 6, No. 3, pp. 343-368.
Pascual, et al., "A Sumoylation-Dependent Pathway Mediating Transrepression of Inflammatory Response Genes by PPAR Gamma", Nature, 2005, vol. 437, pp. 759-763.
Jennewein, et al., "Sumoylation of PPAR Gamma by Apoptic Cells Prevens LPS-Induced NCoR removal from Kappa B Binding Site Mediating Transrepression of Pro-Inflammatory Cytokines", Journal of Immunology, 2008, vol. 181, pp. 5646-5652.
Blanquicett, et al., "Thiazolidinediones as Anti-Cancer Agents", Cancer Therapy, 2008, vol. 6, pp. 25-34.
Mestre, et al., "A Cannabinoid Agonist Interferes with the Progression of a Chronic Model of Multiple Sclerosis by Downregulating Adhesion Molecules", Molecular and Cellular Neuroscience, vol. 40, 2009, pp. 258-266.
Serghides, et al., "Peroxisome Proliferator-Activated Receptor {{Gamma}}-Retinoid X REceptor Agonists Increase CD36-Dependent Phagocytosis of Plasmodium Falciparum-Parasitized Erythrocytes and Decrease Malaria-Induced TNF-{{alpha}} Secretion by Monocytes/Macrophages", Journal of Immunology, 2001, vol. 166, pp. 6742-6748.
Barna, et al., Depressed Peroxisome Proliferator-activated Receptor Gamma (PPAR Gamma) is Indicative of Severe Pulmonary Sarcoidosis: Possible Involvement of Interferon Gamma (IFN-Gamma), Sarcoidosis Vasculitis and Diffuse Lung Diseases, 2006, vol. 23, pp. 93-100.
Serhan, et al., "Novel Anti-Inflammatory Targets for Asthma A Role for PPAR Gamma?", American Journal of Respiratory Cell Molecular Biology, 2001, vol. 24, p. 658-661.
Diab, et al., "Peroxisome Proliferator-Activated Receptor-{Gamma} Agonist 15-Deoxy-{Delta} 12, 1412, 14-Prostagla ndin J2 Ameliorates Experimental Autoimmune Encephalomyelitis", Journal of Immunology, 2002, vol. 168 pp. 2508-2515.
Diab, et al., "Ligands for the Peroxisome Proliferator-Activated Receptor-Gamma and the Retinoid X Receptor Exert Additive Anti-Inflammatory Effects on Experimental Autoimmune Encephalomyelitis", Journal of Neuroimmunology, vol. 148, 2004, pp. 116-126.
Raikwar, et al., "PPAR Gamma Antagonists Exacerbate Neural Antigen-Specific Th1 Response and Experimental Allergic Encephalomyelitis", Journal of Neuroimmunology, vol. 167, 2005, pp. 99-107.
Storer, et al., "Peroxisome Proliferator-Activated Receptor Gamma Agonists Inhibit the Activation of Microglia and Astrocytes: Implications for Multiple Sclerosis", Journal of Neuroimmunology, vol. 161, 2005, pp. 113-122.
Hontecillas, et al., "Peroxisome Proliferator-Activated Receptor {Gamma} is Required for Regulatory CD4+T Cell-Mediated Protection against Colitis", Journal of Neuroimmunology, vol. 178, 2007, pp. 2940-2949.
Ramakers, et al., "The PPAR Gamma Agonist Rosiglitazone Impairs Colonic Inflammation in Mice with Experimental Colitis", Journal of Clinical Immunology, 2007, vol. 27, No. 3, pp. 275-283.
Lewis, et al., "An Open-Label Trial of the PPAR Gamma Ligand Rosiglitazone for Active Ulcerative Colitis", The American Journal of Gastroenterology, 2001, vol. 96, No. 12.
Kobayashi, et al., "Pioglitazone, a Peroxisome Proliferator-Activated Receptor Gamma Agonist, Reduces the Progression of Experimental Osteoarthritis in Guinea Pigs", Arthritis and Rheumatism, 2005, vol. 52, No. 2 pp. 479-487.
Man M-Q, et al., "Topical Treatment with Thiazolidinediones, Activators of Peroxisome Proliferator-Activated Receptor-Gamma, Normalizes Epidermal Homeostasis in a Murine Hyperproliferative Disease Model", Experimental Dermatology, 2006, vol. 15, pp. 154-160.
Bolzano, et al., "Biguanides: Reasons for Withdrawal of Drugs and Remaining Indications", Acta Medica Austriaca AMA, 1978, vol. 5 pp. 85-88.
D'Uscio, et al., "Mechanism of Endothelial Dysfunction in Apolipoprotein E-Deficient Mice", Arteriosclerosis Thrombosis Vascular Biology, 2001, pp. 1017-1022.
Holst, et al., "Treatment of Type 2 Diabetes Mellitus with Agonists of the GLP-1 Receptor or DPP-IV Inhibitors", Expert Opinion on Emerging Drugs, 2004, vol. 9, pp. 155-166.
Drucker, et al., "Glucagon-like Peptide I Stimulates Insulin Gene Expression and Increases Cyclic AMP Levels in a Rat Islet Cell Line", Proceedings of the National Academy of the Sciences, 1987, vol. 84, pp. 3434-3438.
Klett, et al., "Angiotensin II Stimulates the Synthesis of Angiotensinogen in Hepatocytes by Inhibiting Adenylylcyclase Activity and Stabilizing Angiotensinogen mRNA", The Journal of Biological Chemistry, 1993, vol. 268, No. 33 pp. 25095-25107.
Krumenacker, et al., "Differential Expression of Genes Involved in cGMP-dependent Nitric Oxide Signaling in Murine Embryonic Stem (ES) Cells and ES Cell-Derived Cardiomyocytes", Nitric Oxide, 2006, vol. 14, pp. 1-11.
Murad, et al., "Nitric Oxide and Cyclic GMP in Cell Signaling and Drug Development", The New England Journal of Medicine, 2006, vol. 355, pp. 2003-2011.
Hanefeld, et al., "Anti-Inflammatory Effects of Pioglitazone and/or Simvastatin in High Cardiovascular Risk Patients with Elevated High Sensitivity C-Reactive Protein: The PIOSTAT Study", Journal of the American College of Cardiology, 2007, vol. 49, pp. 290-297.
Martin, et al., "Statin-Induced Inhibition of the Rho-Signaling Pathway Activates PPAR Omega and Induces HDL apoA-I", Journal of Clinical Investigation, 2001, vol. 107, pp. 1423-1432.
Ye, et al., "Activation of Peroxisome Proliferator-Activated Receptor-Gamma (PPAR-Gamma) by Atorvastatin is Mediated by 15-Deoxy-Delta-12, 14-PGJ2", Prostaglandins & other Lipid Mediators, 2007, vol. 84, pp. 43-53.
Ahuja, et al., "Differential Effects of Rexinoids and Thiazolidinediones on Metabolic Gene Expression in Diabetic Rodents", Molecular Pharmacology, 2001, vol. 59, pp. 765-773.
Altucci, et al., "Rexinoid-Triggered Differentiation and Tumor-Selective Apoptosis of Acute Myeloid Leukemia by Protein Kinase A-Mediated Desubordination of Retinoid X Receptor", Cancer Research, 2005, vol. 65, No. 19, pp. 8754-8765.
Dragnev, et al., "Nonclassical Retinoids and Lung Carcinogenesis", Clinical Lung Cancer, 2005, pp. 237-244.
Finkelstein, et al., "Annual Medical Spending Attributable to ObesityL Payer and Service-Specific Estimates", Health Affairs, 2009, vol. 28, No. 5 pp. 822-831.
Marcy, et al., "Second-Generation Thiazolidinediones and Hepatotoxicity", The Annals of Pharmacotherapy, 2004, vol. 38, pp. 1419-1423.

* cited by examiner

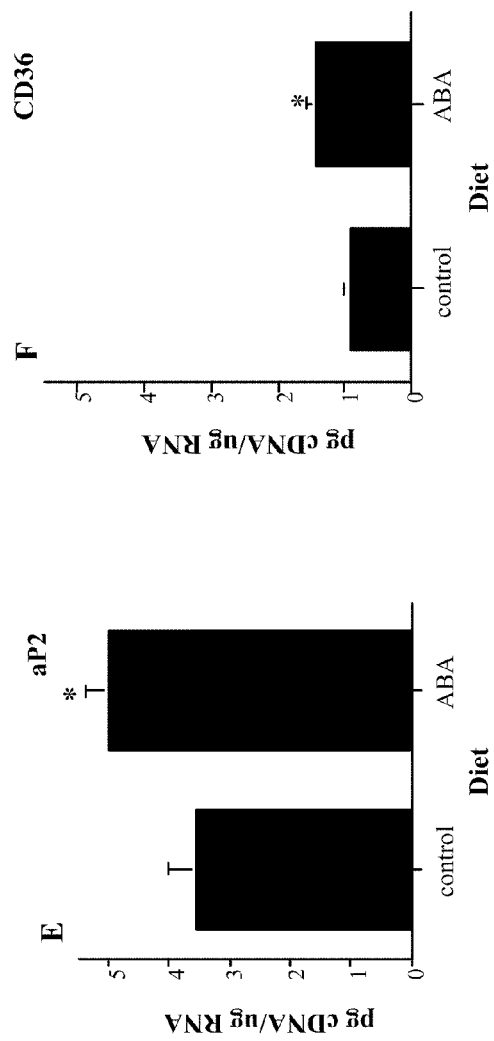

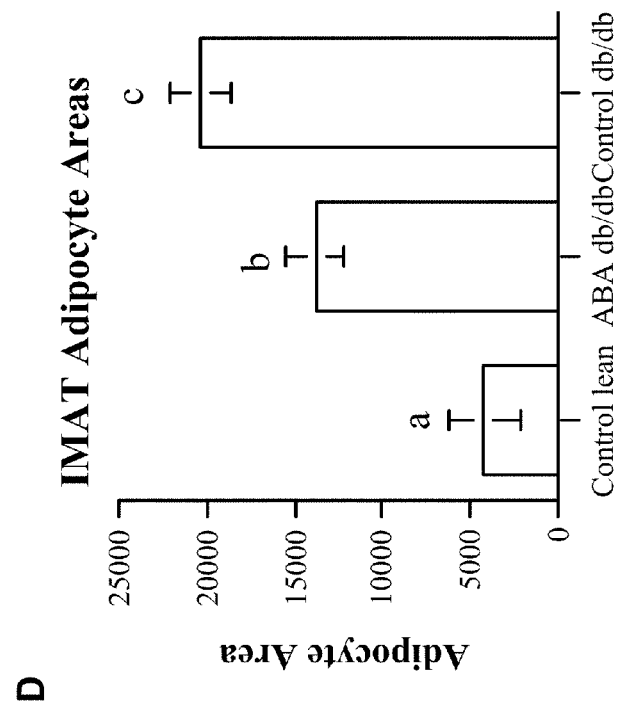
Figure 8, cont.

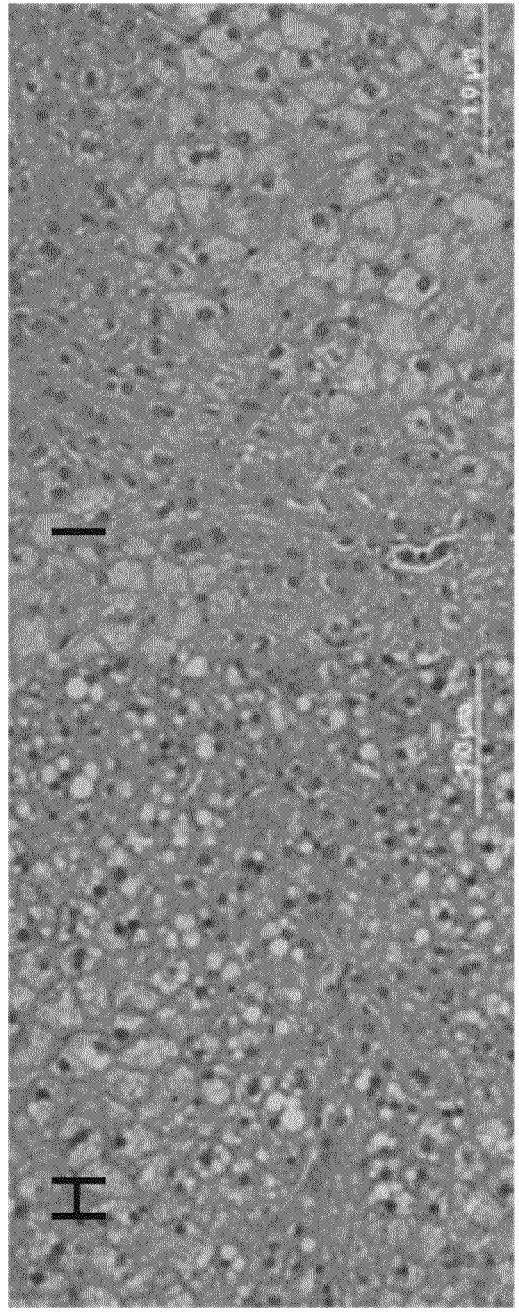
Figure 12, cont.

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: Synthetic primer

<400> SEQUENCE: 1
tggggatgaa gagggctgag                                                 20

<210> SEQ ID NO 2
<211> LENGTH: 19
<212> TYPE: DNA
<213> ORGANISM: Artificial sequence
<220> FEATURE:
<223> OTHER INFORMATION: Synthetic primer

<400> SEQUENCE: 2
ggggactgcc gttgtctgt                                                  19

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
acagtgacct ggcgctcttc                                                 20

<210> SEQ ID NO 4
<211> LENGTH: 20
<212> TYPE: DNA
<213> ORGANISM: Artificial sequence
<220> FEATURE:
<223> OTHER INFORMATION: synthetic primer

<400> SEQUENCE: 4
tggtgtcctg gatggcttct                                                 20

<210> SEQ ID NO 5
<211> LENGTH: 20
<212> TYPE: DNA
<213> ORGANISM: Artificial sequence
<220> FEATURE:
<223> OTHER INFORMATION: synthetic primer

<400> SEQUENCE: 5
caggcttgct gaacgtgaag                                                 20

<210> SEQ ID NO 6
<211> LENGTH: 18
<212> TYPE: DNA
<213> ORGANISM: Artificial sequence
<220> FEATURE:
<223> OTHER INFORMATION: synthetic primer
```

```
<400> SEQUENCE: 6
ggagcacctt ggcgaaca                                              18

<210> SEQ ID NO 7
<211> LENGTH: 19
<212> TYPE: DNA
<213> ORGANISM: Artificial sequence
<220> FEATURE:
<223> OTHER INFORMATION: synthetic primer

<400> SEQUENCE: 7
ccgggccacg tagaaaaca                                             19

<210> SEQ ID NO 8
<211> LENGTH: 20
<212> TYPE: DNA
<213> ORGANISM: Artificial sequence
<220> FEATURE:
<223> OTHER INFORMATION: synthetic primer

<400> SEQUENCE: 8
cctccaaaca cagccaggac                                            20

<210> SEQ ID NO 9
<211> LENGTH: 19
<212> TYPE: DNA
<213> ORGANISM: Artificial sequence
<220> FEATURE:
<223> OTHER INFORMATION: synthetic primer

<400> SEQUENCE: 9
cccaggcatt gctgacagg                                             19

<210> SEQ ID NO 10
<211> LENGTH: 20
<212> TYPE: DNA
<213> ORGANISM: Artificial sequence
<220> FEATURE:
<223> OTHER INFORMATION: synthetic primer

<400> SEQUENCE: 10
tggaaggtgg acagtgaggc                                            20

<210> SEQ ID NO 11
<211> LENGTH: 20
<212> TYPE: DNA
<213> ORGANISM: Artificial sequence
<220> FEATURE:
<223> OTHER INFORMATION: synthetic primer

<400> SEQUENCE: 11
acaaggccgt tctcttcacc                                            20

<210> SEQ ID NO 12
<211> LENGTH: 19
<212> TYPE: DNA
<213> ORGANISM: Artificial sequence
<220> FEATURE:
<223> OTHER INFORMATION: synthetic primer

<400> SEQUENCE: 12
ccccatcccc atacacctg                                             19
```

```
<210> SEQ ID NO 13
<211> LENGTH: 24
<212> TYPE: DNA
<213> ORGANISM: Artificial sequence
<220> FEATURE:
<223> OTHER INFORMATION: synthetic primer

<400> SEQUENCE: 13
tctcttatca aaggctctac ttcc                                          24

<210> SEQ ID NO 14
<211> LENGTH: 21
<212> TYPE: DNA
<213> ORGANISM: Artificial sequence
<220> FEATURE:
<223> OTHER INFORMATION: synthetic primer

<400> SEQUENCE: 14
caaaattcca tccaggcctc t                                             21

<210> SEQ ID NO 15
<211> LENGTH: 20
<212> TYPE: DNA
<213> ORGANISM: Artificial sequence
<220> FEATURE:
<223> OTHER INFORMATION: synthetic primer

<400> SEQUENCE: 15
actgccagaa gaggcactcc                                               20

<210> SEQ ID NO 16
<211> LENGTH: 18
<212> TYPE: DNA
<213> ORGANISM: Artificial sequence
<220> FEATURE:
<223> OTHER INFORMATION: synthetic primer

<400> SEQUENCE: 16
cgatcacccc gaagttca                                                 18

<210> SEQ ID NO 17
<211> LENGTH: 19
<212> TYPE: DNA
<213> ORGANISM: Artificial sequence
<220> FEATURE:
<223> OTHER INFORMATION: synthetic primer

<400> SEQUENCE: 17
cccaggcatt gctgacagg                                                19

<210> SEQ ID NO 18
<211> LENGTH: 20
<212> TYPE: DNA
<213> ORGANISM: Artificial sequence
<220> FEATURE:
<223> OTHER INFORMATION: synthetic primer

<400> SEQUENCE: 18
tggaaggtgg acagtgaggc                                               20

<210> SEQ ID NO 19
<211> LENGTH: 20
<212> TYPE: DNA
<213> ORGANISM: Artificial sequence
<220> FEATURE:
<223> OTHER INFORMATION: synthetic primer
```

-continued

```
<400> SEQUENCE: 19
actgccagaa gaggcactcc                                               20

<210> SEQ ID NO 20
<211> LENGTH: 18
<212> TYPE: DNA
<213> ORGANISM: Artificial sequence
<220> FEATURE:
<223> OTHER INFORMATION: synthetic primer

<400> SEQUENCE: 20
cgatcacccc gaagttca                                                 18

<210> SEQ ID NO 21
<211> LENGTH: 20
<212> TYPE: DNA
<213> ORGANISM: Artificial sequence
<220> FEATURE:
<223> OTHER INFORMATION: synthetic primer

<400> SEQUENCE: 21
cttgcctaat ccacagactg                                               20

<210> SEQ ID NO 22
<211> LENGTH: 18
<212> TYPE: DNA
<213> ORGANISM: Artificial sequence
<220> FEATURE:
<223> OTHER INFORMATION: synthetic primer

<400> SEQUENCE: 22
gcctgaacag caccacta                                                 18
```

METHOD OF USING ABSCISIC ACID TO TREAT DISEASES AND DISORDERS

REFERENCE TO RELATED APPLICATIONS

This application is a continuation-in-part of U.S. patent application Ser. No. 11/672,223, filed Feb. 7, 2007, which in turn claims the benefit of U.S. Provisional Patent Application No. 60/771,033, filed Feb. 8, 2006, and U.S. provisional patent application No. 60/821,720, filed Aug. 8, 2006. The entire disclosures of each of these applications are incorporated herein by reference.

FIELD OF THE INVENTION

The present invention relates to the field of medical treatments for diseases and disorders. More specifically, the present invention relates to the use of a therapeutically or prophylactically effective amount of abscisic acid to prevent and treat inflammatory bowel diseases and disorders associated with increased T cell activation and immune cell infiltration.

BACKGROUND OF THE DISCLOSURE

In spite of efforts by public health officials to encourage physical activity and reduce energy intake, the obesity rate in the U.S. and worldwide has continued to climb and it has reached epidemic proportions. According to estimates by the Center for Disease Control and Prevention in the year 2000, 30% of Americans are obese and 65% are overweight (1). One of the manifestations associated with this obesity epidemic is the growing number of people diagnosed with Non-Insulin Dependent Diabetes Mellitus (NIDDM). NIDDM is a widespread and debilitating disease characterized by insulin resistance and inflammation that can lead to coronary heart disease, hypertension, blindness, neuropathy, nephropathy, and limb amputations (2). It was recently estimated that 20.8 million Americans had NIDDM and 40.1% of middle-aged adults had prediabetes, a condition characterized by either impaired glucose tolerance or high blood fasting glucose concentrations (2). Future predictions indicate that 1 of 3 children born in 2000 will one day become diabetic (3). The impending consequence is that millions of people, if not already, will soon become dependent on oral antidiabetic medications to maintain their quality of life.

One of the most effective of the currently available medications is the thiazolidinedione (TZD) class of insulin-sensitizing drugs. Subsequent to their use as oral antidiabetic agents it was discovered that TZDs function by binding to peroxisome proliferator-activated receptor gamma (PPAR γ) (4), a nuclear receptor expressed highly in immune cells, intestine, and adipose tissue (5). The nuclear receptor superfamily, which includes the vitamin D receptor (VDR), retinoid X receptor (RXR), PPAR α, and PPAR δ, consists of 48 ligand-induced transcription factors that respond to steroid and thyroid hormones, vitamins, lipid metabolites, and xenobiotics (6, 7). After binding of a synthetic or natural agonist, PPAR γ forms a heterodimer with RXR and undergoes a conformational change that allows it to recruit coactivators (8). These coactivators, which include members of the steroid receptor coactivator (SRC) family, assist the PPAR γ RXR complex in binding to specific PPAR response elements (PPREs) in the promoter regions by increasing histone acetylation, thereby altering chromatin structure and making it more accessible (8). A primary outcome of the PPAR-controlled transcriptional regulation of genes is a reduction in the hyperlipidemia, hyperglycemia, and hyperinsulinemia associated with insulin resistance (9), though the extent to which each tissue contributes to this response is still unclear.

While PPAR γ is expressed in a number of different organs that contribute to glucose homeostasis, including skeletal muscle, pancreas, and liver, white adipose tissue (WAT) is believed to represent the primary site of TZD action (10μ, 11). Adipose tissue is an extremely bioactive organ that produces a number of hormone-like polypeptides called adipokines, which regulate a wide-range of metabolic, immune and inflammatory processes throughout the body (12). Problems arise, however, when adipocytes become hypertrophic and dysfunctional during the onset of obesity. Obesity promotes the secretion of pro-inflammatory adipokines, such as leptin, plasminogen activator inhibitor 1 (PAI-1), tumor necrosis factor alpha (TNF-α) and interleukin 6 (IL-6), and a suppression in the secretion of adiponectin, an anti-inflammatory and glucose-sensitizing polypeptide (13, 14). The pro-inflammatory adipokines can disrupt insulin signaling by promoting serine phosphorylation of insulin receptor substrate 1 (IRS-1) (15). Obesity is also associated with the infiltration of bone-marrow derived macrophages, which become the key producers of pro-inflammatory mediators in WAT (16). PPAR γ activation by synthetic agonists such as rosiglitazone reduces macrophage infiltration in WAT, a sign of WAT inflammation, and increases the number of smaller, more insulin-sensitive adipocytes in the subcutaneous region (17, 18). Adipokine production is also modulated to favor the production of adiponectin and inhibit the secretion of pro-inflammatory compounds (19).

The side effects of TZDs such as weight gain, hepatotoxicity and congestive heart failure have limited their use by millions of diabetic patients (9, 20). For instance, troglitazone (REZULIN) was launched in 1997 and withdrawn from the market in March of 2000 due to reports of serious liver injury when compared to other TZDs (21), while other Food and Drug Administration (FDA)-approved TZDs for NIDDM treatment, including rosiglitazone (AVANDIA) and pioglitazone (ACTOS), continue to be widely prescribed, concerns regarding their safety persist. In this regard, the FDA recommended that the presence of liver enzymes in blood of diabetic patients taking AVANDIA be periodically monitored. Furthermore, due to the risk factors and side effects connected with TZDs and other oral antidiabetic agents, there are no preventative medications currently available for the millions of people with prediabetes.

Abscisic acid (ABA) increases PPAR γ activity in vitro (5), improves glucose tolerance and ameliorates adipose tissue inflammation in the db/db mouse, a transgenic model of obesity, and in wild-type C57BL6/J mice fed high-fat diets (5, 6). Improvements in glucose tolerance by ABA were shown to be dependent on PPAR γ being expressed in hematopoietic cells (6). The inventors have also previously demonstrated that ABA reduces immune cell infiltration and inflammation in aortas of ApoE-deficient mice (7). In this study the mechanism of ABA was more consistent with an upregulation of the intracellular messenger cAMP (7), and other recent studies have shown that cAMP upregulation is involved in ABA's mechanism of action in mammalian cells (8, 9). In all studies conducted with ABA, there have been no side-effects observed.

While the role of ABA as a phytohormone has been studied extensively, there have been no studies that explore the effect of ABA as a dietary supplement or in treatment of diabetes or inflammation.

U.S. Pat. No. 3,958,025 to Livingston teaches a method of treating a vitamin deficiency of abscisic acid in man, animal, or avian species. The patent does not address the fact that abscisic acid is not considered by those of skill in the art as an essential vitamin, nor its requirement in the diet. In addition, the method disclosed in U.S. Pat. No. 3,958,025 does not teach the use of abscisic acid to treat or prevent diabetes and inflammation, including obesity-related inflammation.

Inflammatory bowel disease (IBD), with its two clinical manifestations Crohn's Disease (CD) and Ulcerative Colitis (UC), is characterized by significant inflammation and immune cell infiltration into the gastrointestinal (GI) tract, resulting in pain and discomfort for those afflicted (66). IBD is often managed by an array of treatments, which traditionally include aminosalicylates, corticosteroids, immunosuppressors, and anti-tumor necrosis factor α (TNF-α) therapy. The type of treatment used depends on the clinical goal (induction or remission-maintenance), the severity of inflammation, the response to current or prior treatment, and the presence of complications (67). Current IBD treatments can carry with them significant side-effects, such as weight gain, cushingoid appearance, osteopenia/osteoporosis, pancreatitis, and systemic immune suppression (68), and there is an overall need for more safe and effective treatments.

Recent clinical trials have shown that synthetic agonists of the nuclear receptor PPAR γ effectively ameliorate IBD. The PPAR γ activating anti-diabetes drugs AVANDIA and ACTOS have been shown to significantly attenuate the inflammatory response of immune cells (69). These synthetic compounds, however, have been associated with cardiovascular complications, and therefore their use for IBD has been contraindicated.

Based on findings that ABA reduces inflammation and has been shown to act through a PPAR γ-dependent mechanism, the inventors wished to assess the efficacy of ABA as a prophylactic or therapeutic option for the treatment of IBD. It was found that ABA significantly ameliorated dextran sodium sulfate (DSS)-induced colitis and reduced colonic inflammation. Two noteworthy observations arose from those findings. First, ABA significantly decreased adhesion cell marker expression in the colon. Second, mice supplemented with ABA showed significantly elevated CTLA-4 expression on CD4+ T cells in whole blood. CTLA-4 is an immunosuppressive protein whose polymorphisms have not only been linked to IBD, but also autoimmune disorders and transplant outcomes (75). Thus, evidence is herein provided that ABA is a promising agent for the treatment or prevention of IBD and may be useful for disorders in which cellular adhesion molecule expression or lymphocyte hyperactivation play pathogenic roles.

SUMMARY OF THE INVENTION

It is an object of the present invention to provide methods for the treating or preventing inflammatory bowel disease in a mammal by administering to the mammal a composition containing abscisic acid (ABA) in amounts sufficient to alter the expression or activity of PPAR γ in a cell of the mammal.

It is a further object of the present invention to provide methods for the treating or preventing gastrointestinal tract inflammation in a mammal by administering to the mammal a composition containing abscisic acid (ABA) in amounts sufficient to altern the expression or activity of PPAR γ in a cell of the mammal.

The compositions of the present invention may further contain a carrier that has substantially no effect on the expression or activity of PPAR γ in a cell of the mammal. The carriers of the present invention may be pharmaceutical carriers, nutritional supplements, functional foods or dietary aids, as are further described below.

It is a still further object of the present invention to provide methods of suppressing expression of cellular adhesion molecules in a cell of a mammal by contacting the cell with ABA in an amount that is sufficient to alter the expression or activity of PPAR γ in the cell. Cellular adhesion molecules for which expression may be suppressed include vascular adhesion molecule 1, mucosal addressin adhesion marker 1 and E-selectin.

It is a yet a further object of the present invention to provide methods of increasing CTLA-4 expression in a T cell of a mammal by contacting the cell with ABA in an amount that is sufficient to alter the expression or activity of PPAR γ in the cell.

BRIEF DESCRIPTION OF THE DRAWINGS

The accompanying drawings, which are incorporated in and constitute a part of this specification, illustrate several embodiments of the invention and together with the written description, serve to explain certain principles and details of embodiments of the invention.

FIG. 3A shows a plot for leptin receptor-deficient (db/db) mice which were fed 0, 100, 200, 400, or 800 mg of a racemic mixture of ABA/kg diet. FIG. 3B shows a plot for Db/db mice which were fed either 0 or 100 mg racemic ABA/kg. Data are presented as least square means±standard error. Data points with an asterisk are significantly different ($P<0.05$).

FIG. 8, Panel D, shows a bar graph of size of adipocytes in intramuscular adipocyte tissue.

Figure 17:
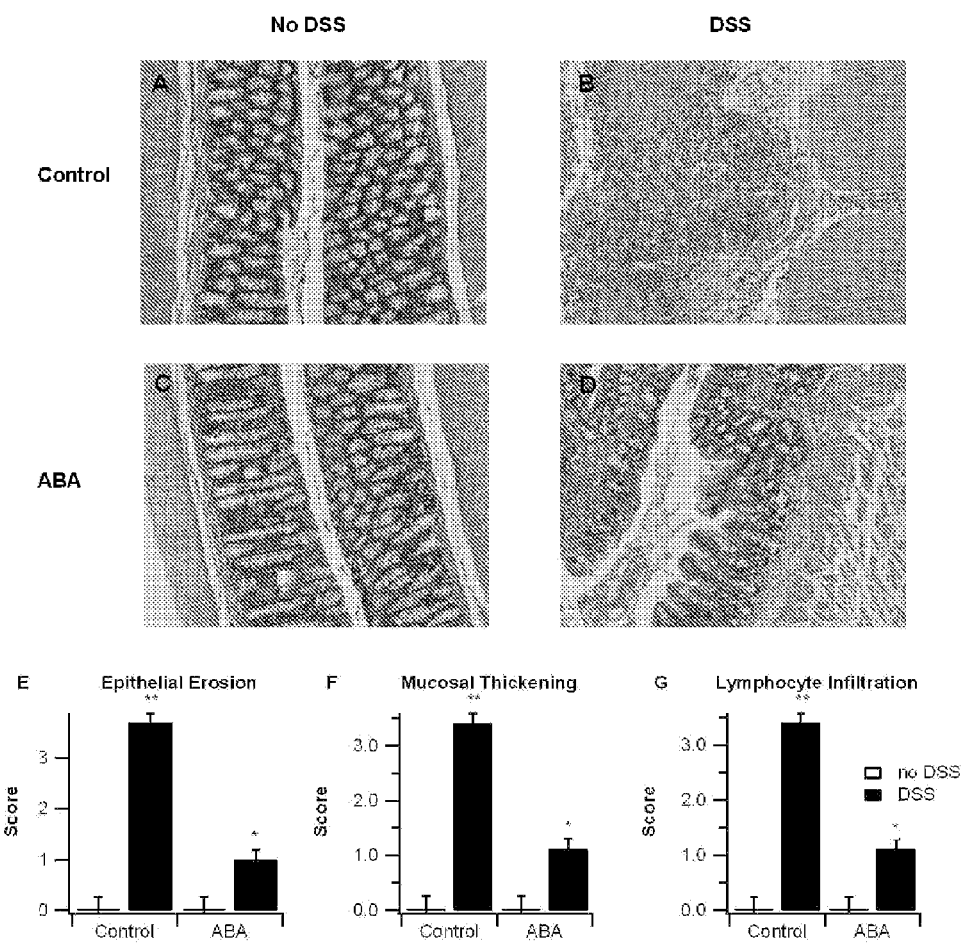

FIG. 17 shows images and graphs demonstrating the effect of dietary abscisic acid (ABA) supplementation on colon histopathology. Representative photomicrographs from control, no-DSS (A), control, DSS (B), ABA, no-DSS(C), and ABA, DSS (D) groups are depicted in this figure. All specimens underwent blinded histological examination and were scored (1-4) on epithelial erosion (E), mucosal wall thickening (F), and leukocyte infiltration (G). Data are represented as mean±standard error. Points with an asterisk are significantly different from control, non-DSS treatment (P<0.05).

Figure 18:
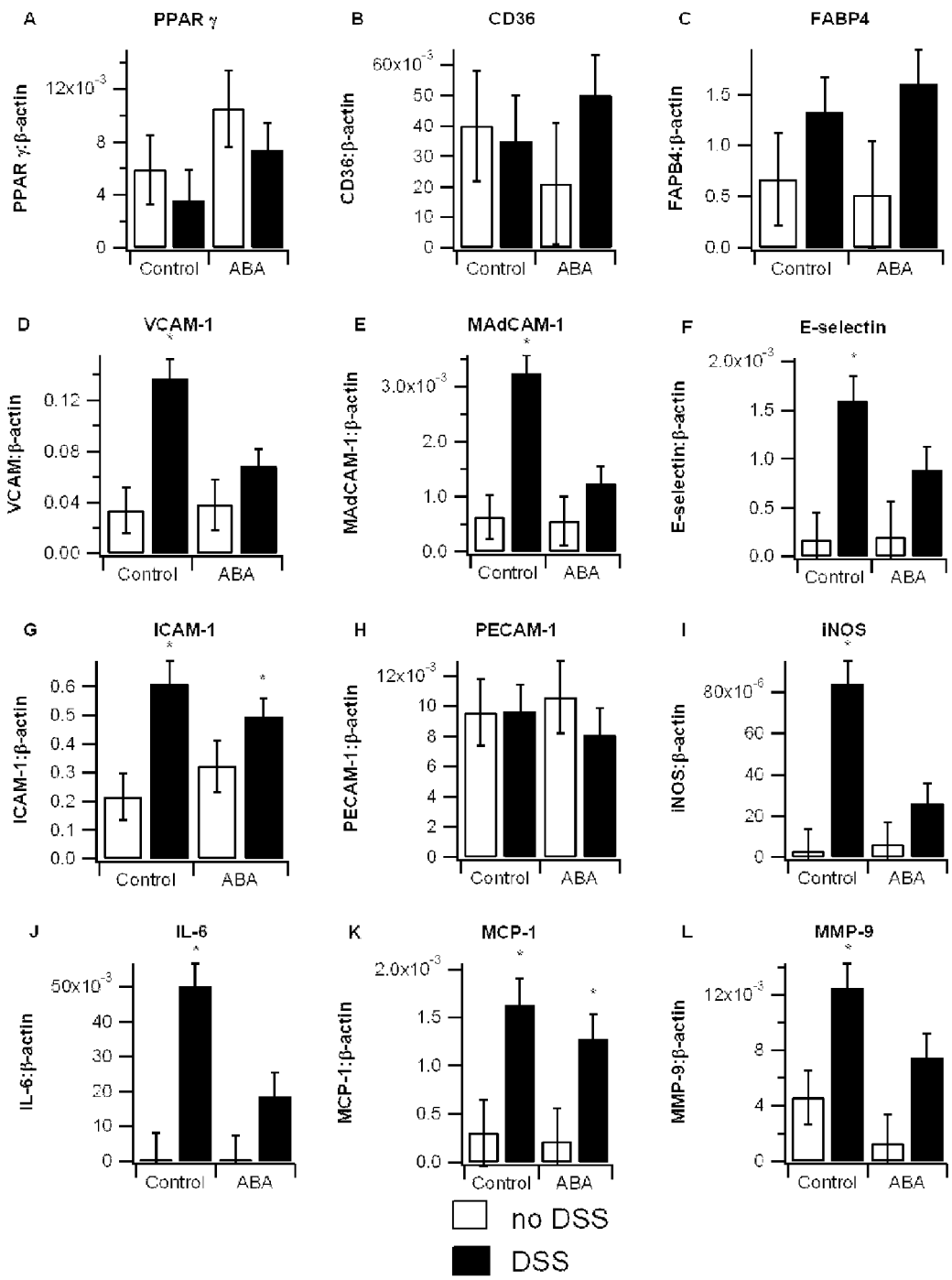

FIG. 18 shows graphs demonstrating the effect of dietary abscisic acid (ABA) supplementation on colon inflammatory gene expression. Expressions of peroxisome proliferator-activated receptor γ (PPAR γ) and PPAR γ-responsive genes CD36, fatty acid binding protein 4 (FABP-4) (A-C), adhesion molecules vascular adhesion molecule 1 (VCAM-1), muscosal vascular addressin cell adhesion molecule 1 (MAdCAM-1), E-selectin, intracellular adhesion molecule 1 (ICAM-1), and platelet/endothelial cell adhesion molecule 1 (PECAM-1) (D-H), and pro-inflammatory proteins interleukin-6 (IL-6), inducible nitric oxide synthase (iNOS), monocyte chemoattractant protein-1 (MCP-1), and matrix metalloproteinase 9 (MMP-9) (1-L) were assessed by real-time quantitative PCR. Data are represented as mean±standard error. Points with an asterisk are significantly different from control, non-DSS treatment (P<0.05).

Figure 19:
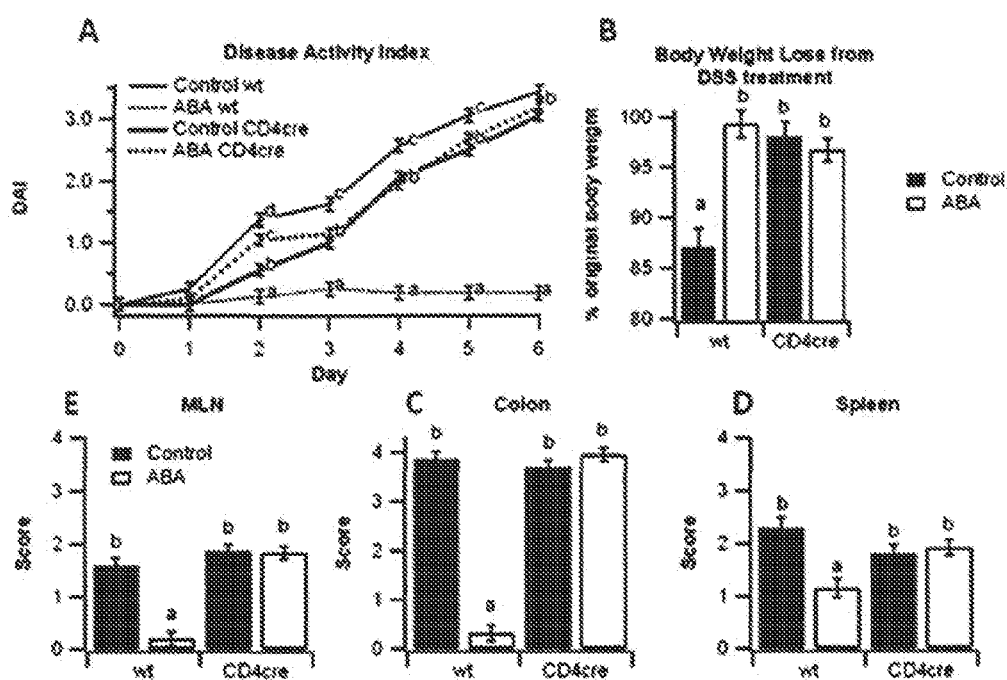

FIG. 19 shows plots and graphs demonstrating the effect of abscisic acid supplementation and tissue-specific PPAR γ-deletion on colitis severity. C57BL6/J (wt) or PPAR γ flfl; CD4 Cre+ (CD4cre) mice, which lack PPAR γ specifically in CD4+ T-cells, were fed diets with or without ABA for 35 days prior to a 7 day challenge with 2.5% dextran sodium sulfate (DSS). The disease activity index (DAI), a composite score reflecting clinical signs of the disease (i.e. perianal soiling, rectal bleeding, diarrhea, and piloerection) was assessed daily (A) and the percent in body weight lost during the DSS-challenge (B) were calculated. On day 7 mice were euthanized and the colon, spleen, and mesenteric lymph nodes (MLN) (C-E) were macroscopically scored for inflammation. Data are represented as mean±standard error. Points with different subscripts are significantly different (P<0.05).

Figure 20:
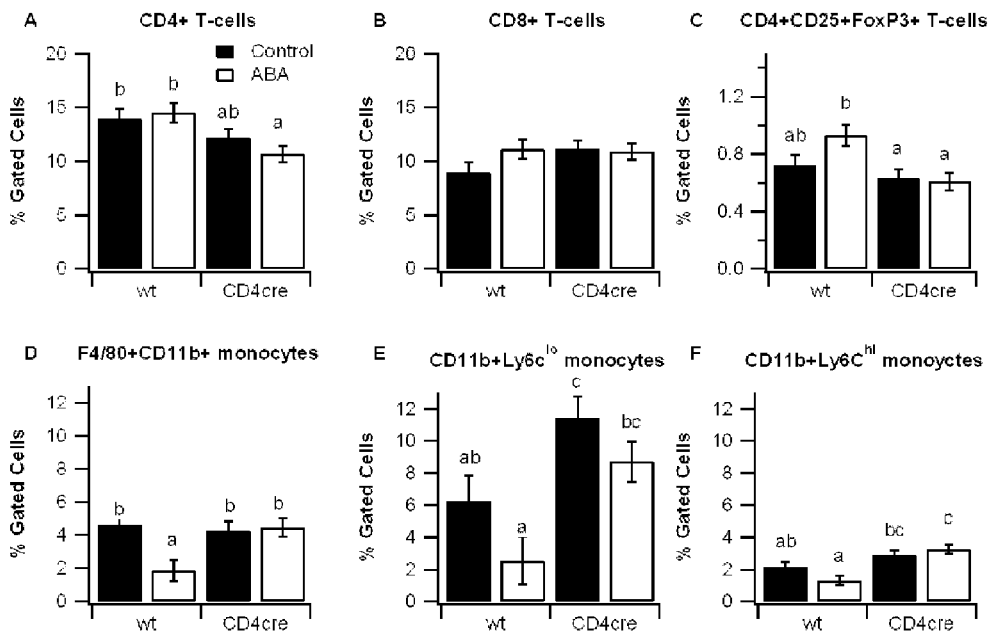
Figure 20:
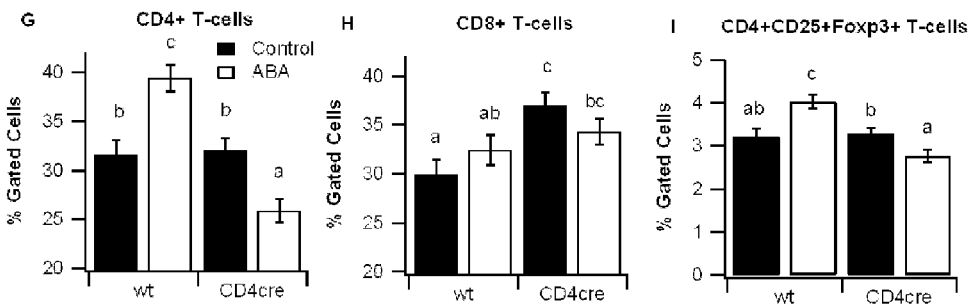

FIG. 20 shows graphs demonstrating the effect of abscisic acid supplementation and tissue-specific PPAR γ-deletion on immune cell populations in blood and mesenteric lymph nodes (MLN). Following the 7-day DSS challenge blood (A-F) and MLN (G-I) from each mouse were immunophenotyped with primary anti-mouse antibodies to analyze lymphocyte and monocyte subsets. Data was compiled with a BD LSR2 flow cytometer and analyzed with FACS Diva software. Data are represented as mean±standard error. Points with different subscripts are significantly different (P<0.05).

Figure 21:
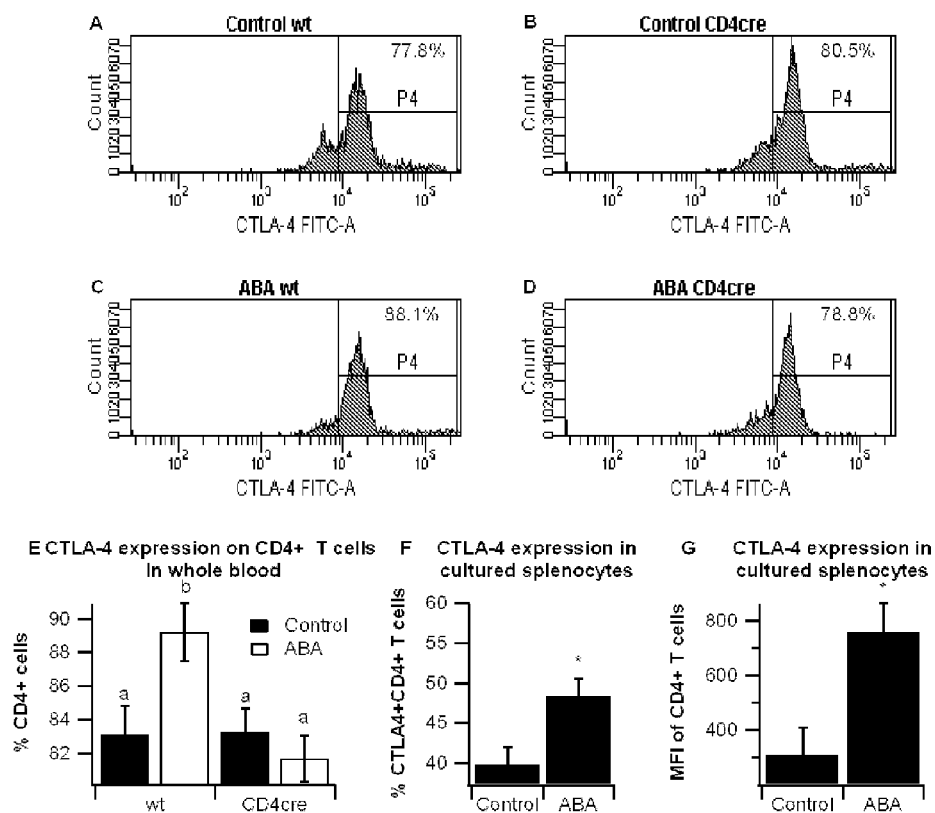

FIG. 21 shows plots and graphs demonstrating the effect of abscisic acid on cytotoxic T-lymphocyte antigen 4 (CTLA-4). C57BL6/J (wt) or PPAR γ flfl; CD4 Cre+ (CD4cre) mice, which lack PPAR γ specifically in CD4+ T-cells, were fed diets with or without ABA for 35 days prior to a 7 day challenge with 2.5% dextran sodium sulfate (DSS). CTLA-4 expression in CD4+ T cells in whole blood was measured by flow cytometry. Representative histograms from Control, wt (A), ABA, wt (B), Control, CD4cre (C), and ABA, CD4cre (D) mice as well as mean CTLA-4 expression (E) are shown. In addition, splenocytes from wt mice were cultured with or without ABA (10 µM) for 20 hrs, and CTLA-4 expression (F) and median fluorescence activity (MFI) (G) on CD4+ T cells were measured by flow cytometry. Data are depicted as mean±standard error. Points with different subscripts or with an asterisk are significantly different (P<0.05).

DETAILED DESCRIPTION OF THE INVENTION

The present invention provides new uses for abscisic acid and structurally related compounds. The term abscisic acid (abbreviated herein as ABA) herein refers to a plant hormone containing a trimethylcyclohexene ring with one or more hydroxy groups (for instance a 6-hydroxy group), a 3-oxo group and an unsaturated side chain in the sixth position of the trimethylcyclohexene ring containing cis-7, trans-9 double bonds, its non-toxic salts, active esters, active isomers, active metabolites, and mixtures thereof. Non-toxic salts include, for example, alkyl esters having from 1 to 6 carbon atoms in the alkyl group, as well as mono-, di- and tri-glycerides, and mixtures thereof. Active isomers of abscisic acid include geometrical isomers and its non-toxic salts, e.g., sodium, potassium, calcium, and magnesium salts, and its active esters, e.g., alkyl esters having from 1 to 6 carbon atoms in the alkyl group, as well as mono-, di- and tri-glycerides, and mixtures thereof. Active optical isomers of abscisic acid include the (+)-enantiomer and the (−)-enantiomer and its non-toxic salts, e.g., sodium, potassium, calcium, and magnesium salts, and its active esters, e.g., alkyl esters having from 1 to 6 carbon atoms in the alkyl group, as well as mono-, di- and tri-glycerides, and mixtures thereof. Active metabolites of abscisic acid include oxygenated abscisic acid analogs, including but not limited to, 8'-hydroxyABA, (+)-7'-hydroxyABA, 2'3'-dihydroABA, 8'-hydroxy-2',3'-dihydroABA and its non-toxic salts, e.g., sodium, potassium, calcium, and magnesium salts, and its active esters, e.g., alkyl esters having from 1 to 6 carbon atoms in the alkyl group, as well as mono-, di- and tri-glycerides, and mixtures thereof. Structurally related compounds, include but are not limited to, compounds containing conjugated double bonds (e.g., conjugated dienes, trienes and tetraenes) in the unsaturated side chain and compounds containing a trimethylcyclohexene ring with or without hydroxy moieties. For ease of reference, all such compounds are referred to herein generally at times as abscisic acid or ABA.

Abscisic acid may be a substantially pure single chemical compound or a mixture of one or more abscisic acid compounds as defined above. For example, the abscisic acid may be in the form of an extract obtainable or obtained from plant extracts, either directly or following one or more steps of purification or it can be chemically synthesized.

Figure 1:
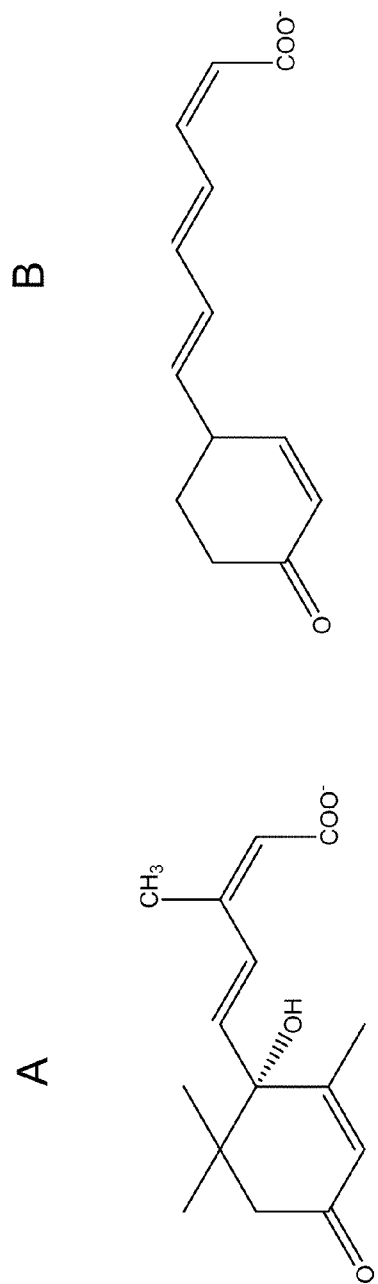
FIG. 1 is a diagram showing the chemical formulas for the general structure for ABA (FIG. 1A) and a structurally related compound (FIG. 1B).

The abscisic acid used in the described methods may be in a free acid form or bound chemically through ester linkages. In its natural form, abscisic acid is heat stable. Abscisic acid may be used in its natural state or in a dried and powdered form. Further, the free acid form of abscisic acid may be converted into a non-toxic salt, such as sodium, potassium or calcium salts, by reacting chemically equivalent amounts of the free acid form with an alkali hydroxide at a basic pH. FIG. 1 depicts ABA and an exemplary compound falling within the definition of abscisic acid and structurally related compounds. Other structurally related compounds are known in the art, such as those disclosed by Hill et al. (45), which is hereby incorporated herein by reference.

In general, the invention provides for use of abscisic acid and structurally related compounds, such as a compound selected from the group consisting abscisic acid, esters thereof, pharmaceutically suitable salts thereof, metabolites thereof, structurally related compounds thereof, or combinations thereof, in the treatment and prevention of diseases and disorders associated with PPAR γ expression and lymphocyte activity. For example, in certain embodiments, the invention relates to prevention and/or treatment of hyperglycemia, impaired glucose tolerance, insulin resistance, prediabetes, and type 2 diabetes. The invention is based, at least in part, on the discovery that abscisic acid can affect the expression of PPAR γ, and that the effects are relevant to all diseases and disorders that involve expression or activity of PPAR γ. As used throughout this document, the term ABA and all of its forms are meant to include the following compounds: abscisic acid, esters thereof, pharmaceutically suitable salts thereof, metabolites thereof, structurally related compounds thereof, analogs thereof, or combinations thereof, as disclosed herein. While not being limited to any particular mode of action, it is possible that abscisic acid and its derivatives and structurally related compounds affect PPAR γ expression and/or activity. However, the invention also contemplates other modes of action, such as by affecting expression or activity of any number of other cellular molecules, including, but not limited to, nuclear receptors that may be activated by ABA, including liver X receptor (LXR), retinoid X receptor (RXR), pregnane X receptor (PXR), vitamin D receptor (VDR), as well as nuclear receptor-independent mechanisms.

In addition, in general, the invention relates to inhibition of infiltration of macrophages into skeletal muscle and white adipose tissue and related inflammation. The inhibition can be found in vitro and in vivo. The effect results from exposing cells to ABA. In embodiments, the invention provides for treating subjects with ABA, for example as a dietary supplement, to reduce skeletal muscle macrophage infiltration, white adipose tissue macrophage infiltration, inflammation, or all three. It also provides for treating a subject to achieve these goals, and additionally to treat a subject suffering from diabetes, to treat a subject at risk for developing diabetes, or to prevent a subject from developing diabetes.

In one aspect, the invention relates to a method of affecting the expression of PPAR γ in a cell. In general, the method comprises contacting a cell with ABA in an amount or concentration sufficient to affect expression or activity of PPAR γ in the cell. For example, it can be exposing a cell for a sufficient amount of time for ABA to enter the cell and have an effect on PPAR γ expression or activity. The method can be practiced either in vitro or in vivo. Where practiced in vitro, the method can be used to study the expression of PPAR γ, to test other compounds for the ability to supplement or antagonize the effects of ABA on PPAR γ expression, or for any other reason of importance to a researcher. When practiced in vivo, the method can be used as a method of treating a subject for one or more diseases or disorders associated with PPAR γ expression. It also may be a method of treating a subject that has a predisposition or likelihood of developing a disease or disorder associated with PPAR γ expression. According to the method of this aspect of the invention, preferably, expression of PPAR γ is increased. The step of contacting a cell can be any action that causes ABA to physically contact one or more target cells. Thus, it can be by way of adding ABA directly to an in vitro culture of cells to be contacted, and allowing the ABA sufficient time to diffuse through the media and contact at least one cell. Likewise, it can be through addition of a dry composition comprising ABA to cells in an aqueous environment. Alternatively, it can be by way of administering ABA to a subject via any acceptable administration route, and allowing the body of the subject to distribute the ABA to the target cell through natural processes. Thus, the in vivo methods can be methods of localized or systemic delivery of ABA to a cell in animals, including all mammals and humans in particular. According to this aspect, ABA and its related compounds can be used to treat a subject therapeutically or prophylactically, and to prepare a composition for use in treating.

In another aspect, the invention provides a method of treating a subject suffering from or at risk of suffering from a disease or disorder involving PPAR γ expression. In general, the method comprises administering ABA or a composition comprising ABA to a subject in need thereof, in an amount sufficient to affect the amount or activity of PPAR γ in at least one cell of the subject. In embodiments, the ABA affects the expression of the PPAR γ gene, resulting in a change in PPAR γ mRNA levels in a cell. In embodiments, the ABA affects the amount of PPAR γ protein in a cell, preferably through increase in expression of the PPAR γ gene. In certain embodiments, the ABA affects the activity of the PPAR γ protein in a cell, preferably by increasing the amount of ABA in the cell. In preferred embodiments, PPAR γ mRNA expression, PPAR γ-responsive gene expression, such as CD36, AP2 (fatty acid binding protein 4) and adiponectin, protein levels, and/or protein activity is increased in a cell of the treated subject. In general, the method comprises administering a sufficient amount for a sufficient time to see a change in PPAR γ expression or activity. Often, the amount administered and the amount of time is adequate to see a change in one or more clinical symptoms of a disease or disorder, or to stop progression of a disease or disorder from reaching a stage where one or more clinical symptoms are seen. According to this aspect, ABA and its related compounds can be used to treat a subject therapeutically or prophylactically, and to prepare a composition for use in treating.

In another aspect, the invention provides a method of treating a subject suffering from or at risk of suffering from a disease or disorder involving dysregulation of skeletal muscle macrophages and/or inflammation of skeletal muscles. In general, the method comprises administering ABA or a composition comprising ABA to a subject in need thereof, in an amount sufficient to reduce or eliminate skeletal muscle inflammation due to production of pro-inflammatory cytokines. According to this aspect, ABA and its related compounds can be used to treat a subject therapeutically or prophylactically, and to prepare a composition for use in treating.

In the methods of treating, administering ABA can be through any known and acceptable route. Such routes include, but are not necessarily limited to, oral, via a mucosal membrane (e.g., nasally, via inhalation, rectally, intrauterely or intravaginally, sublingually), intravenously (e.g., intravenous bolus injection, intravenous infusion), intraperitoneally, and subcutaneously. Administering can likewise be by direct injection to a site (e.g., organ, tissue) containing a target cell (i.e., a cell to be treated). Furthermore, administering can follow any number of regimens. It thus can comprise a single dose or dosing of ABA, or multiple doses or dosings over a period of time. Accordingly, treatment can comprise repeating the administering step one or more times until a desired result is achieved. In embodiments, treating can continue for extended periods of time, such as weeks, months, or years. Those of skill in the art are fully capable of easily developing suitable dosing regimens for individuals based on known parameters in the art. The methods thus contemplate controlling, but not necessarily eliminating, the disease or disorder.

The amount to be administered will vary depending on the subject, stage of disease or disorder, age of the subject, general health of the subject, and various other parameters known and routinely taken into consideration by those of skill in the medical arts. As a general matter, a sufficient amount of ABA will be administered in order to make a detectable change in the amount or activity of PPAR γ protein or mRNA in at least one cell of the subject to whom the ABA is administered. Suitable amounts are disclosed herein, and additional suitable amounts can be identified by those of skill in the art without undue or excessive experimentation, based on the amounts disclosed herein.

The ABA will be administered in a form that is acceptable, tolerable, and effective for the subject. Numerous pharmaceutical forms and formulations for biologically active agents are known in the art, and any and all of these are contemplated by the present invention. Thus, for example, the ABA can be formulated in an oral solution, a caplet, a capsule, an injectable, an infusible, a suppository, a lozenge, a tablet, a cream or salve, an inhalant, and the like.

In one aspect, the invention provides a method of treating or preventing a subject suffering from diabetes, or otherwise healthy individuals at risk for developing diabetes. According to the invention, the term "a subject suffering from diabetes" is used to mean a subject (e.g., animal, human) having a disease or disorder showing one or more clinical signs that are typical of diabetes. The term "a subject at risk for developing diabetes" is used to mean a subject in which one or more clinical signs of diabetes are not clearly shown, but who shows one or more sub-clinical signs that are typical of diabetes, or who has a family history that indicates a significant risk of developing diabetes, or who suffers from obesity or is overweight. In general, the method of treating or preventing according to this aspect of the invention comprises administering to the subject an amount of ABA that is effective in treating or preventing one or more symptoms or clinical manifestations of diabetes, or in preventing development of such symptom(s) or manifestation(s).

Thus, according to the methods of the invention, the invention can provide methods of treatment of diabetes. The methods of treatment can be prophylactic methods. In embodiments, the method is a method of treating type 2 diabetes (T2D). In embodiments, the method is a method of preventing diabetes, such as type 2 diabetes. In embodiments, the method is a method of halting the progression of diabetes, such as type 2 diabetes. In yet other embodiments, the method is a method of improving the health status of a subject suffering from diabetes, such as type 2 diabetes. Accordingly, in embodiments, the invention provides a method of protecting the health, organs, and/or tissues of a subject suffering from diabetes or at risk for developing diabetes.

In one exemplary embodiment of the invention, the method of treating diabetes comprises treating diabetes without causing significant weight gain in the subject being treated. That is, it has been found that the method of treating according to the present invention, which provides the treatment effect, at least in part, by affecting the expression and/or activation of PPAR γ in some cells, provides the beneficial effect without causing a significant gain in weight, for example by fluid retention, in the subject being treated, as compared to other similar subjects not receiving the treatment. While not wishing to be bound by any particular theory as to why this effect is seen, it is likely that treatment with ABA, while causing an increase in PPAR γ expression in some cells, does not cause over-expression or over-activation, as is commonly seen with some other (e.g., synthetic) PPAR γ agonists currently known for treatment of diseases associated with PPAR γ.

In view of the above-mentioned molecular basis for at least part of the effect seen, the present invention provides a method of treating diabetes by increasing the expression of PPAR γ in at least one cell of the subject being treated. As with other methods of the invention, the method comprises administering ABA to a subject suffering from diabetes, where the ABA is administered in an amount sufficient to increase the expression, activity, or amount of PPAR γ in at least one cell of the subject. In embodiments, the diabetes is type 2 diabetes. In the method, the cell(s) in which PPAR γ expression, level, or activity is increased can be any cell, from any tissue or organ, in the subject treated. In preferred embodiments, the cell(s) are white adipocyte tissue (WAT) cells, pancreatic cells, or both. In certain treatment methods, the methods do not cause an equivalent increase in PPAR γ expression, level, or activity in liver cells, as compared to the increase seen in WAT and/or pancreatic cells. In embodiments, no detectable increase in PPAR γ mRNA or protein is seen in a liver cell of a subject being treated. One exemplary embodiment of this aspect of the invention is a method of treating diabetes in which expression of PPAR γ is increased in certain cells of the subject, but not other cells, and in which the level of expression is not so high as to cause serious (or, in embodiments, any) noticeable or detectable deleterious effects on the short-term or long-term health of the subject. For instance, uncontrolled over-activation of PPAR γ in the liver could lead to liver injury. In treating diabetes according to the methods of the present invention, one effect that may be seen is an increase in interscapular brown adipose tissue (BAT) mass, which is a positive effect in the context of treatment of diabetes.

In yet another aspect of the invention, a method of lowering glucose levels is provided. The method comprises administering ABA to a subject suffering from diabetes or at risk of suffering from diabetes, or otherwise having acute or long-term high glucose levels in blood or tissues. The ABA is administered in an amount sufficient to lower the glucose levels in the patient, and especially to lower levels of free glucose in the blood of the subject. Lowering can occur at any time under any physiological condition, but is preferentially seen with regard to the subject's fasting glucose level. In a related method of the invention, a method of increasing the glucose tolerance of a subject is provided. The method comprises the same steps as other methods of the invention, and is similarly based, at least in part, on the underlying mechanisms of action of ABA, and the surprisingly selective nature of the effects of ABA on certain cells, but not others. In addition, like the other methods, it is based, at least in part, on the low toxicity of ABA and, as a corollary, the high activity of ABA in affecting PPAR γ expression.

Another aspect of the invention provides for effects on cells. These effects can be seen in vitro and in vivo. Certain effects have been discussed above, such as the effects on WAT, pancreatic cells, and BAT. In summary, the effects are to increase the levels of expression of PPAR γ in WAT and pancreatic cells, and to increase the mass of BAT. Additional effects provided by the methods of the invention include reducing the size of certain adipocytes and therefore preventing adipocyte hypertrophy and dysregulation (i.e., insulin resistance). Effects on liver cells and the liver in general are also seen as a result of practicing the methods of the invention. For example, a reduction in lipid accumulation in hepatocytes can be seen as an effect of the treatment (either in vivo administering or in vitro contacting) of the methods of the invention. As an outcome of this effect, the methods also provide a means for reducing the size of the liver of a subject, such as one suffering from diabetes (e.g., type 2 diabetes) or at risk of suffering from diabetes.

In addition to the methods provided above, the invention also provides methods that affect the immune system and the physiological effects of immune system functions. In general, the methods of this aspect of the invention are, like those above, based at least in part on the effect of ABA on PPAR γ expression, level, and/or activity. The methods of this aspect of the invention can be considered as any of the following, or any combination of the following: methods of decreasing T cell proliferation, in particular, in diabetics or those at risk for developing diabetes; methods of suppressing excessive immune responses, including autoimmune responses, (in both diabetics and non-diabetics); and methods of protecting pancreatic beta cells from lipotoxicity and damage associated with immunoinflammatory responses. The methods of this aspect of the invention generally comprise administering to a subject in need ABA in an amount sufficient to produce the desired effect, whether it be preventing overactivation of the immune system, decrease in T cell proliferation, or beta cell protection. The amount to be administered can be any suitable amount, as can be determined by application of known parameters in view of the amounts disclosed herein. Administration may be through any suitable route and by any suitable regimen, in accordance with the discussion above. Of course, where applicable (e.g., methods of inhibiting T cell proliferation), the methods according to this aspect of the invention may be in vitro or in vivo methods. In the method of decreasing T cell proliferation, the method can be, among other things, a method of reducing the number of CD4+ T cells, a method of preventing or treating autoimmune disorders including type 1 diabetes, inflammatory bowel disease, multiple sclerosis or arthritis. Likewise, in the method of down-regulating overactivation of the immune system, the method can be, among other things, a method of reducing the number of CD4+ T cells, a method of reducing the number of CD8+ T cells, or both. It can also be, among other things, a method of reducing interferon γ (IFN γ) expression or levels, or production of IFN γ, in and around T cells or by T cells, antigen-presenting cells (macrophages or dendritic cells), or in the subject's body in general.

For example, exposing cells, such as skeletal muscle cells or adipose tissue cells, to ABA can result in inhibition or a reduction in skeletal muscle macrophage infiltration, which can lead to a reduction or inhibition of inflammation resulting from the effects of these cells. This can be thought of either as an effect on the immune system, per se, or an effect on immune system function. Regardless of the way in which one considers the effect, the method provides a useful, convenient, and safe mode of treating a subject in need of such treatment. For example, it can benefit those suffering from inflammation in muscles or bone/muscle junctions, such as at tendons and ligaments. It can further benefit those suffering from diabetes, or those having a predisposition to diabetes, by reducing the number of macrophages in tissues and environments, where they can contribute to development or continuance of diabetes or a diabetic or pre-diabetic state.

As such, the methods can provide methods of reducing inflammation, including obesity-related inflammation. The methods can reduce inflammation systemically (i.e., throughout the subject's body) or locally (e.g., at the site of administration or the site of inflammatory cells, including but not limited to T cells and macrophages). In treating or preventing obesity-related inflammation according to the methods of the present invention, one effect that may be seen is the decrease in the number of macrophages infiltrating the white adipose tissue and skeletal muscle tissue and a down-regulation of tumor necrosis factor-alpha expression in adipose tissue and skeletal muscle tissue. The methods can thus also be considered methods of affecting or altering the immune response of a subject to whom the ABA is administered.

In view of the above methods, it should be evident that the present invention provides ABA for use in contacting cells, such as in treating cells of a subject. The above discussion focuses on the use of ABA alone or as part of a composition for use in what could generally be considered a pharmaceutical or medical setting. However, it is to be understood that the ABA or compositions comprising ABA can be used in treatment of subject by way of nutritional supplements, such as through dietary supplements. In such supplements, the ABA can be present in doses that are suitable for daily (or more often) administration. Typically, for dietary supplements, the ABA is presented in a form suitable for oral ingestion, such as by way of pill, capsule, tablet, caplet, powder, liquid, or the like. As with the forms for use in medical settings, typical additives can be included, such as colorants, flavorants, binders, gums, and the like.

For example, the ABA may be present as a functional food ingredient, either as a stand-alone ingredient (such as would be seen with sugar, salt, pepper, etc.) or as an ingredient included in the food during processing or packaging. In such situations, the ABA and compositions comprising it would include ABA at an appropriate amount for oral ingestion. It is envisioned that this amount would be considerable less, on a gram of product ingested basis, than the amount used for pharmaceutical use in treating diabetes, prediabetes, impaired glucose tolerance, and insulin resistance or prophylactically treating those at risk for developing prediabetes, diabetes, impaired glucose tolerance, and insulin resistance.

In yet another form of the composition, a nutritional supplement is provided for treatment of diabetes or for treatment of those at risk for developing diabetes. In this form, the ABA is provided at a higher concentration than the food supplement form, but still at a lower dose than the "pharmaceutical" dose. This form can be considered a supplement for periodic administration of ABA to a subject. For example, it can be likened to a vitamin pill for periodic supplementation of various vitamins and minerals for a person, but rather than providing vitamins and minerals, it would provide ABA to enable the various beneficial effects discussed in this document, as well as others. The dietary supplement may comprise, in addition to ABA, any number of other substances, which are well known as suitable for ingestion by animals and humans. For example, it may contain fillers, binders, gums, colorants, and the like.

As should be evident, the ABA may be provided in a pharmaceutically acceptable form. Thus, ABA can be provided in a form that is suitable for administration to a subject in need of it. It also may be present as a component of a composition, and in particular, a pharmaceutical composition. The ABA may be provided as a purified or semi-purified substance, or as a part of a simple or complex composition. Where present as part of a composition, the composition as a whole should be biologically tolerable at the amount to be exposed to a living cell. Thus, the composition may comprise toxic or otherwise deleterious substances when in its as-produced state, but be rendered non-toxic at a later date by further treatment or simply by dilution. The pharmaceutical composition may comprise any number of substances in addition to ABA, such as, but not limited to, water, salts, sugars, buffers, biologically active compounds, drugs, etc.

The ABA and compositions of the invention can be provided in any suitable form and container. Thus, in another aspect, the invention provides for a container containing ABA or a composition comprising ABA. In this aspect, the ABA or composition will be provided in the container in an amount that is sufficient for at least one use in a method according to the invention. Thus, it can be provided in an amount and in a form that is sufficient for one or more in vitro treatments of a cell for research purposes. It can also be provided in an amount and form that is sufficient for one or more in vivo treatments of a diabetic or person susceptible to developing diabetes. One of skill in the art can immediately contemplate the various numerous other amounts, forms, and uses for the various in vitro and in vivo applications, and thus all such amounts, forms, and uses need not be detailed here.

The container of the invention can be any container, fabricated in any shape and from any suitable material. It thus can be made from plastic, glass, paper or a paper product, metal, or some other polymeric material. It can be in any shape and size, such as in the shape of a tube, vial, ampoule, packet, pouch, wrapper, can, bottle, and box. Those of skill in the medical, dietary supplement, and food arts will immediately recognize the various other shapes, materials, and sizes that are suitable, and therefore these need not be detailed herein.

In yet an additional aspect, the ABA, compositions, and/or containers, or combinations of these, can be provided in the form of a kit. For example, two or more containers containing a pharmaceutical formulation according to the invention may be provided together in a single package, referred to herein as a kit. Likewise, ABA and some or all reagents and supplies necessary for performing an in vitro assay according to the invention can be provided in a single package or kit. Numerous configurations of supplies and reagents may be included in the kit, in accordance with similar kits for pharmaceutical, dietary supplementation, and/or research that are known in the art.

DEFINITIONS

Unless otherwise stated, the following definitions are used throughout the present application:

Analysis of Variance (ANOVA): Arithmetic process for partitioning the overall variation in data sets into specific components based on sources of variation. It has been used to determine whether numerical differences between treatment groups are statistically significant.

Adipogenesis: the process by which new adipocytes or fat storage cells are generated.

Allele: one of a number of viable DNA codings of the same gene.

Conjugated diene: a molecule containing two double bonds separated by a single bond.

Db/db mice: Term used to define a type of mouse which lacks both alleles of a long isoform of leptin receptor. This deficiency results in a high predisposition to developing type 2 diabetes. Reference is made to Experiments 1 and 3-6 (infra.) for further discussions on Db/db mice.

Enantiomer: optical isomer; chemical classification of molecules based on their ability to rotate the plain of polarization clockwise (+) or anti-clockwise (−).

Glycemia: concentration of glucose in blood.

Hyperglycemia: increased concentrations of glucose in blood beyond the normal ranges.

Hyperinsulinemia: increased concentrations of insulin in blood beyond the normal ranges.

Insulinemia: concentration of insulin in blood.

Insulin resistance: inability of tissues to respond to insulin and take up glucose from the blood.

Substantially pure: having a purity of at least 90% by weight, preferably at least 95% by weight such as at least 98%, 99% or about 100% by weight.

Type 2 diabetes or Non-insulin dependent Diabetes Mellitus: term referring to a common type of diabetes caused by an unresponsiveness of cells to the actions of insulin. If the cells do not respond to insulin, they are unable to take up glucose from blood, which results in glucotoxicity. In addition, the cells are deprived from the energy derived from glucose oxidation.

Abscisic Acid (ABA): The term used herein refers to a plant hormone containing a trimethylcyclohexene ring with one or more hydroxy groups (for instance a 6-hydroxy group), a 3-oxo group and an unsaturated side chain in the sixth position of the trimethylcyclohexen ring containing cis-7, trans-9 double bonds its non-toxic salts, active esters, active isomers, active metabolites, active structurally related compounds and mixtures thereof. Non-toxic salts include, for example, alkyl esters having from 1 to 6 carbon atoms in the alkyl group, as well as mono-, di- and tri-glycerides, and mixtures thereof. Active isomers of abscisic acid include geometrical isomers and its non-toxic salts, e.g., sodium, potassium, calcium and magnesium salts, and its active esters, e.g., alkyl esters having from 1 to 6 carbon atoms in the alkyl group, as well as mono-, di- and tri-glycerides, and mixtures thereof. Active optical isomers of abscisic acid include the (+)-enantiomer and the (−)-enantiomer and its non-toxic salts, e.g., sodium, potassium, calcium and magnesium salts, and its active esters, e.g., alkyl esters having from 1 to 6 carbon atoms in the alkyl group, as well as mono-, di- and tri-glycerides, and mixtures thereof. Active metabolites of abscisic acid include oxygenated abscisic acid analogs, including but not limited to, 8'-hydroxyABA, (+)-7'-hydroxyABA, 9'-hydroxyABA, 2'3'-dihydroABA, 8'-hydroxy-2',3'-dihydroABA, neophaseic acid (neoPA) and its non-toxic salts, e.g., sodium, potassium, calcium and magnesium salts, and its active esters, e.g., alkyl esters having from 1 to 6 carbon atoms in the alkyl group, as well as mono-, di- and tri-glycerides, and active structurally related compounds thereof, including but not limited to compounds with conjugated double bonds (e.g., conjugated dienes, conjugated trienes conjugated tetraenes) in the side chain and compounds containing a trimethylcyclohexene ring, with or without hydroxy groups; active analogs thereof such as those described in The Merck Index, Eighth Edition, page 1711; active conjugated abscisic acids thereof such as β-D-glucopyranosyl abscisate (ABAGE) and abscisic acid-1'-β-D-glucopyranoside (ABAGS), and mixtures thereof.

Abscisic acid may be a substantially pure single chemical compound or a mixture of one or more abscisic acid compounds as defined above. For example, the abscisic acid may be in the form of an extract obtainable or obtained from plant extracts, either directly or following one or more steps of purification.

The abscisic acid used in the described methods may be in a free acid form or bound chemically through ester linkages. In its natural form, abscisic acid is heat stable. Abscisic acid may be used in its natural state or in a dried and powdered form. Further, the free acid form of abscisic acid may be converted into a non-toxic salt, such as sodium, potassium or calcium salts, by reacting chemically equivalent amounts of the free acid form with an alkali hydroxide at a basic pH.

The abscisic acid may be a substantially pure single chemical compound or a mixture of one or more abscisic acid compounds as defined above. The term substantially pure means having a purity of at least 90% by weight, including all specific integers above 90%. Preferably it has a purity of at least 95% by weight, such as at least 98%, 99%, or 100% or about 100% by weight. For example, the abscisic acid may be in the form of an extract obtainable or obtained from plants, either directly or following one or more steps of purification.

Administration—In the course of the method of the present invention, a therapeutically effective amount of abscisic acid compound can be administered to an animal, including mammals and humans, in many ways. While in the preferred embodiment, the abscisic acid compound is administered orally or parenterally, other forms of administration such as through medical compounds or aerosols are also contemplated.

For oral administration, the effective amount of abscisic acid may be administered in, for example, a solid, semi-solid, liquid, or gas state. Specific examples include tablet, capsule, powder, granule, solution, suspension, syrup, and elixir agents. However, the abscisic acid compound is not limited to these forms.

To formulate the abscisic acid of the present invention into tablets, capsules, powders, granules, solutions, or suspensions, the abscisic acid compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

For parenteral administration, the abscisic acid compound of the present invention may be administered rectally or by injection. For rectal administration, a suppository may be used. The suppository may be prepared by mixing the abscisic acid of the present invention with a pharmaceutically suitable excipient that melts at body temperature but remains solid at room temperature. Examples include but are not limited to cacao butter, carbon wax, and polyethylene glycol. The resulting composition may be molded into any desired form using methods known to the field.

For administration by injection, the abscisic acid compound of the present invention may be injected hypodermically, intracutaneously, intravenously, or intramuscularly. Medicinal drugs for such injection may be prepared by dissolving, suspending or emulsifying the abscisic acid of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added. While not required, it is preferred that the composition be sterile or sterilized.

For formulating the abscisic acid of the present invention into suspensions, syrups or elixirs, a pharmaceutically suitable solvent may be used. Included among these is the non-limiting example of water.

The abscisic acid compound of the present invention may also be used together with an additional compound having other pharmaceutically suitable activity to prepare a medicinal drug. A drug, either containing ABA as a stand-alone compound or as part of a composition, may be used in the treatment of subjects in need thereof.

The abscisic acid of the present invention may also be administered in the form of an aerosol or inhalant prepared by charging the abscisic acid in the form of a liquid or fine powder, together with a gaseous or liquid spraying agent and, if necessary, a known auxiliary agent such as an inflating agent, into a non-pressurized container such as an aerosol container or a nebulizer. A pressurized gas of, for example, dichlorofluoromethane, propane or nitrogen may be used as the spraying agent.

Abscisic acid may be administered to an animal, including mammals and humans, in need thereof as a pharmaceutical or veterinary composition, such as tablets, capsules, solutions, or emulsions. In a preferred embodiment of the invention, the free acid form of punicic acid is administered. However, administration of other forms of abscisic acid, including but not limited to esters thereof, pharmaceutically-suitable salts thereof, metabolites thereof, structurally related compounds thereof, analogs thereof, and combinations thereof, in a single dose or a multiple dose, are also contemplated by the present invention.

Abscisic acid may also be administered to an animal in need thereof as a nutritional additive, either as a food or nutraceutical supplement.

The terms "preventing" or "treating", "treating" or "ameliorating" and similar terms used herein, include prophylaxis and full or partial treatment. The terms may also include reducing symptoms, ameliorating symptoms, reducing the severity of symptoms, reducing the incidence of the disease, or any other change in the condition of the patient, which improves the therapeutic outcome.

The abscisic acid is preferably used and/or administered in the form of a composition. Suitable compositions are, preferably, a pharmaceutical composition, a foodstuff or a food supplement. These compositions provide a convenient form in which to deliver the abscisic acid. Compositions of the invention may comprise an antioxidant in an amount effective to increase the stability of the abscisic acid with respect to oxidation.

The amount of abscisic acid that is administered in the method of the invention or that is for administration in the use of the invention is any suitable amount. It is preferably from about 0.0001 g to about 20 g (more preferably 0.01 g to 1 g, such as 0.05 g to 0.5 g) of abscisic acid or derivative thereof per day. Suitable compositions can be formulated accordingly. Those of skill in the art of dosing of biologically active agents will be able to develop particular dosing regimens for various subjects based on known and well understood parameters.

A preferred composition according to the invention is a foodstuff. Food products (which term includes animal feed) preferably contain a fat phase, wherein the fat phase contains abscisic acid. The foodstuffs are optionally used as a blend with a complementary fat. For example, the fat may be selected from: cocoa butter, cocoa butter equivalents, palm oil or fractions thereof, palmkernel oil or fractions thereof, inter-esterified mixtures of those fats or fractions thereof. It may also contain liquid oils, such as those selected from: sunflower oil, high oleic sunflower oil, soybean oil, rapeseed oil, cottonseed oil, fish oil, safflower oil, high oleic safflower oil, corn oil, and MCT-oils. Examples of suitable foodstuffs include those selected from the group consisting of margarines, fat continuous or water continuous or bicontinuous spreads, fat reduced spreads, confectionery products such as chocolate or chocolate coatings or chocolate fillings or bakery fillings, ice creams, ice cream coatings, ice cream inclusions, dressings, mayonnaises, cheeses, cream alternatives, dry soups, drinks, cereal bars, sauces, snack bars, dairy products, clinical nutrition products, and infant formulations.

Other non-limiting examples of compositions are pharmaceutical compositions, such as in the form of tablets, pills, capsules, caplets, multiparticulates (including granules, beads, pellets and micro-encapsulated particles); powders, elixirs, syrups, suspensions, and solutions. Pharmaceutical compositions will typically comprise a pharmaceutically acceptable diluent or carrier. Pharmaceutical compositions are preferably adapted for administration parenterally (e.g., orally). Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the ABA on the subject.

Pharmaceutically acceptable carriers suitable for use in such compositions are well known in the art of pharmacy. The compositions of the invention may contain 0.01-99% by weight of abscisic acid. The compositions of the invention are generally prepared in unit dosage form. Preferably the unit dosage of abscisic acid is from 1 mg to 1000 mg (more preferably from 50 mg to 500 mg). The excipients used in the preparation of these compositions are the excipients known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like. Preferably, the unit dosage of abscisic acid in the food supplements is from 1 mg to 1000 mg (more preferably from 50 mg to 500 mg).

In general, the term carrier may be used throughout this application to represent a composition with which ABA may be mixed, be it a pharmaceutical carrier, foodstuff, nutritional supplement or dietary aid. The materials described above may be considered carriers of ABA for the purposes of the invention. In certain embodiments of the invention, the carrier has little to no biological activity on PPAR γ.

Dose—The method of the present invention can comprise administering a therapeutically effective amount of abscisic acid compound to an animal in need thereof. The effective amount of abscisic acid depends on the form of abscisic acid compound administered, the duration of the administration, the route of administration (e.g., oral or parenteral), the age of the animal and the condition of the animal, including mammals and humans.

For instance, an amount of abscisic acid effective to treat or prevent type 2 diabetes, prediabetes, impaired glucose tolerance, or insulin resistance in an animal can range from 0.1-10,000 mg/kg/day. A preferred effective amount of abscisic acid is 1 to 5,000 mg/kg/day, with a more preferred dose being 2 to 100 mg/kg/day. The upper limit of the effective amount to be administered is not critical, as abscisic acid is relatively non-toxic as long as the recipient's diet contains the necessary essential nutrients. The effective amount of abscisic acid is most effective in treating or preventing type 2 diabetes, pre-diabetes, impaired glucose tolerance, and insulin resistance of an animal when administered to an animal for periods ranging from about 7 to 100 days, with a preferred period of 15 to 50 days, and a most preferred period of 30 to 42 days.

An amount of abscisic acid which is most effective in preventing over-activation of the immune system can range from 0.1 to 500 mg/kg/day, with a preferred dose of 1 to 150 mg/kg/day.

When the effective amount of the abscisic acid compound of the present invention is administered in a nutritional, medical or veterinary composition, the preferred dose ranges from about 0.01 to 2.0% wt/wt to the food or nutraceutical product.

Preparation of abscisic acid—Abscisic acid has previously been extracted from leaves of Lupin (*Lupinus cosentinii*), Apricot (*Prunus armeniaca*), Avocado (*Persea Americana*), Sunflower (*Helianthus annuus*), Grapevine (*Vitis vinifera*), Tomato (*Lycopersicon esculentum*), Spinach (*Spinacia oleracea*), Orange (*Citrus sinensis*) and Mango (*Mangifera indica*) (46). ABA and its metabolites have also been isolated from *Brassica napus* and *Brassica rapa* seed (47) and could also be isolated from fruits and any other plant materials. The abscisic acid compound has been extracted from plant leaves through many procedures, including: 1) methanol extraction; 2) cold water extraction or 3) boiling water extraction (Loveys, 1988). For the methanol extraction, samples of leaf material were homogenized in aqueous methanol, the homogenate was centrifuged and the pellet re-extracted with methanol. Water was added to the combined supernatants before evaporation. The resulting extract was adjusted to a pH of 2.5 and the abscisic acid compound extracted with three washes of ethyl acetate. The ethyl acetate extracts can be further purified by chromatography. The cold water and boiling water methods consist of homogenization of plant materials in cold or boiling water, respectively prior to the ethyl acetate extraction.

In certain other embodiments, the present invention provides for use of abscisic acid and structurally related compounds, such as a compound selected from the group consisting of abscisic acid, esters thereof, pharmaceutically suitable salts thereof; metabolites thereof, structurally related compounds thereof, or combinations thereof in the treatment and prevention of IBD and GI tract inflammation.

In addition, in general, the present invention relates to inhibition of inflammation in the GI tract, wherein the relevant components include the stomach, small intestine, large intestine, and rectum. The effect results from the exposure of ABA to various cell types in the body that induces a biological effect. The cells may include those from GI tract tissues, immune cells (i.e. macrophages, monocytes, lymphocytes), or epithelial cells. In certain embodiments, the invention provides for treating subjects with ABA, for example as a dietary supplement, to reduce or prevent inflammation related to inflammatory bowel disease, either Crohn's Disease or Ulcerative Colitis. The present invention also contemplates the administering of ABA to the GI tract in order to suppress the expression of cellular adhesion molecules in the gut.

When practiced, the methods of this embodiment of the invention can be by way of administering ABA to a subject via any acceptable administration route using any acceptable form, as is described above, and allowing the body of the subject to distribute the ABA to the target cell through natural processes. As is described above, administering can likewise be by direct injection to a site (e.g., organ, tissue) containing a target cell (i.e., a cell to be treated).

Furthermore, administering can follow any number of regimens. It thus can comprise a single dose or dosing of ABA, or multiple doses or dosings over a period of time. Accordingly, treatment can comprise repeating the administering step one or more times until a desired result is achieved. In certain embodiments, treating can continue for extended periods of time, such as weeks, months, or years. Those of skill in the art are fully capable of easily developing suitable dosing regimens for individuals based on known parameters in the art. The dosage amounts for ABA described above may be used in the methods of these embodiments of the invention. For the treatment of IBD, GI tract inflammation or suppressing expression of cellular adhesion molecules in the gut, it is preferred that ABA be administered at amounts of about 1 mg/day to 5,000 mg/day.

The amount to be administered will vary depending on the subject, stage of disease or disorder, age of the subject, general health of the subject, and various other parameters known and routinely taken into consideration by those of skill in the medical arts. As a general matter, a sufficient amount of ABA will be administered in order to make a detectable change in the amount of inflammation in the GI tract, which with IBD is often related to the amount of pain an individual is experiencing. With patients not currently experiencing IBD symptoms, the change one might look for may involve immune cell parameters such as CTLA-4 expression on CD4+ T-cells or the percent of regulatory T-cells in the blood. Suitable amounts are disclosed herein, and additional suitable amounts can be identified by those of skill in the art without undue or excessive experimentation, based on the amounts disclosed herein.

In one aspect, the invention provides a method of treating or preventing a subject suffering from IBD, or otherwise healthy individuals, perhaps with a genetic predisposition for Chohn's Disease or Ulcerative Colitis, from developing IBD. The method may also involve treating those with a remissive form of IBD. According to the invention, the term "a subject suffering from IBD" is used to mean a subject (e.g., animal, human) having a disease or disorder showing one or more clinical signs that are typical of IBD. In general, the method of treating or preventing according to this aspect of the invention comprises administering to the subject an amount of ABA therapy that is effective in treating or preventing one or more symptoms or clinical manifestations of IBD, or in preventing development of such symptom(s) or manifestation(s).

Thus, according to the methods of the invention, the invention can provide methods of treatment of IBD, inflammation associated with enteric infection and inflammation associated with autoimmune diseases. The methods of treatment can be prophylactic methods. In certain embodiments, the method is a method of treating IBD, inflammation associated with enteric infection and inflammation associated with autoimmune diseases. In other embodiments, the method is a method of preventing IBD. In some embodiments, the method is a method of preventing a remissive form of IBD from becoming active. In still other embodiments, the method is a method of improving the health status of a subject suffering from IBD, inflammation associated with enteric infection and inflammation associated with autoimmune diseases. Organisms causing gastroenteric infections include but are not limited to: *Escherichia coli, Shigella, Salmonella*, pathogenic *Vibrios, Campylobacter jejuni, Yersina enterocolitica, Toxoplasma gondii, Entamoeba histolytica* and *Giardia lamblia*. Accordingly, in certain embodiments, the invention provides a method of protecting the health, organs, and/or tissues of a subject suffering from IBD, inflammation associated with enteric infection and inflammation associated with autoimmune diseases or at risk from developing IBD, inflammation associated with enteric infection and inflammation associated with autoimmune diseases.

In one embodiment of the invention, the method of treating IBD comprises treating IBD without causing discernable side-effects, such as significant weight gain, systemic immune suppression, cushingoid appearance, osteopenia/osteoporosis, or pancreatitis that is common with currently available IBD treatments (i.e. corticosteroids, tumor necrosis factor α inhibitors). That is, it has been found that the method of treating according to the present invention, which provides the treatment effect, at least in part, by affecting the expression and/or activation of PPAR γ in some cells, provides the beneficial effect without causing a significant gain in weight, for example by fluid retention, in the subject being treated, as compared to other similar subjects not receiving the treatment. While not wishing to be bound by any particular theory as to why this effect is seen, it is likely that treatment with ABA therapy, while causing an increase in PPAR γ expression in some cells, does not cause over-expression or over-activation, as is commonly seen with some other (e.g., synthetic) PPAR γ agonists currently known for treatment of diseases associated with PPAR γ.

As such, the methods of the present invention can provide methods of reducing inflammation. The methods can reduce inflammation systemically (i.e., throughout the subject's body) or locally (e.g., at the site of administration or the site of inflammatory cells, including but not limited to T cells and macrophages). In treating or preventing inflammation according to the methods of the present invention, one effect that may be seen is the decrease in the number of blood monocytes or macrophages and lymphocytes infiltrating the intestine. Another may be the increase in regulatory immune cell populations, such as $CD4^+CD25^+FoxP3^+$ regulatory T-cells, or an increase in regulatory properties of lymphocytes or macrophages (e.g. increased interleukin 4 (IL-4) or IL-10, increased CTLA-4 expression, or decreased TNF-α and IL-6). Another may be the decreased presence of inflammatory genes and/or adhesion molecules. The methods can thus also be considered methods of affecting or altering the immune response of a subject to whom the ABA therapy is administered. The subject may have inflammatory bowel disease or another condition in which the immunomodulation of T cells or downregulation of cellular adhesion molecules is a desired outcome.

In view of the above methods, it should be evident that the present invention provides ABA therapy for use in contacting cells, such as in treating cells of a subject. The above discussion focuses on the use of ABA as part of a composition for use in what could generally be considered a pharmaceutical or medical setting.

ABA for the treatment of IBD and GI tract inflammation may be formulated as a pharmaceutical, nutritional composition, functional food composition, or dietary aid, as are described in greater detail above.

EXAMPLES

The invention will be further explained by the following Examples, which are intended to be purely exemplary of the invention, and should not be considered as limiting the invention in any way. In the Examples and throughout this specification, all percentages, part and ratios are by weight unless indicated otherwise.

Thiazolidinediones (TZDs) are synthetic ligands of peroxisome proliferator-activated receptor γ (PPAR γ) currently used in the treatment of Non-Insulin Dependent Diabetes Mellitus (NIDDM). Despite their efficacy, TZDs are associated with a number of side effects, such as weight gain, hepatotoxicity, and congestive heart failure that have limited their use by millions of diabetic patients. We have investigated the ability of abscisic acid (ABA), a naturally occurring phytochemical, to activate PPAR γ. We found that ABA induced transactivation of PPAR γ in 3T3-L1 pre-adipocytes in vitro. We next examined the effect of dietary ABA-supplementation (100 mg/kg) on glucose tolerance, obesity-related inflammation, and mRNA expression of PPAR γ and PPAR γ-responsive genes in white adipose tissue (WAT) of db/db mice fed high fat diets. Dietary ABA-supplementation for 36 days ameliorated fasting blood glucose and glucose tolerance during a glucose tolerance test, and increased mRNA expression of PPAR γ and its responsive genes (i.e., adiponectin, aP2, and CD36) in WAT. We also found that adipocyte hypertrophy, tumor necrosis factor-α (TNF-α) expression, and macrophage infiltration in WAT were significantly attenuated in ABA-fed mice. These findings indicate that ABA can be used as a nutritional and pharmaceutical intervention against diabetes, and in particular NIDDM, and against inflammation, including obesity-related inflammation.

An objective of the studies presented below was to determine whether the naturally occurring phytochemical, ABA, was a novel PPAR γ ligand that could be used as a safer alternative to TZDs. The results from the transfection assay demonstrated for the first time that ABA activated PPAR γ in 3T3-L1 pre-adipocytes in vitro. Furthermore, we found that ABA was 10 times less potent than the synthetic agonist rosiglitazone. Other natural substances, including fatty acids and eicosanoids (27), components of oxidized low-density lipoproteins (29), have also been found to activate PPAR γ in vitro. However, PPAR γ activation in vitro does not always result in transcriptional regulation of PPAR-responsive genes or beneficial health effects in vivo (7, 27).

ABA is a widely studied naturally occurring phytohormone that plays a key role in many different processes in plants, including stress response, leaf abscission, growth and development, and germination (39-42). Interestingly, ABA is also a key component of sugar sensitivity, as plants deficient of ABA are glucose insensitive (42, 43). While ABA is ubiquitously found in plants, and therefore consumed by humans as a part of the daily diets, its natural content ranges from 5-15 mg/kg in leaves (44). Thus, the doses that can be attained by vegetable intake would be significantly lower than those required for efficacy against non-insulin dependent diabetic and pre-diabetic states. This is the first study to explore the effect of this bioactive molecule in the prevention of NIDDM. Our finding that ABA is a novel PPAR γ ligand opens the possibility that this compound could be used as a safe and effective alternative to the synthetic agonists for the 20.8 million Americans with NIDDM and the millions more who have prediabetes. There are no preventative medications currently available to the latter group. The potential for ABA as an everyday nutritional supplement for the treatment or prevention of NIDDM is promising, and as more is learned about other uses of PPAR γ agonists for treating chronic diseases such as atherosclerosis and inflammatory bowel disease, this potential will only continue to grow.

Example 1

Research Design and Methods

A. Transfection of 3T3-L1 Preadipocytes

Transformation plasmid DNA was performed using One Shot TOP10 (Invitrogen, Carlsbad, Calif.). Briefly, 3 μA of the ligation reaction were added to a thawed 50 μl vial of One Shot® cells for each reaction. The vials were then set on ice for 30 minutes, followed by 30 seconds incubation in a 42° C. water bath. Afterwards, 250 μl of pre-warmed S.O.C medium was added to each vial. Vials were then secured on their sides in a microcentrifuge rack and were placed in a Gyromax 727 orbital shaking incubator (Amerex Instruments, Lafayette, Calif.) and incubated at 37° C. at 225 rpm. After 1 hour incubation, 100 μl of each transformation vial was spread on separate, labeled LB agar plates (Sigma-Aldrich, Milwaukee, Wis.), inverted, and incubated at 37° C. overnight. Colonies were selected and isolated using Plasmid Maxi Kit (Qiagen, Valencia, Calif.) according to manufacturer's instructions. After isolation, the plasmids were transfected into 3T3-L1 pre-adipocytes (American Type Culture Collection, Manassas, Va.) using the Targefect-BAC transfection kit. (Targeting Systems, Santee, Calif.). Briefly, 3T3-L1 cells were cultured in complete DMEM high glucose media (Invitrogen) at 37° C. for 2 days until confluence. After digestion with 2 ml trypsin (Mediatech, Herndon, Va.), the cells were resuspended in 6 ml high glucose DMEM (Mediatech) and then aliquoted into a 24 well plate. Following an overnight incubation at 37° C. in a humidified atmosphere containing 5% $CO_2$, 50 μl of the transfection complex was added to new media for each well. Each 50 μl transfection complex contained 0.8 μg plasmid DNA and 1.5 μl Targefect (Targeting Systems). After another overnight incubation at 37° C., racemic ABA (1, 2.5, 5, 10, and 50 μM) and rosiglitazone (1 μM) were added to their respective wells in duplicate and incubated at 37° C. for 24 hours. On the day of the reading, the cells were washed with 500 μl PBS and lysed with 100 μl lysis reagent (Promega, Madison, Wis.). After 15 minutes, lysed cells were collected and luciferase activity for each concentration was calculated using the Dual-Luciferase reporter assay system (Promega) and TD-20/20 Single-Tube Luminometer (Turner Biosystems, Sunnyvale, Calif.) according to manufacturers' instructions. Relative luciferase activity (RLA) was calculated as a ratio of the chemiluminescence 10 seconds after the Luciferase Assay Reagent II (Promega) was added over the chemiluminescence 10 seconds after the Stop&Glo Reagent (Promega).

B. Mice and Dietary Treatments

Four week-old, male BKS.Cg-+$Lepr^{db}$/+$Lepr^{db}$/OlaHsd (db/db) mice were purchased from Harlan Laboratories (Indianapolis, Ind.) and maintained at the animal facilities at Virginia Polytechnic Institute and State University in a room maintained at 75° F., with a 12:12 h light-dark cycle starting from 6:00 AM. All experimental procedures were approved by the Institutional Animal Care and Use Committee of Virginia Polytechnic Institute and State University and met or exceeded requirements of the Public Health Service/National Institutes of Health and the Animal Welfare Act.

Experiment 1: mice (n=25) were fed high-fat (>40% energy from fat), isocaloric, isonitrogenous diets containing 0, 100, 200, 400, and 800 mg of a racemic (±) ABA mixture/kg diet for 36 days (Table 1) (Sigma). These doses were chosen based on the standard concentrations of TZDs utilized in the treatment of NIDDM. The mice were weighed and their food intake was recorded daily. On day 36 of the study fasted mice (12 h) were bled through the caudal vein and fasting blood glucose concentrations were determined. To investigate the ability of ABA to normalize glucose concentrations, an intraperitoneal glucose tolerance test (IPGTT) was performed on day 36 on the fasted mice. Briefly, mice were bled at 0, 10, 25, and 45 minutes following the administration of glucose (2 g/kg) for measurement of plasma glucose levels. Following the IPGTT, the mice were killed by $CO_2$ narcosis and WAT was excised and stored in RNA later (Ambion, Austin, Tex.), a commercial solution that inhibits RNases. Weights were recorded for WAT, interscapular brown adipose tissue (BAT), and liver.

Experiment 2: The ABA dose utilized (100 mg ABA/kg) was based on the results obtained from the IPGTT of the ABA titration study (i.e., Experiment 1). Mice in experiment 2 were fed high-fat diets containing 0 or 100 mg ABA/kg for 36 days. Their body weights and food intake was recorded daily, and blood was collected on day 36 of the study during an IPGTT. This IPGTT included one additional 100 minutes time point. Following the IPGTT the mice were killed and WAT was collected and stored in RNA later (Ambion) for RNA isolation and gene expression analyses and in 10% buffered neutral formalin for histological evaluation. Weights were recorded for abdominal WAT, BAT, and liver.

C Histopathology

Hepatic and adipose sections were fixed in 10% buffered neutral formalin, embedded in paraffin, cut at thicknesses of 7 microns and later stained with hematoxylin and eosin (H&E) for histological examination of adipocyte hypertrophy and inflammatory lesions. Hepatic sections were scored based on the amount of lipodystrophy observed according to the Nonalcoholic steatohepatitis (NASH) scoring method, with a score of 0 signifying <5% of the cells contain lipid droplets and a score of 4 signifying that >75% of the cells contained lipids and a magnification of 400× (23). The final score was the average of five randomly chosen fields. The area of adipocytes from WAT was analyzed using Sigma Pro® 5.0 software at a magnification of 100×, and macrophage infiltration was determined by averaging the number of macrophages observed in five different fields at 400×.

D. Quantitative Real-Time Reverse Transcriptase PCR

Total RNA was isolated from WAT using the RNA isolation Lipid Tissue Minikit (Qiagen) according to the manufacturer's instructions. Total RNA (1 μg) was used to generate complementary DNA (cDNA) template using the iScript cDNA Synthesis Kit (Bio-Rad, Hercules, Calif.). The total reaction volume was 20 μl with the reaction incubated as follows in the Tetrad Thermocycler: 5 minutes at 25° C., 30 minutes at 52° C., 5 minutes at 85° C., hold at 4° C. PCR was performed on the cDNA using Taq DNA polymerase Obtained from Invitrogen and using previously described conditions (24, 25). Each gene amplicon was purified with the MiniElute PCR Purification Kit (Qiagen) and quantitated on an agarose gel. These purified amplicons were used to optimize real-time PCR conditions and to generate standard curves in the real-time PCR assay. Primer concentrations and annealing temperatures were optimized for the iCycler iQ system (Bio-Rad) for each set of primers using the system's gradient protocol (Table 1). PCR efficiencies were maintained at 100% for each primer set during optimization and also during the real-time PCR of sample DNA.

Complementary DNA (cDNA) concentrations for .beta.-actin, PPAR γ, PPAR α, PPAR .delta., adiponectin, CD36, aP2, and TNF-α were examined by real-time quantitative PCR using and iCycler IQ System and the iQ SYBR green supermix (Bio-Rad). SYBR green I is a general double-stranded DNA intercalating dye and, therefore, may detect nonspecific products and primer/dimers in addition to the amplicon of interest. In order to determine the number of products produced during the real-time PCR, a melting curve analysis was performed on each product. Real-time PCR was used to measure the starting amount of nucleic acid of each unknown sample of cDNA on the same 96-well plate. Results are presented as starting quantity of cDNA (picograms) per microgram of mRNA.

TABLE 1

Oligonucleotide Sequences for Quantitative Real-Time PCR

| Primer | Sequence | Length | Acc. No. | SEQ ID NO. |
|---|---|---|---|---|
| PPAR αF | 5'GGGGACTGCCGTTGTCTGT3' | 143 | NM_011144 | 1 |
| PPAR αR | 5'GGGGACTGCCGTTGTCTGT3' | | | 2 |
| PPAR δF | 5'ACAGTGACCTGGCGCTCTTC3' | 96 | U10375 | 3 |
| PPAR δR | 5'TGGTGTCCTGGATGGCTTCT3' | | | 4 |
| PPAR γF | 5'CAGGCTTGCTGAACGTGAAG3' | 117 | NM_011146 | 5 |
| PPAR γR | 5'GGAGCACCTTGGCGAACA3' | | | 6 |
| CD36F | 5'CCGGGCCACGTAGAAAACA3' | 156 | NM_007643 | 7 |
| CD36R | 5'CCTCCAAACACAGCCAGGAC3' | | | 8 |
| β-actinF | 5'CCCAGGCATTGCTGACAGG3' | 141 | X03672 | 9 |
| β-actinR | 5'TGGAAGGTGGACAGTGAGGC3' | | | 10 |
| AdiponectinF | 5'ACAAGGCCGTTCTCTTCACC3' | 123 | NM_009605 | 11 |
| AdiponectinR | 5'CCCCATCCCCATACACCTG3' | | | 12 |
| aP2F | 5'TCTCTTATCAAAGGCTCTACTTCC3' | 78 | NM_001442 | 13 |
| aP2R | 5'CAAAATTCCATCCAGGCCTCT3' | | | 14 |
| TNF-αF | 5'ACTGCCAGAAGAGGCACTCC3' | 137 | M_13049 | 15 |
| TNF-αR | 5'CGATCACCCCGAAGTTCA3' | | | 16 |

F, forward: R, reverse. PCR primer pairs were designed for an optimal annealing temperature of 57° C. and product length shorter than 157 base pairs.

E. Statistics

Data were analyzed as a completely randomized design. To determine the statistical significance of the model, analysis of variance (ANOVA) was performed using the general linear model procedure of Statistical Analysis Software (SAS) as previously described (24). A P<0.05 was considered to be significant. When the model was significant, ANOVA was followed by Sheffe's multiple comparison method. Nonparametric data were analyzed by using the Mann-Whitney U test followed by a Dunn's multiple comparison's test.

Example 2

ABA Activates PPAR γ in 3T3-L1 Pre-Adipocytes In Vitro

Figure 2:
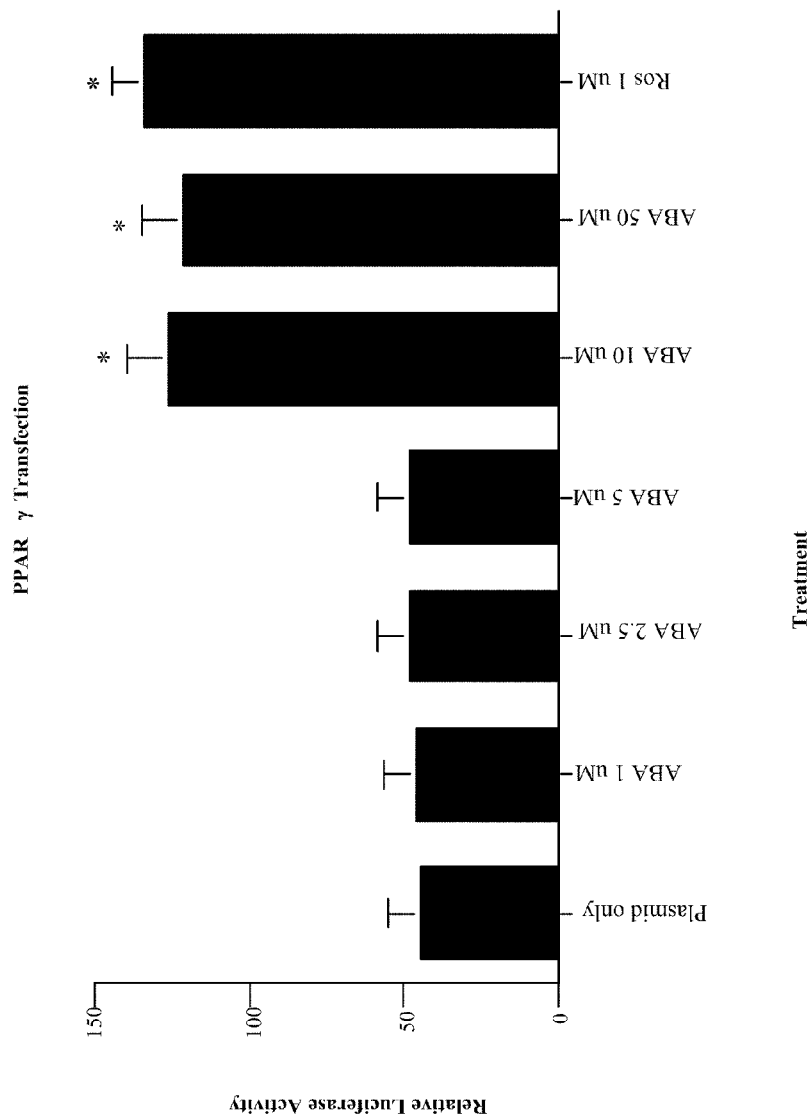
FIG. 2 is a chart showing a graph of the transactivation of peroxisome proliferator-activated receptor γ (PPAR γ) in 3T3-L1 pre-adipocytes cultured with abscisic acid (ABA) (0, 1, 2.5, 5, 10, 50 µM) or rosiglitazone (Ros) (1 µM). Relative luciferase activity (RLA) was calculated as the ratio of chemiluminescence 10 seconds before and after the reaction was stopped. Data are presented as average RLA±standard error. Data points with an asterisk are significantly different ($P<0.05$).

In order to establish whether ABA was a novel ligand of PPAR γ in vitro, we cultured increasing concentrations (1, 2.5, 5, 10, and 50 μM) of racemic ABA with 3T3-L1 pre-adipocytes that were transfected with a PPAR γ-Luciferase plasmid. In concurrence with our hypothesis, ABA significantly increased the relative luciferase activity of the transfected cells beginning at the 10 μM ABA concentration (FIG. 2). No additional increase in PPAR γ activity was observed with the 50 μM ABA concentration. Moreover, the PPAR γ activation obtained from 10 μM ABA was similar to that observed with 1 μM rosiglitazone, indicating that ABA is 10-fold less potent than the synthetic PPAR γ ligand in vitro.

Example 3

Dietary ABA Lowers Fasting Blood Glucose and Improves Glucose Tolerance

To confirm our in vitro findings suggesting that ABA is a novel PPAR γ ligand, we performed two separate in vivo experiments using prediabetic db/db mice. Experiment 1 was a dose-titration study, where we fed 4-week old db/db mice (n=25) diabetogenic, high fat diets containing either 0, 100, 200, 400, or 800 mg racemic ABA mixture/kg diet. Experiment 2 was designed as a replicate of experiment 1 in which db/db mice (n=14) were fed the most effective dose of ABA or a control diet. On day 36, mice fed the ABA-supplemented diets had significantly lower fasting blood glucose (FBG) concentrations, regardless of the amount of dietary ABA (i.e., 100 to 800 mg), than mice fed an isocaloric and isonitrogenous control diet without ABA (Table 2). These in vivo results are in agreement with the transfection findings showing no difference in PPAR γ transactivation between 10 and 50 μM ABA.

TABLE 2

Composition of Experimental Diets[1]

| Ingredient | Dietary Treatments | | | | |
|---|---|---|---|---|---|
| | Control | 100 mg ABA | 200 mg ABA | 400 mg ABA | 800 mg ABA |
| Casein | 232 | 232 | 232 | 232 | 232 |
| L-cystein | 3 | 3 | 3 | 3 | 3 |
| DL-Methionine. | 3.5 | 3.5 | 3.5 | 3.5 | 3.5 |
| Corn Starch | 137 | 137 | 137 | 137 | 137 |
| Maltodextrin | 150 | 150 | 150 | 150 | 150 |
| Sucrose | 162.595 | 162.595 | 162.595 | 162.595 | 162.595 |
| Cellulose | 50 | 50 | 50 | 50 | 50 |
| Cholesterol | 1.9 | 1.9 | 1.9 | 1.9 | 1.9 |
| Mineral Mix (AIN-93)[2] | 40.60 | 40.60 | 40.60 | 40.60 | 40.60 |
| Calcium phosphate dibasic | 4.64 | 4.64 | 4.64 | 4.64 | 4.64 |
| Vitamin Mix (AIN-93)[3] | 16.24 | 16.24 | 16.24 | 16.24 | 16.24 |
| Choline Bitartrate[4] | 5 | 5 | 5 | 5 | 5 |
| Tert-butylhydroquinone[5] | 0.02 | 0.02 | 0.02 | 0.02 | 0.02 |
| Vitamin K. phylloquinone | 0.005 | 0.005 | 0.005 | 0.005 | 0.005 |
| Soybean Oil | 30 | 30 | 30 | 30 | 30 |
| Lard | 163.5 | 163.5 | 163.5 | 163.5 | 163.5 |
| Abscisic Acid (ABA) | — | 0.100 | 0.200 | 0.400 | 0.800 |

*Provides approximately 19.6% fat, 0.2% total cholesterol and 4.4 kilocalories/g (kcal/g) it obtains 40% kcal from fat. Kcal density is approximately 16% higher than typical AIN-93G-based diets.
Supplied per kg of mineral mix: 357 g calcium carbonate. 196 potassium phosphate monobasic, 70.78 potassium citrate, 74 g sodium chloride, 46.6 g potassium sulfate, 24.3 g magnesium oxide. 6.06 g ferric citrate, 1.65 g zinc carbonate, 0.63 g magnesium carbonate. 0.31 g cupric carbonate. 0.01 g potassium Iodate, 0.01025 sodium selenate, 0.00795 ammonium paramolybdate. 1.45 g sodium-metasilicate, 0.275 chromium potassium sulfate. 0.0174 lithium chloride, 0.0815 boric acid, 0.0635 sodiumfluoride. 0.0318 nickel carbonate, hydroxide, tetrahydrate, 0.0066 ammonium vanadate, and 220.716 sucrose.
Supplied per kg of vitamin mix: 3 g nicolinic acid. 1.6 g calcium pentotenate, 0.7 g pyridoxine HCL 0.6 g thiamin HCL 0.6 g riboflavin, 0.2 g folic acid, 0.02 g D-biotin, 2.5 g vitamin $B_{12}$ (0.1% mannitol). 15 g DL-a tocopheryl acetate (500 IU/g). 0.8 g vitamin A palmitate (500,000 IU/g), 0.2 vitamin D, (cholecalciferol, 500,000 IU/g). 0.0075 vitamin K (phylloquinone). 974.705 g sucrose.
§ The choline bitartrate concentrations have been increased from 2.5 g/kg in regular AIN-93G diets to 5 g/kg due to increased kcal density of high fat diets.
[1] Antioxidant
[2] Mineral mix
[3] Vitamin mic
[4] Choline bitartrate
[5] tert-butylhydroquinone In order to test the ability of ABA to activate PPAR γ in vivo, we fed prediabetic db/db mice 0, 100, 200, 400, and 800 mg of a racemic ABA mixture/kg as part of a high-fat diet for 36 days. Mice consuming the ABA-supplemented diets had significantly lower fasting blood glucose levels and responded better to an IPGTT than mice fed the control diet. Moreover, all ABA-supplemented diets appeared to have a similar effect in improving glucose homeostasis, regardless of the amount of ABA from 100 to 800 mg. This finding agrees with in vitro findings which showed that 10 and 50 μM ABA induced similar PPAR γ transactivation. Commensurate with the enhancement in glucose tolerance, we found that the expression of PPAR γ and PPAR γ responsive genes adiponectin, CD36, and aP2 were significantly increased in WAT from db/db mice fed the ABA-supplemented diet. The increase in adiponectin production is significant in itself as it has been shown to promote insulin-stimulated glucose disposal in muscle (30), decrease hepatic glucose production (31), and increase the oxidation of intramuscular fatty acids (32). Consequently, it is possible that the some of the improvements in glucose homeostasis brought on by dietary ABA-supplementation are mediated by this important adipokine.

Figure 3:
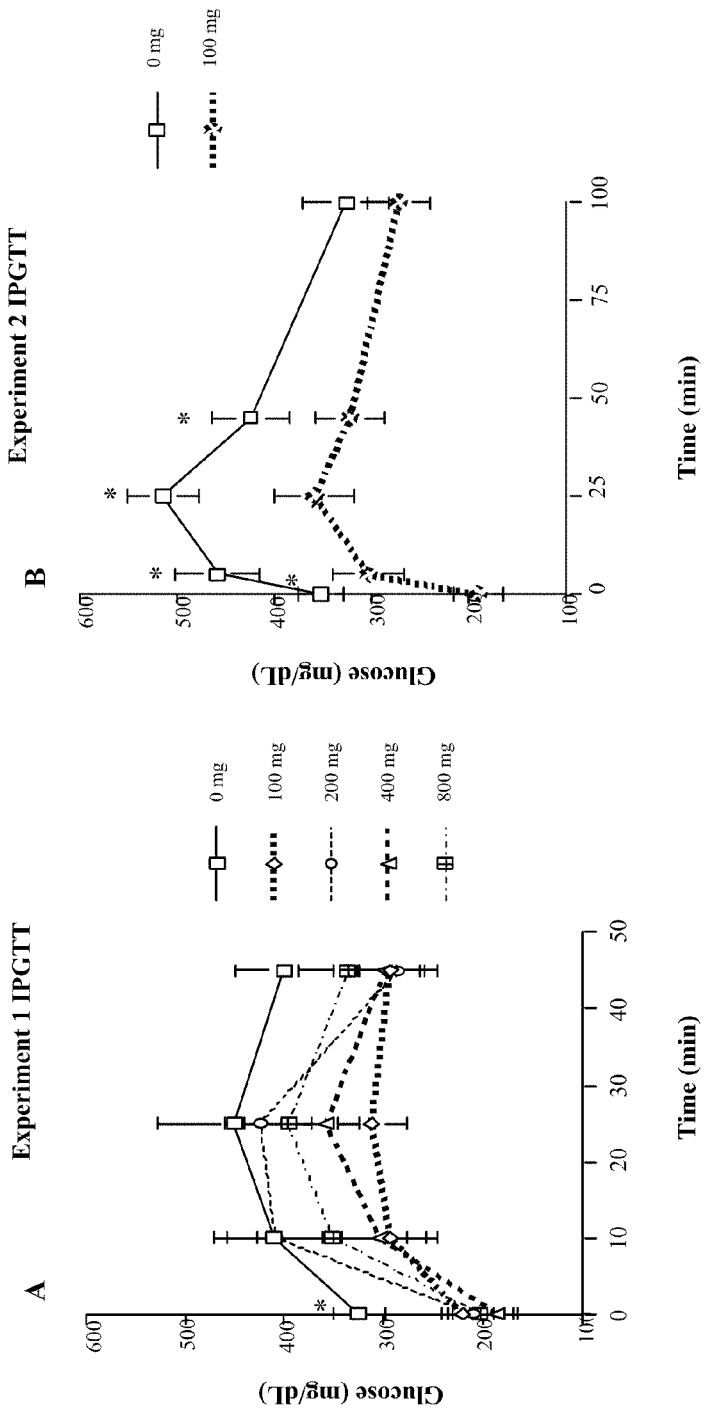
FIGS. 3A-B are graphics which show the effect of dietary abscisic acid (ABA) on response to an intraperitoneal glucose tolerance test (IPGTT) given after 36 days of dietary supplementation.

In addition to having lower FBG, mice fed ABA also had an improved response to the IPGTT on day 36 (FIG. 3). The 100 mg ABA/kg dose elicited the most favorable response in glucose homeostasis during the IPGTT (FIG. 3A). Based on these findings, however, in addition to the FBG readings showing no differences among the ABA diets from 100 to 800 mg/kg, we chose the 100 mg/kg dose of ABA to continue on with further experiments. The IPGTT at the end of Experiment 2 verified the positive glucose normalizing effects of ABA as glucose levels were significantly lower at every time point up to 100 minutes (FIG. 3B).

Example 4

Figure 4:
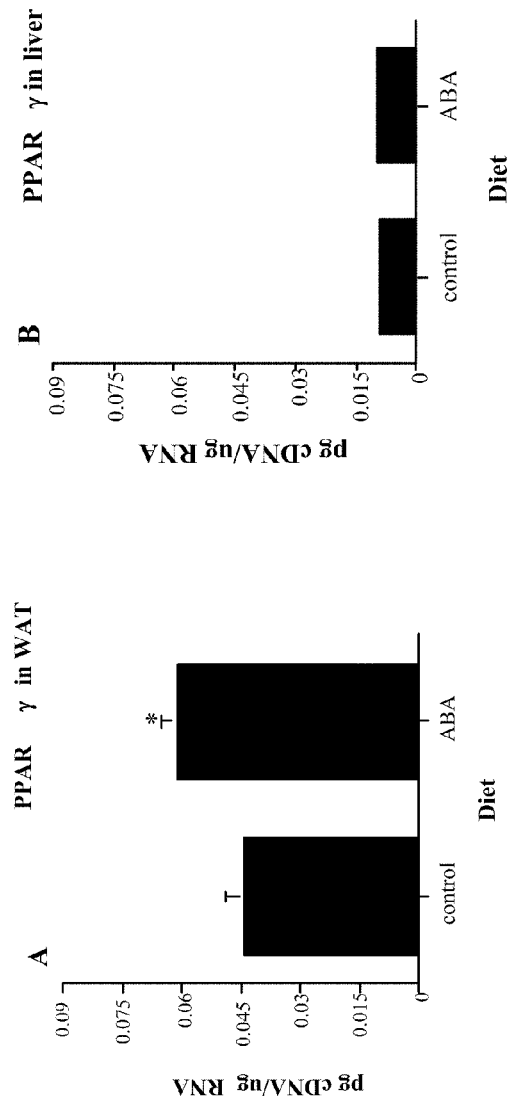
FIGS. 4A-D show graphs of the effect of dietary abscisic acid (ABA)-supplementation on mRNA expression of peroxisome proliferator-activated receptor γ (PPAR γ) and PPAR γ-responsive genes (Panel A—in white adipose tissue; Panel B—in liver; Panel C—in pancreas) adiponectin (Panel D), aP2 (Panel E), and CD36 (Panel F) in white adipose tissue. Expression of the house-keeping gene (β-actin) in both diets was approximately equal. Data are presented as least square means±standard error expressed as picograms (pg) of complementary DNA (cDNA) per microgram (µg) total RNA. An asterisk signifies that groups are significantly different ($P<0.05$).
Figure 4:
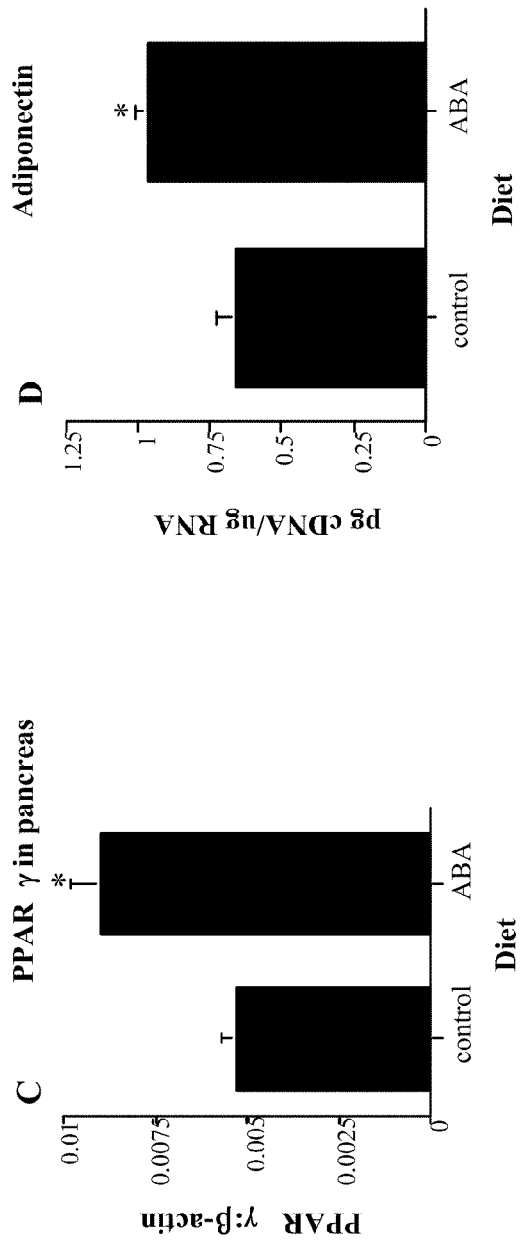
Figure 5:
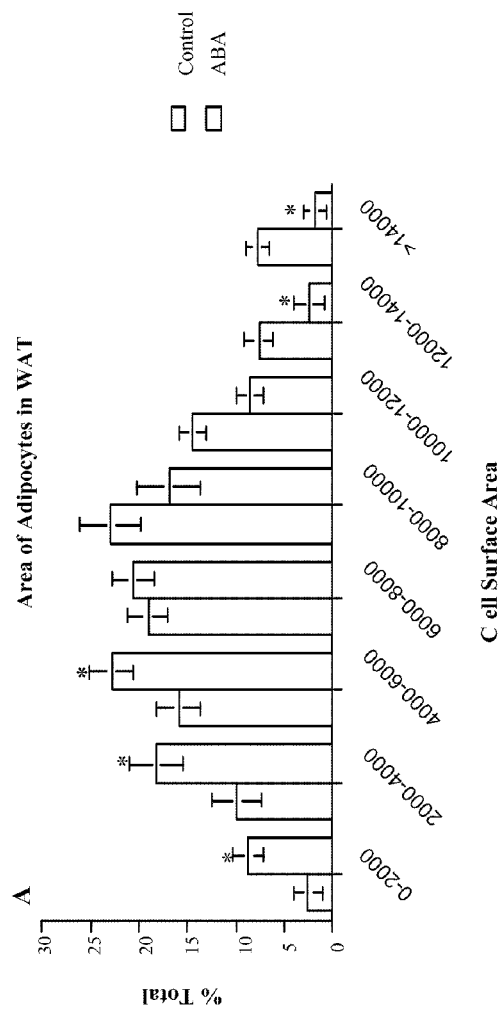
FIG. 5 shows plots demonstrating the effect of dietary abscisic acid (ABA)-supplementation on white adipose tissue (WAT) histology (A) Area of adipocytes (micrograms$^2$) was assessed using SigmaPro® 5.0 software. Representative photomicrographs of WAT from mice fed diabetogenic, high-fat diets, supplemented with either 0 (B) or 100 mg ABA/kg diet (C) at 100× magnification. Data are presented as least square means±standard error. An asterisk signifies that values are significantly different ($P<0.05$).
Figure 5:
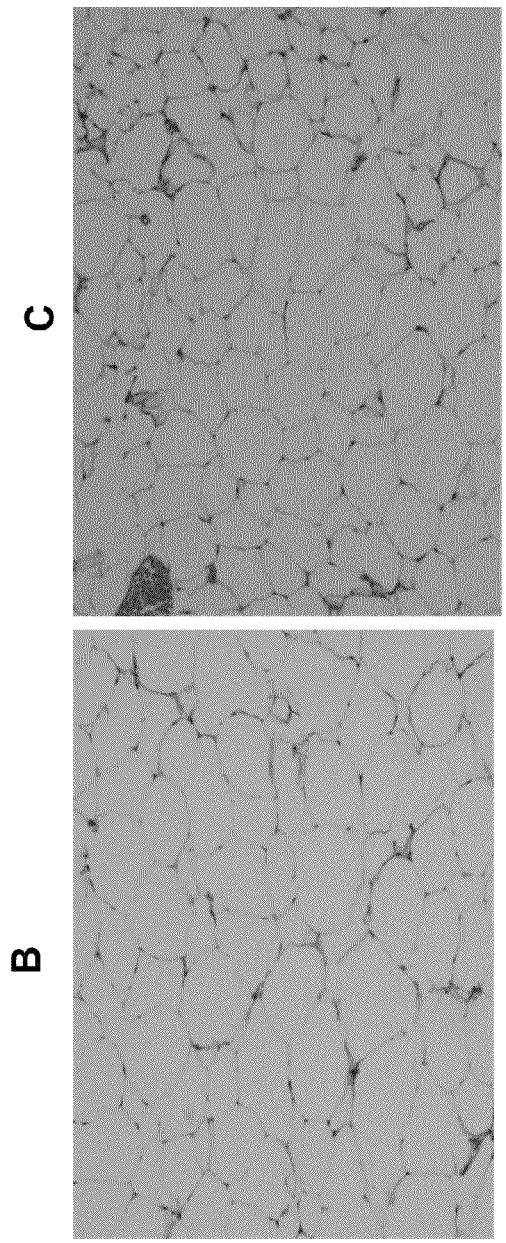
Figure 6:
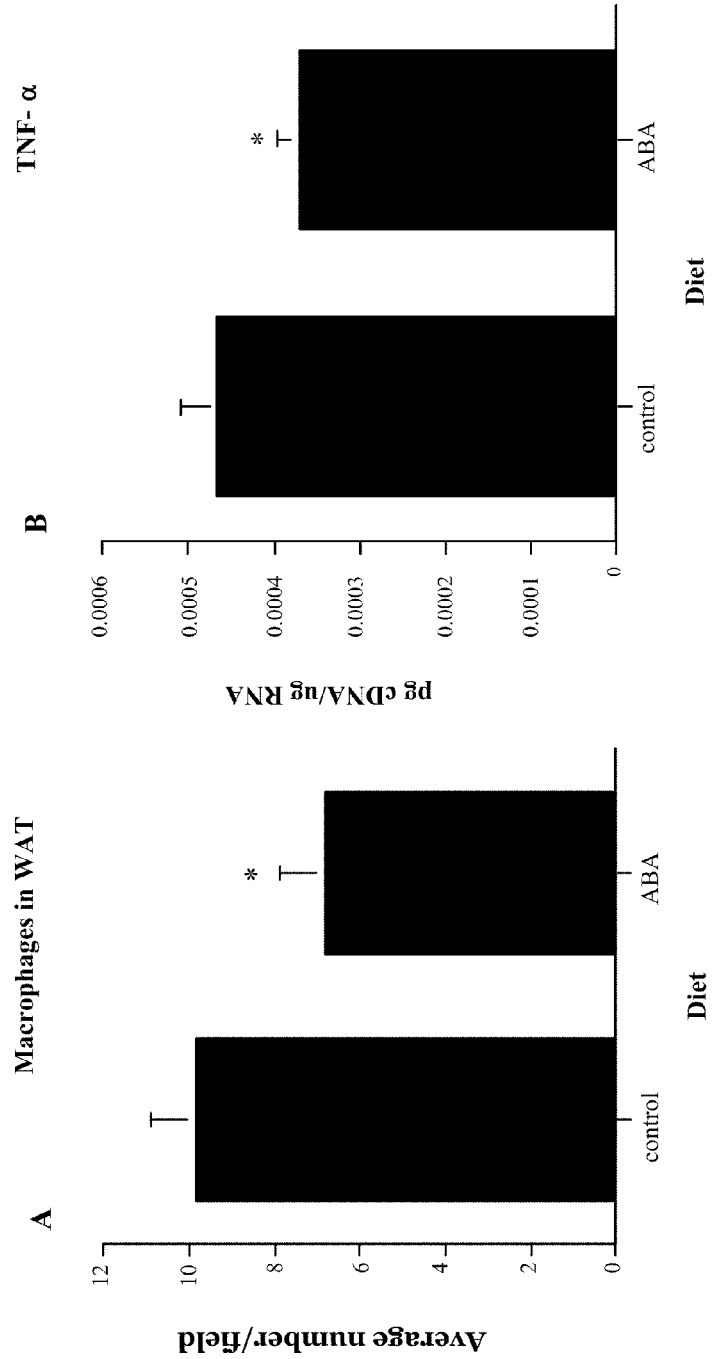
FIG. 6 shows plots demonstrating the effect of dietary abscisic acid (ABA)-supplementation on macrophage infiltration (Panel A) and tumor necrosis factor-α (TNF-α) (Panel B) expression in abdominal white adipose tissue (WAT) of db/db mice. Number of macrophages was obtained by averaging the results of 5 different fields at 400× magnification. Data are presented as least square means.+−.standard error. TNF-α is expressed as picograms (pg) of complementary DNA (cDNA) per microgram total RNA. An asterisk signifies that values are significantly different (P<0.05).

Dietary ABA-Supplementation Increased WAT PPAR γ and PPAR γ-Responsive Gene Expression and Reduced WAT Inflammation To determine whether the glucose normalizing effects of ABA were associated with activation of PPAR γ in WAT, we used quantitative real-time PCR to measure the expression of PPAR γ and PPAR γ-responsive genes in WAT of ABA- and control-fed mice. We found that dietary ABA-supplementation resulted in a significant increase in WAT expression of PPAR γ ($P<0.01$) and the PPAR γ responsive genes adiponectin ($P<0.05$), aP2 ($P<0.02$), and CD36 ($P<0.01$) (FIG. 4). There were no significant differences in mRNA expression of either PPAR a or PPAR .delta. (data not shown). Histological analysis confirmed that WAT from ABA-fed mice had significantly more small adipocytes and fewer hypertrophic adipocytes than WAT from control-fed mice (FIG. 5), which correlated with a significantly lower number of macrophages infiltrating WAT in ABA-fed mice in comparison to mice fed the control diet ($P<0.05$) (FIG. 6A). In line with the lower numbers of infiltrating macrophages, TNF-α mRNA expression was also down-regulated in WAT from ABA-fed mice ($P<0.05$) (FIG. 6B).

Another main effect of PPAR γ activation in WAT is the reduction in hypertrophic adipocytes, which are less insulin responsive and secrete more pro-inflammatory adipokines than normal-sized adipocytes (16, 18, 33). By promoting adipogenesis and adipocyte differentiation, TZDs create numerous smaller adipocytes which enhance the absorption of triglycerides, glucose, and free fatty acids from the bloodstream (18). These changes are also associated with a significant reduction in the expression of macrophage surface markers CD68, CD11, and F4/80 in WAT (17). The macrophages in stromal vascular fraction are main producers of WAT-derived TNF-α(16), which impairs insulin signaling by increasing serine phosphorylation of IRS-1 (15). Histological analysis of WAT revealed that mice receiving the ABA-supplemented diet had significantly more small adipocytes than control mice. This attenuation in adipocyte hypertrophy was associated with significant reductions in both macrophage infiltration and TNF-α expression.

Example 5

Dietary ABA-Supplementation Had No Effect on Body Weight, Feed Intake or WAT Weight A common side effect of synthetic PPAR γ agonists is increased body weight brought on by fluid retention (26). As expected, the db/db mice from both the control and ABA-fed groups gained a substantial amount of weight throughout the 36 day trial (Table 3).

TABLE 3

Effect of abscisic acid (ABA) on fasting glucose levels on day 36 of dietary supplementation.*, , *

| Diet (mgABA/kg) | Experiment 1 Fasting glucose (mg/dL) | Experiment 2 Fasting glucose (mg/dL) |
|---|---|---|
| 0 mg (control) | 326.7$^a$ | 353.1$^a$ |
| 100 mg | 219.6$^b$ | 190.7$^b$ |
| 200 mg | 210.2$^b$ | — |
| 400 mg | 185.6$^a$ | — |
| 800 mg | 202.0$^b$ | — |
| Pooled SEM | 21.60 | 22.89 |
| ANOVA P value | 0.0113 | 0.0005 |

*Least squares means values in a column with different superscripts are significantly different ($P < 0.05$).
**P-value of main effects of diet (D) during 36-day period. Data were analyzed as a completely randomized design.
***Pooled standard error of the mean However, as opposed to findings with TZDs, there were no significant differences in body weights between mice consuming ABA and control diet, including no differences in abdominal WAT. Interscapular BAT, however, was significantly increased in mice fed ABA. The mice in the ABA-supplemented diet finished the trial weighing approximately 2.2 grams less than the control mice (41.34 g vs 43.54 g), though none of the numerical differences in weigh data from any of the time-points were statistically significant. Total feed intake also did not differ significantly between treatment groups (data not shown).

TABLE 4

Effect of dietary abscisic acid (ABA)-supplementation on body organ weight.*, , *

| Diet | Initial body weight (g) | Final body weight (g) | WAT % Body Weight | Liver % Body Weight | BAT % Body Weight |
|---|---|---|---|---|---|
| control | 19.63 | 43.54 | 5.74 | 5.74 | 0.91 |
| ABA | 19.83 | 41.34 | 6.06 | 5.16**** | 1.37 |
| Pooled SEM$^o$ | 0.864 | 1.282 | 0.258 | 0.125 | 0.106 |
| ANOVA P value | 0.865 | 0.248 | 0.476 | 0.027 | 0.007 |

*Organs were excised and weighed on day 36 of experiment.
**Least squares means values in a column with an asterisk are significantly different ($P < 0.05$).
***P-value of main effects of diet during the 36 day period. Data were analyzed as a completely randomized design
****Pooled standard error of the mean While ABA and synthetic PPAR γ agonists (e.g., rosiglitazone) elicit similar effects on adipose tissue morphology, treatment with ABA did not induce any weight gain, a major adverse side effect associated with TZDs. Initially thought to be related to the increase in adipogenesis, it is now believed that that the main contributor to TZD-associated weight gain is increased fluid retention via the PPAR γ-dependent induction of the $Na^+$ transporter ENaC (26). Conditional knockout of PPAR γ in the renal collecting ducts prevents TZD-induced weight gain (26). Approximately 10-15% of patients using TZDs are forced to discontinue treatment due to edema, and the increase in extracellular volume from excess fluid retention also poses a major problem for individuals with preexisting congestive heart failure (34, 35). The lack of weight gain in our study suggests that fluid retention either does not occur or is very minimal in ABA-fed mice, and we suspect this may be due to the lower affinity of ABA for PPAR γ in comparison with TZDs. This hypothesis is supported by the lower potency of ABA when compared to rosiglitazone in 3T3-L1 cells. The significant increase in BAT may also have contributed to the slight, but insignificant, reduction in weight of ABA-fed mice when compared to controls. The finding that ABA increases BAT is consistent with previous publications which found that PPAR γ activation by synthetic agonists such as TZDs increases BAT differentiation (36).

Example 6

Dietary ABA-Supplementation Ameliorated Hepatic Steatosis

Figure 7:
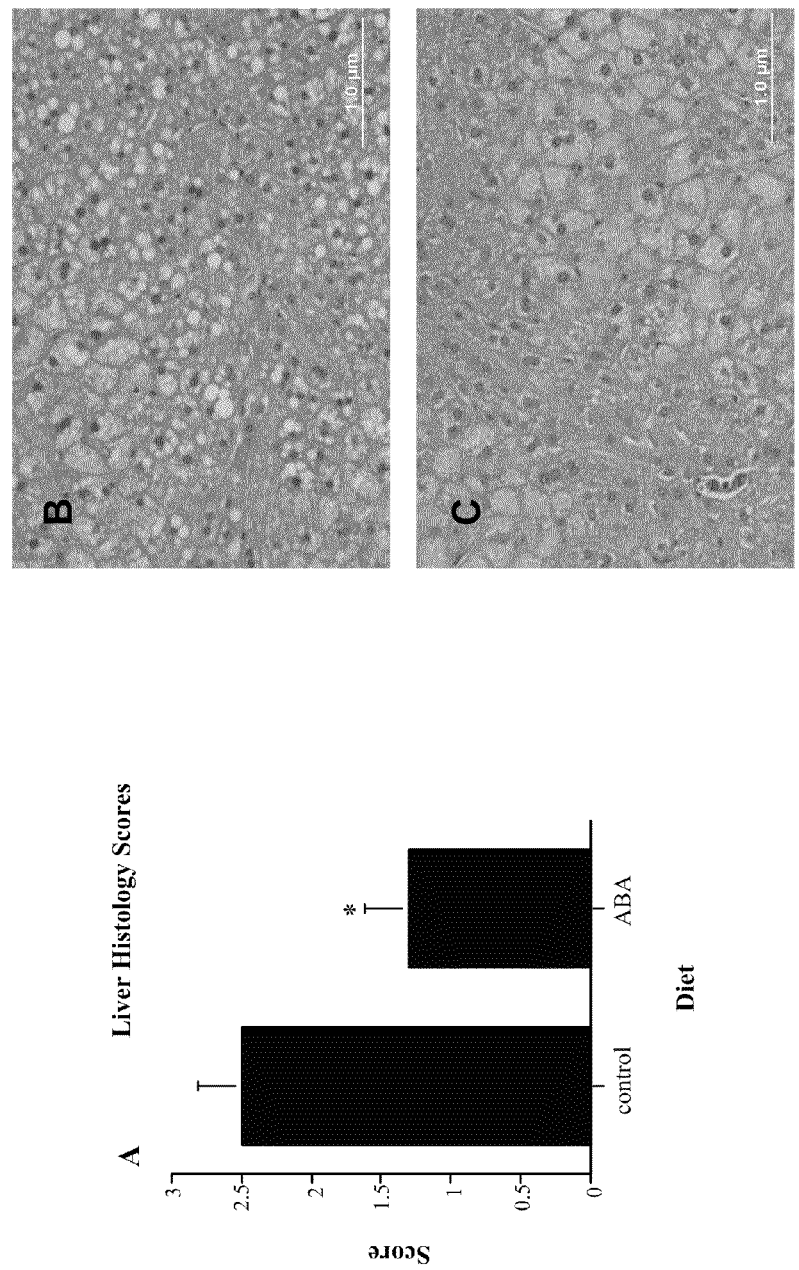
FIG. 7 is a bar graph which shows liver histology scores for treatment with ABA (Panel A), and staining of liver cells (Panels B and C).

To determine whether ABA had any hepatotoxic effects, we first determined whether there were any significant differences in liver sizes between the ABA and control-fed mice on day 36. We found that the livers from ABA-fed mice were significantly smaller than those from the controls ($P<0.03$). H&E-stained hepatic sections were then examined histologically at 400× magnification to assess lipodystrophy by using the NASH scoring method. We determined that hepatic steatosis was significantly mitigated in db/db mice that consumed ABA ($P<0.02$) (see FIGS. 7A and 7B).

Due to the hepatotoxic effects of TZDs, we determined whether dietary ABA-supplementation had any effect on liver morphology. We demonstrated that the livers of ABA-supplemented mice were significantly smaller than those from the controls. On closer examination, we found that hepatocytes from ABA-fed mice had significantly reduced lipid accumulation. This finding is contrary to results one would expect to observe with synthetic PPAR γ agonists, since rosiglitazone treatment has been shown to exacerbate hepatic steatosis by inducing de novo lipogenesis (37) and troglitazone was withdrawn from the market by the FDA due to reports of severe liver injury or death. We believe that the different effects of TZDs and ABA on hepatic steatosis are due to ABA's weaker affinity for PPAR γ combined with adiponectin secretion from WAT. It has been demonstrated that treatment of obese mice with adiponectin ameliorates hepatic steatosis by reducing fatty acid synthesis and uptake while increasing fatty acid oxidation (38). Because production of adiponectin mRNA was increased in WAT following ABA treatment, this adipokine may have played a role in the improving hepatic health.

Example 7

Dietary ABA-Supplementation Decreased CD4+ and CD8+ T Cell Proliferation Ex Vivo Isolation of Lymphocytes and Cell Culture Conditions Single cell suspensions were prepared from the spleen by gently crushing the spleens excised during the necropsy procedure between the frosted ends of microscope glass slides previously autoclaved. Tissue debris were removed by settling, erythrocytes were eliminated by hypotonic lysis and cells finally resuspended in complete RPMI (cRPMI, 10% fetal bovine serum (Hyclone, Logan, Utah), 25 mM HEPES buffer (Sigma, St. Louis, Mo.), 100 units/ml penicillin (Sigma), 0.1 m/ml streptomycin (Sigma), 1 mM sodium pyruvate (Sigma), 1 mM nonessential aminoacids (Sigma), and 2 mM essential amino acids (Mediatech), and enumerated with a Coulter Z1 Single Particle Counter (Beckman Coulter, Miami, Fla.).

Lymphocyte Blastogenesis Test

Wells of 96-well, round bottom microtiter plates were seeded with $2\times10^5$ splenocytes in a total volume of 200 ml per well. Cells were cultured in cRPMI media with or without 2.5 μg/ml of Concanavalin A (Sigma) for 4 days. On day 4, 0.5 mCi of methyl-[$^3$Thymidine] was added to each well, and cells we incubate for 20 additional hours. Well contents were harvested onto glass fiber filters using cell harvester, and incorporated radioactivity measured by liquid scintillation counting. Samples were run in triplicate for each animal and ex-vivo treatment. Stimulation indices were calculated by dividing counts per minute of mitogen-stimulated wells by counts per minute of unstimulated wells.

Carboxy-Fluorescein Diacetate Succinidimyl Ester

A total of $30\times10^6$ splenocytes were labeled with the green fluorescent dye carboxy-fluorescein diacetate succinidimyl ester (CFSE) (Molecular Probes) following manufacturer's instructions. Briefly, cells were aliquoted into 15 ml polystyrene conical tubes and centrifuged at 400×g for 5 min. After eliminating the supernatant, cells were resuspended in 1 ml of RPMI 1640 with 2 mM CFSE. Cells were incubated with the dye for 7 min at room temperature and the reaction was stopped by the addition of 9 ml of RPMI. To eliminate excess CFSE, cells were washed 2 times in RPMI 1640 and finally resuspended in complete RPMI.

Splenocytes at $10^6$ cells/ml were seeded in 96-well, round-bottom microtiter plates and incubated incomplete RPMI with or without Concanavalin A (Sigma) at 2.5 μg/ml. After 5 days in culture, cells were harvested and labeled for the analysis cell surface marker expression by flow cytometry. Cell surface staining was conducted by incubating cells in 100 ml of combined biotinylated rat anti mouse CD4 (clone) and phycoerithrin labeled rat anti-mouse CD8α (clone) diluted in FACS buffer (PBS containing 5% of fetal bovine serum (Hyclone) and 0.01% of sodium azide (Sigma)) for 20 min at 4° C. Following 2 washes in Fluorescence activated cell sorting (FACS) buffer, cells were incubated with streptavidin-PeCy5 (Pharmingen, San Diego, Calif.) for the biotinylated anti-mouse CD4 antibody. Cells were analyzed by 3-color flow cytometry (CFSE, phycoerythrin and PeCy5) in a FACScalibur instrument (Becton Dickinson). Ten thousand events were acquired, and data were analyzed using the Cell Quest Pro™ software (Becton Dickinson). Proliferation was assessed by the decrease in fluorescent intensity of CFSE staining. A Relative Proliferation Index was calculated by dividing the percentage of, $CD4^+$ or $CD8\alpha$ cells that proliferated in Concanavalin A-stimulated cultures by the percentage of $CD4^+$ or $CD8\alpha$ cells that proliferated in cultures maintained with media alone.

ABA Modulates the Proliferation of CD4+ and CD8+ T-Cells

Evidence has shown that PPAR γ agonists inhibit T-cell proliferation by blocking the production of interleukin-2 (IL-2) (Yang et al. J. Biol. Chem. 2000). To determine if ABA had any effect on T-lymphocyte proliferation, we performed two different proliferation assays, flow cytometry and LBT. Our results from flow cytometry show that after the first generations, both CD4+ and CD8+ concanavalin A-induced proliferation significantly decreases in the ABA supplemented diet. This finding is supported by the numerical differences in the LBT data, which measures total lymphocyte proliferation for only the last generations (Table 5).

These results are consistent with recent findings showing that proliferation induced by anti-CD3, another polyclonal stimulator of T cell proliferation, was decreased in lymphocytes derived from the spleen of ABA-fed mice (stimulation index 30.12 in controls versus 8.55 in ABA-fed mice). However, proliferation of mesenteric lymph node-derived lymphocytes was augmented 10-fold following ABA feeding and prostaglandin E2 (PGE2) production was decreased by ABA. While polyclonal stimulation of T cells (mitogen- or anti-CD3-induced stimulation) is generally detrimental and it can be associated with the onset of autoimmune and allergic responses, discreet antigen-specific responses to pathogens are beneficial and contribute to resistance against infectious diseases. We next measured the ability of ABA to modulate antigen-specific responses to influenza virus antigens following immunization with an inactivated influenza virus vaccine. We found that ABA maintained or enhanced the ability of T cells to proliferate in response to influenza virus antigens (stimulation index 4.86 in controls versus 8.61 in ABA-fed mice). This enhanced proliferative ability was associated with increased production of interleukin-2 (IL-2) in ABA-fed mice (5 vs 31.67 picograms IL-2/ml of cell supernatant).

TABLE 5

Lymphocyte Proliferation Assays[1,2,3]

| Diet | Flow Cytometry | | | | LBT Total |
|---|---|---|---|---|---|
| | CD4+ T cells | | CD8+ T cells | | lymphocytes |
| (mgABA/kg) | RPI1 | RPI2 | RPI1 | RPI2 | SI |
| 0 | 12.43 | 47.55* | 3.086 | 212.01* | 21.36 |
| 100 | 17.72 | 30.56 | 5.261* | 63.26 | 9.22 |
| Pooled SEM[4] | 4.26 | 2.87 | 0.53 | 13.19 | 7.08 |
| ANOVA P value | 0.38 | 0.0019 | 0.015 | 0.0002 | 0.25 |

[1]Flow cytometry and LBT were perfurmed to assess lymphocyte proliferation. RPI (relative proliferation index) I is the proliferation of the first 2 generations of CD4 and first 4 generations of CD8 cells. RPI2 is a measure of the last 3 and 4 generations of CD4 and CD8 T-cells, respectively. The stimulation index (SI) is an assessment of total T lymphocy to proliferation during the LBT assay.
[2]Least squanes means values in a column with an astevisk are significantly differens (P < 0.05).
[3]P-value of main effects of diet (D) during 36 day period. Date were analyzed as a completely rendomized design.
[4]Pooled standerd error of the mean.

Example 8

Effect of ABA on Skeletal Muscle Inflammation

Recent evidence has indicated that obesity-induced insulin resistance (IR) is associated with white adipose tissue (WAT) macrophage infiltration and inflammation. We fed either control or abscisic acid (ABA)-supplemented high-fat diets to db/db and lean C57BL6/J mice for 36 days and measured fasting blood glucose levels. Flow cytometry was utilized to assess the macrophage infiltration, including those expressing chemokine receptors 2 and 5 (CCR2 and CCR5), in abdominal WAT and SM. Tumor necrosis factor α (TNF-α) and monocyte chemoattractant protein-1 (MCP-1) expression in both tissues was quantified by real time qRT-PCR. Dietary ABA-supplementation significantly decreased CCR2' and CCR5' macrophage infiltration into WAT. In SM, ABA attenuated hypertrophy of intermuscular adipose tissue (IMAT). MCP-1 expression in stromal vascular cells (SVCs) and SM was significantly downregulated in ABA-fed mice. This example shows that obesity-induced IR is significantly associated with SM inflammation and that PPAR γ ligands can improve insulin sensitivity by inhibiting SM inflammation.

For this Example, the following materials and methods were used:

Mice and dietary treatments. Six to eight week-old BKS.Cg-+$Lepr^{db}$/+$Lepr^{db}$/OlaHsd (db/db) mice and their lean littermates were housed at the animal facilities at Virginia Polytechnic Institute and State University in a room maintained at 75° F., with a 12:12 h light-dark cycle starting from 6:00 AM. All experimental procedures were approved by the Institutional Animal Care and Use Committee of Virginia Polytechnic Institute and State University and met or exceeded requirements of the Public Health Service/National Institutes of Health and the Animal Welfare Act.

Mice (n=17) were fed high-fat diets containing 0 or 100 mg of racemic ABA (Sigma Aldrich, St. Louis, Miss.)/kg diet for 36 days. On day 36, fasted mice (12 h) were sacrificed by $CO_2$ narcosis and blood was withdrawn directly through the heart for assessment of fasting glucose levels with an Accu-Chek (R) Glucometer (Roche, Indianapolis, Ind.). Abdominal WAT and skeletal muscle from the left hind limb (gastrocnemius, plantaris, and soleus) were then excised to generate single cell suspensions for flow cytometry. SM from the right hind limb were also placed in 10% buffered neutral formalin for histological evaluation and stored in RNA later (Ambion, Austin, Tex.), a commercial solution that inhibits RNases.

WAT Digestion. Abdominal WAT was excised, weighed, minced into small <10 mg pieces and placed into digestion media consisting of DMEM (Mediatech, Herndon, Va.) supplemented with 2.5% HEPES (Mediatech) and 10 mg/ml fatty-acid poor bovine serum albumin (FAB-poor BSA, Sigma), Liberase Blendzyme 3 (0.03 mg/ml, Roche) and DNase 1 (50 U/ml, Qiagen, Valencia, Calif.). Samples were incubated in a rotating 37° C. water bath for 90 minutes and then filtered through a 250 μm nylon mesh (Sefar America Inc., Depew, N.Y.) to remove undigested particles and centrifuged at 4° C. at 2235 rpm for 10 minutes. The floating portion (adipocyte-rich portion), was then removed and digested for an addition 60 minutes at 37° C. The pellet, consisting of stromal vascular cells (SVCs), was washed with DMEM and centrifuged at 4° C. at 2235 rpm for 10 minutes. The supernatant was discarded and erythrocytes were lysed by incubating the SVCs in 2 ml erythrocyte lysis buffer for 2 minutes before stopping the reaction with 9 ml 1×PBS. Cells were then centrifuged again at 4° C. at 2235 rpm for 10 minutes, suspended in 1 ml of 1×PBS, and enumerated with a Z1 Single Particle Counter (Beckman Coulter, Fullerton, Calif.). The SVCs were resuspended in FACS buffer at a concentration of 2×10$^6$ cells/ml. The cells not used in the resuspensions were centrifuged for 5 minutes at 13,000 rpm, resuspended in RLT lysis buffer (Qiagen) containing 1%13-mercaptoethanol, and immediately frozen at −80° C. for RNA isolation and gene expression analyses.

Quantitative real-time reverse transcriptase PCR. Total RNA was isolated from SVCs and SM using the RNA isolation Minikit (Qiagen) according to the manufacturer's instructions. Total RNA (1 µg) was used to generate complementary DNA (cDNA) template using the iScript cDNA Synthesis Kit (Bio-Rad, Hercules, Calif.). The total reaction volume was 20 µl with the reaction incubated as follows in an MJ MiniCycler: 5 minutes at 25° C., 30 minutes at 52° C., 5 minutes at 85° C., hold at 4° C. PCR was performed on the cDNA using Taq DNA polymerase obtained from Invitrogen and using standard conditions. Each gene amplicon was purified with the MiniElute PCR Purification Kit (Qiagen) and quantitated on an agarose gel by using a DNA mass ladder (Promega). These purified amplicons were used to optimize real-time PCR conditions and to generate standard curves in the real-time PCR assay. Primer concentrations and annealing temperatures were optimized for the iCycler iQ system (Bio-Rad) for each set of primers using the system's gradient protocol. PCR efficiencies were maintained between 92 and 105% and correlation coefficients above 0.98 for each primer set (Table 6) during optimization and also during the real-time PCR of sample DNA.

TABLE 6

Oligonucleotide sequences for quantitative real-time PCR[1,2]

| Primer | Sequence | Length | Acc. No. | SEQ ID NO. |
|---|---|---|---|---|
| β-actinF | 5'CCCAGGCATTGCTGACAGG3' | 141 | X03672 | 17 |
| β-actinR | 5'TGGAAGGTGGACAGTGAGGC3' | | | 18 |
| TNF-αF | 5'ACTGCCAGAAGAGGCACTCC3' | 137 | NM_013693 | 19 |
| TNF-αR | 5'CGATCACCCCGAAGTTCA3' | | | 20 |
| MCP-1F | 5'CTTGCCTAATCCACAGACTG'3 | 146 | AJ238892 | 21 |
| MCP-1R | 5'GCCTGAACAGCACCACTA'3 | | | 22 |

[1]F, forward; R, reverse. PCR primer pairs were designed for 78 and 157 base pairs. Annealing temperatures are 57° C. for β-actin and TNF-α 54° C. for MCP-1, and 51.9° C. for MIP-1α
[2]When plotting threshold cycle versus log starting quantity (pg), standard curves had slopes between −3.1 and −3.7; PCR efficiencies between 92 and 105 and R$^2$ above 0.98.

Complementary DNA (cDNA) concentrations for genes of interest were examined by real-time quantitative PCR using an iCycler IQ System and the iQ SYBR green supermix (BioRad). A standard curve was generated for each gene using 10-fold dilutions of purified amplicons starting at 5 pg of cDNA and used later to calculate the starting amount of target cDNA in the unknowns. SYBR green I is a general double-stranded DNA intercalating dye and, therefore, might detect nonspecific products and primer/dimers in addition to the amplicon of interest. In order to determine the number of products synthesized during the real-time PCR, a melting curve analysis was performed on each product. Real-time PCR was used to measure the starting amount of nucleic acid of each unknown sample of cDNA on the same 96-well plate. Results are presented as starting quantity of target cDNA (picograms) per microgram of total RNA.

Histopathology. SM specimens were fixed in 10% phosphate buffered neutral formalin, embedded in paraffin, cut at thicknesses of 5 microns and later stained with hematoxylin and eosin (H&E) for histological examination of IMAT. The average area of adipocytes in IMAT was calculated using Image Pro Plus® software at a magnification of 100×.

Statistical Analyses. Data were analyzed as a completely randomized design. To determine the statistical significance of the model, analysis of variance (ANOVA) was performed using the general linear model procedure of Statistical Analysis Software (SAS). A probability value (P)<0.05 was considered to be significant. When the model was significant, ANOVA was followed by Sheffe's multiple comparison method. Non-parametric data were analyzed by using the Mann-Whitney U test followed by a Dunn's multiple comparison's test. Correlations between macrophage infiltration and fasting blood glucose levels were assessed with Pearson's Correlation Coefficient.

Results

Adipocyte Hypertrophy in Intermuscular Adipose Tissue

Figure 8:
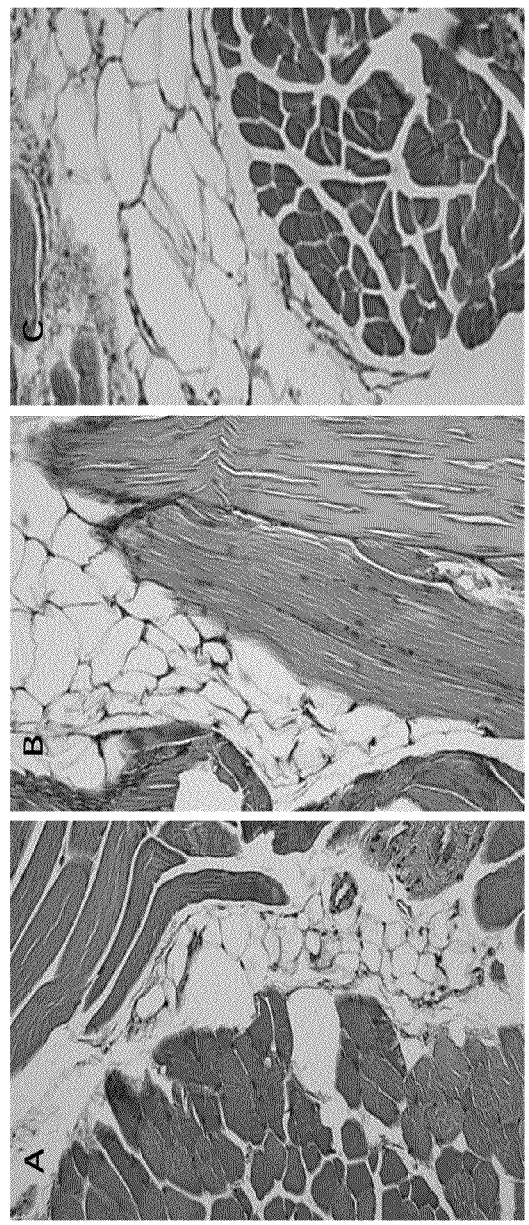
FIG. 8, Panels A-C, show images of intramuscular adipose tissue (also called infiltrating adipose tissue) and the presence of macrophages.

Data obtained and presented as part of this invention support the conclusion that SM inflammation, brought on by adipocyte hypertrophy and macrophage infiltration in IMAT, contributes significantly to the systemic insulin resistance induced by obesity. Following histological examination of SM specimens from control-fed obese and lean mice, one of our initial observations was that adipocytes in IMAT were extremely large. We also observed that IMAT in the db/db mice, regardless of diet, was significantly more hypertrophic than the lean mice (FIG. 8, Panels A-D). More specifically, FIG. 8 illustrates the effect of obesity on adipocyte hypertrophy in intermuscular adipose tissue (IMAT). Db/db and lean C57BL6/J mice were fed high-fat control diets or one supplemented with abscisic acid (ABA, 100 mg/kg diet) for 36 days. Illustrated in FIG. 8 are representative photomicrographs of IMAT in (Panel A) control-fed lean, (Panel B) ABA-supplemented db/db, and (Panel C) control-fed db/db mice taken at 100× magnification. Average adipocyte areas (Panel D) were calculated using ImagePro Plus® software. Data are presented as least square means±standard error. Data points with different subscripts are significantly different (P<0.05).

We have previously demonstrated that dietary ABA-supplementation significantly attenuates adipocyte hypertrophy in abdominal WAT of db/db mice. In similar regard, IMAT hypertrophy was also significantly attenuated as a result of ABA-supplementation.

Skeletal Muscle Inflammation

Db/db mice were fed either a control high-fat diet or one supplemented with 100 mg/kg all racemic abscisic acid (ABA). Real-time qRT-PCR was utilized to assess mRNA expression of tumor necrosis-α (TNF-α), monocyte chemoattractant protein-1 (MCP-1) in SM.

We next measured TNF-α expression in SM and observed that TNF-α was approximately 2-fold higher in control-fed db/db mice when compared to ABA-fed db/db mice (P=0.03) and control-fed lean mice (P=0.03).

Example 9

Further Characterization of the Role of ABA in PPAR γ Activity

Obesity is associated to a low-grade chronic inflammation characterized by macrophage infiltration into white adipose tissue (WAT). However, the phenotype of adipose tissue macrophage (ATM) subsets, and the mechanisms by which insulin-sensitizing compounds modulate subset-specific macrophage infiltration remain unknown. In the following set of experiments, we used a loss-of-function approach to investigate whether the peroxisome proliferator-activated receptor (PPAR) γ agonist, abscisic acid (ABA), ameliorates insulin resistance through a mechanism dependent on immune cell PPAR γ. We characterized two phenotypically distinct ATM subsets in db/db mice based on the amount of F4/80 and chemokine receptors (CCR) expressed on their surfaces. The F4/80$^{hi}$ macrophages were more abundant in WAT and expressed greater surface concentrations of chemokine receptor 2 (CCR2) and CCR5 when compared to F4/80$^{lo}$ macrophages. ABA significantly decreased CCR2+F4/80$^{hi}$ macrophage infiltration into WAT and suppressed monocyte chemoattractant protein-I (MCP-1) expression in WAT and plasma. Furthermore, it decreased MCP-1 promoter activity in 3T3-L1 cells. The deficiency of PPAR γ in immune cells, including macrophages, impaired the ability of ABA to suppress infiltration of F4/80$^{hi}$ macrophages into WAT, repress WAT MCP-1 mRNA expression and improve glucose tolerance. We provide in vivo molecular evidence that ABA improves insulin sensitivity and obesity-related inflammation by inhibiting MCP-1 expression and F4/80$^{h1}$ ATM infiltration through a PPAR γ-dependent mechanism.

To further characterize the findings discussed above, the study discussed below aimed to dissect the expression of PPAR γ-responsive and inflammatory genes by adipocytes versus stromal vascular cells (SVC)s in WAT. We also phenotypically characterized the subsets of adipose tissue macrophages (ATM) targeted by ABA and determine whether ABA ameliorates insulin resistance and obesity-related inflammation through a mechanism dependent upon immune cell PPAR γ. Our data demonstrate that SVCs, and not the adipocytes, are the main producers of PPAR γ-responsive genes and chemokines in WAT. In addition, we provide in vivo molecular evidence suggesting that ABA ameliorates glucose tolerance and obesity-related inflammation by suppressing MCP-1 expression and F4/80$^{hi}$ macrophage infiltration into WAT through a mechanism dependent on immune cell PPAR γ.

Materials and Methods

Mice and Dietary Treatments

BKS.Cg-+Leprdb/+Leprdb/OlaHsd (db/db), PPAR Yflfl; MMTV-Cre$^+$ and PPAR γ flfl; MMTV-Cre$^-$ mice in a C57BL16J background were housed at the animal facilities at Virginia Polytechnic Institute and State University in a room maintained at 22° C., with a 12:12 h light:dark cycle starting from 6:00 AM. All experimental procedures were approved by the Institutional Animal Care and Use Committee of Virginia Polytechnic Institute and State University and met or exceeded requirements of the Public Health Service National Institutes of Health and the Animal Welfare Act.

Db/db mice (n=10) were fed high-fat diets with a previously described ingredient composition (48) containing 0 or 100 mg of racemic ABA (Sigma Aldrich, St. Louis, Miss.)/kg diet for 36 days. On day 36, fasted mice (12 h) were sacrificed by $CO_2$ narcosis and blood was withdrawn directly from the heart for assessment of fasting glucose levels with an Accu-Chek® Glucometer (Roche, Indianapolis, Ind.). Plasma was also collected for analysis of MCP-1 protein levels and plasma triglycerides (TGs). Abdominal WAT was then excised to generate single cell suspensions for flow cytometry. Liver specimens were placed in 10% buffered neutral formalin for histological evaluation. Liver samples were also stored in RNA later (Ambion, Austin, Tex.), a commercial solution that inhibits RNases, for RNA isolation and quantitative gene expression analyses. PPAR γ foxed mice expressing the Cre transgene (e.g., PPAR-y fl/fl; MMTV-Cre) undergo premature termination of translation following the loss of the exon 2 of PPAR γ due to the enzymatic activity of the recombinase on genomic DNA (49, 50). PPAR Yflfl; MMTV-Cre$^+$ and PPAR γ flfl; MMTV-Cre$^-$ littermate mice were fed high-fat diets with or without ABA (100 mg/kg). After 28 weeks, the mice were fasted for 6 hours and bled through the caudal vein for assessment of fasting blood glucose concentrations by using an Accu-Chek® Glucometer (Roche, Indianapolis, Ind.). The mice were then subjected to an intraperitoneal glucose tolerance test (2 g/kg body weight), with determination of glucose levels at 15, 30, and 90 minutes post-challenge. At the 90 minute timepoint, mice were sacrificed by $CO_2$ narcosis. Abdominal WAT was then excised to generate single-cell suspensions for flow cytometry or placed in 10% buffered neutral formalin for histological evaluation and stored in RNA later (Ambion, Austin, Tex.) for RNA isolation and quantitative gene expression analyses.

WAT Digestion

Abdominal WAT was excised, weighed, minced into small <10 mg pieces and placed into digestion media consisting of DMEM (Mediatech, Herndon, Va.) supplemented with 2.5% HEPES (Mediatech) and 10 mg/ml fatty-acid free bovine serum albumin (FAB-poor BSA, Sigma), Liberase Blendzyme 3 (0.03 mg/ml, Roche) and DNase I (50 D/ml, Qiagen, Valencia, Calif.). Samples were incubated in a rotating 37° C. water bath for 90 minutes and then filtered through a 250 µm nylon mesh (Sefar America Inc., Depew, N.Y.) to remove undigested particles and centrifuged at 4° C. at 1,000×g for 10 minutes. The pellet, consisting of stromal vascular cells (SVCs), containing endothelial cells, pre-adipocytes, macrophages and T cells, was washed with DMEM and centrifuged at 4° C. at 1,000×g for 10 minutes. The supernatant was discarded and erythrocytes were lysed by incubating the SVCs in 2 ml erythrocyte lysis buffer for 2 minutes before stopping the reaction with 9 ml 1× phosphate-buffered saline (PBS). Cells were then centrifuged again at 4° C. at 1,000×g for 10 minutes, suspended in 1 ml of 1×PBS, and enumerated with a Z1 Single Particle Counter (Beckman Coulter, Fullerton, Calif.). The SVCs were resuspended in FACS buffer (1×PBS, 1% normal goat serum, 0.2% sodium azide) at a concentration of $2 \times 10^6$ cells/ml. The SVCs not used in the resuspensions were centrifuged for 5 minutes at 10,000×g, resuspended in RLT lysis buffer (Qiagen) containing 1% mercaptoethanol, and immediately frozen at −80° C. for RNA isolation and gene expression analyses.

Flow Cytometry

SVCs (2×105 cells) were seeded into 96-well plates and centrifuged at 4° C. at 1,800×g for 4 minutes. The cells were then incubated in the dark at 4° C. for 20 minutes in FcBlock (20 µg/ml; BD Pharmingen), and then for an additional 20 minutes with fluorochrome-conjugated primary antibodies anti-F4/S0-PE-Cy5 (5 µg/ml), anti-CD11b-FITC (2 µg/ml) (eBioscience), anti-CCR5-PE or anti-CCR2-PE (R&D systems, Minneapolis, Minn.). The specific antibody combinations used were F4/80, CD11b, CCR5 and F4/80, CD11b, CCR2. After incubation with primary antibodies, cells were centrifuged at 4° C. at 1,800×g for 4 minutes and washed with 200 µl of FACS buffer. After washing, cells were suspended in 200 µl PBS and 3-color data acquisition was performed on a FACS Calibur flow cytometer. Data analyses were performed by using the CellQuest software (BD).

Quantitative Real-Time Reverse Transcriptase PCR

Total RNA was isolated from SVCs and liver using the RNA isolation Minikit (Qiagen) according to the manufacturer's instructions. RNA from the adipocyte fraction and WAT was isolated using the Lipid Minikit (Qiagen). Total RNA (1 µg) was used to generate complementary DNA (cDNA) template using the iScript cDNA Synthesis Kit (Bio-Rad, Hercules, Calif.). The total reaction volume was 20 µl with the reaction incubated as follows in an MJ MiniCycler: 5 minutes at 25° C., 30 minutes at 52° C., 5 minutes at 85° C., hold at 4° C. PCR was performed on the cDNA using Taq DNA polymerase obtained from Invitrogen and using previously described conditions (50). Each gene amplicon was purified with the MiniElute PCR Purification Kit (Qiagen) and quantitated on an agarose gel by using a DNA mass ladder (Promega). These purified amplicons were used to optimize real-time PCR conditions and to generate standard curves in the real-time PCR assay. Primer concentrations and annealing temperatures were optimized for the iCycler iQ system (Bio-Rad) for each set of primers using the system's gradient protocol. PCR efficiencies were maintained between 92 and 105% and correlation coefficients above 0.98 for each primer set (Tables 1 and 6) during optimization and also during the real-time PCR of sample DNA.

Complementary DNA (cDNA) concentrations for genes of interest were examined by real-time quantitative PCR using an iCycler IQ System and the iQ SYBR green supermix (BioRad). A standard curve was generated for each gene using 10-fold dilutions of purified amplicons starting at 5 pg of cDNA and used later to calculate the starting amount of target cDNA in the unknown samples. SYBR green I is a general double-stranded DNA intercalating dye and may therefore detect nonspecific products and primer/dimers in addition to the amplicon of interest. In order to determine the number of products synthesized during the real-time PCR, a melting curve analysis was performed on each product. Real-time PCR was used to measure the starting amount of nucleic acid of each unknown sample of cDNA on the same 96-well plate. Results are presented as starting quantity of target cDNA (picograms) per microgram of total RNA.

Hepatic Steatosis, plasma MCP-1 and liver triglyceride content Liver specimens were excised and immediately fixed in 10% phosphate buffered neutral formalin, embedded in paraffin, cut at thicknesses of 5 microns and stained with hematoxylin and eosin (H&E) for histological examination. For hepatic triglyceride assessment, livers fragments (50-100 mg) were extracted for 16 hours at 4° C. with 4 ml CHCl/methanol (2:1, vol/vol). Two milliliters of 0.6% NaCl were then added to the extract, and the mixture was centrifuged at 2,000×g for 20 minutes. Lipids were isolated by nitrogen evaporation, dissolved in 100 µl isopropanol, and quantified with a triglyceride assay kit (Stanbio). The Triglyceride Assay Kit (Sigma) and Ready-set-go MCP-1 ELISA (ebioscience) were used to quantify plasma TGs and MCP-1, respectively, according to manufacturer's instructions.

Transfection of 3T3-L1 Preadipocytes

A pCMX.PPAR γ expression plasmid (kindly provided by Dr. R. M. Evans, The Salk Institute, San Diego, Calif.) and pMCP-1-514(enh) luc construct (51) were purified using Qiagen's Maxi kit (Valencia, Calif.). 3T3-L1 cells (American Type Culture Collection, Manassas, Va.) were grown in 24-well plates in DMEM high glucose medium (Invitrogen, Carlsbad, Calif.) containing 10% fetal bovine serum (FBS) until 60-70% confluence. Before transfection, the medium was changed to 1% FBS. The cells cultured in 24-well plates were co-transfected with 0.8 µg plasmid DNA and 1 ng of pRL reporter control plasmid per well using F-1 transfection reagents (Targeting Systems, Santee, Calif.) according to the manufacturer's protocol. Transfection efficiencies were determined by cotransfecting the cells with a pcDNA™ 3.1/His/lacZ control vector at 24 h. The transfected cells were then treated with either a racemic ABA mixture (12.5 µM; Sigma) or rosiglitazone (1 µM; Cayman Chemicals, Ann Arbor, Mich.) for 24 hours. Designated wells were also treated with the PPAR γ antagonist GW9662 (30 µM; Cayman Chemicals). Transfected cells were harvested in reporter lysis reagent. Luciferase activity, normalized to pRL activity in the cell extracts was determined by using the dual luciferase reporter assay system (Promega, Madison, Wis.) in a TD-20/20 Single-Tube Luminometer (Turner Biosystems, Sunnyvale, Calif.). Relative luciferase activity (RLA) was calculated as a ratio of the chemiluminescence 10 seconds after the Luciferase Assay Reagent II (Promega) was added over the chemiluminescence 10 seconds after the Stop&Glo Reagent (Promega).

Statistical Analyses

For the db/db experiment, data were analyzed as a completely randomized design. To determine the statistical significance of the model, analysis of variance (ANOVA) was performed using the general linear model procedure of Statistical Analysis Software (SAS). In the experiment using PPARYflfl; MMTV-Cre$^+$ and PPARYflfl; MMTV-Cre$^-$ mice, data were analyzed as a 2×2 factorial arrangement within a completely randomized design. The statistical model utilized was $Y_{ijk}=\mu+$Genetic Background$_i+$Diet$_j+$(Genetic Background×Diet)$_{ij}+$Error$_{ijk}$. To determine the statistical significance of the model, analysis of variance (ANOVA) was performed using the general linear model procedure of SAS, and probability value (P)<0.05 was considered to be significant. When the model was significant, ANOVA was followed by Fisher's Protected Least Significant Difference multiple comparison method. Non-parametric data were analyzed by using the Mann-Whitney U test followed by a Dunn's multiple comparison's test.

Results

Figure 9:
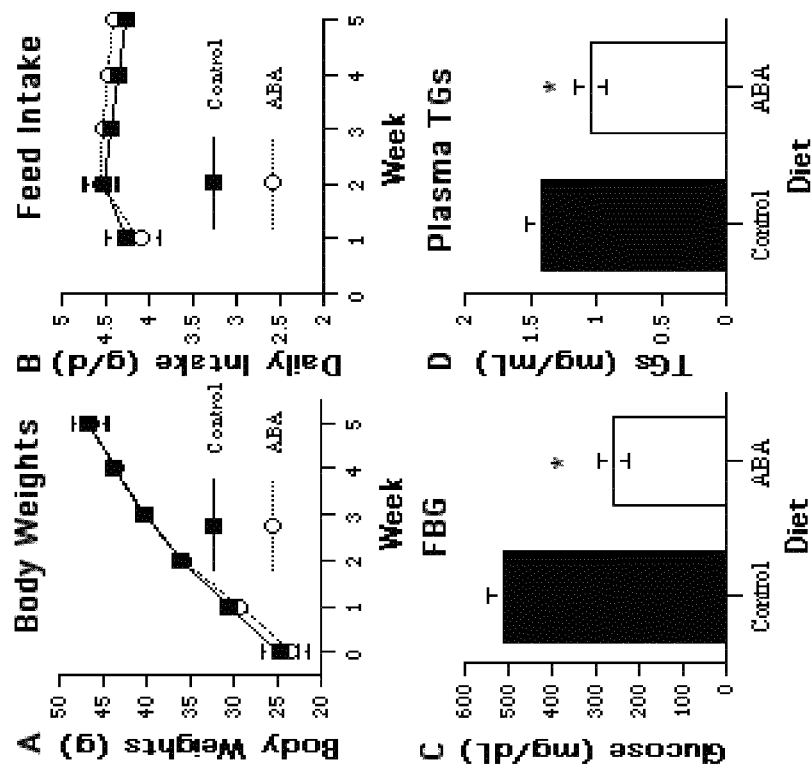
FIG. 9 shows plots demonstrating the effect of ABA on body weight, feed intake, fasting blood glucose, and plasma lipids. Panel A shows body weights; Panel B shows food intake; Panel C shows fasting blood glucose (FBG, milligrams/deciliter), and Panel D shows plasma triglycerides (TGs, mg/ml). Data are presented as least square means.+−.standard error of 10 mice. The error bars at some time points (FIGS. 9A and 9B) are smaller than the symbols and cannot be seen in the figure. Data points with an asterisk are significantly different (P<0.05).

ABA Improves Fasting Glucose and Lowers Plasma Triglycerides in db/db Mice Without Affecting Body Weight FIG. 9 shows that ABA ameliorates fasting glucose concentrations without inducing body weight gain. The effect of ABA on body weight, feed intake, fasting blood glucose and plasma lipids is shown in the figure. Db/db mice were fed control or ABA-supplemented (100 mg/kg diet) high-fat diets for 36 days. Panel (A): Body weights; and Panel (B): food intake were assessed weekly. After dietary treatment, plasma was withdrawn from fasted mice (12 h) to obtain fasting blood glucose (FIG. 9C; FBG, milligrams/deciliter) and plasma triglycerides (FIG. 9D; TGs, mg/ml). Data are presented as least square means±standard error of 10 mice. The error bars at some time points (FIGS. 9A and 9B) are smaller than the symbols and cannot be seen in the figure. Data points with an asterisk are significantly different (P<0.05).

ABA-supplementation to db/db mice for 36 days significantly lowers fasting glucose levels and improves their response to an intraperitoneal glucose tolerance test (48). Similar to these previous findings, ABA did not alter food intake or body weights of the db/db mice throughout the course of the experiment (FIGS. 9A and B). In this study, the db/db mice fed the ABA-supplemented diet had significantly lower fasting blood glucose (FBG) and plasma TGs concentrations when compared to mice fed the control high-fat diet (FIGS. 9C and D).

Figure 10:
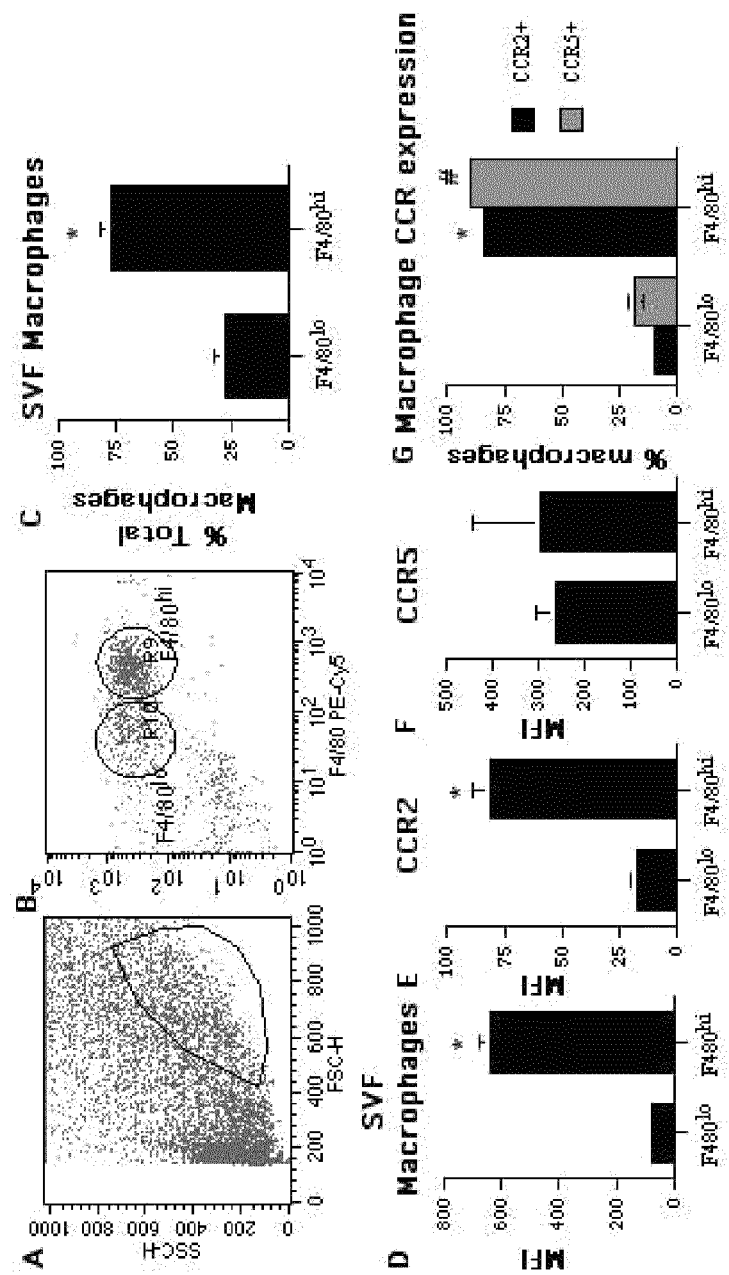
FIG. 10 depicts plots and graphs of a phenotypic analysis of macrophage subsets within the stromal-vascular fraction (SVF) of white adipose tissue (WAT). Panels (A) and (B) are representative dot plots from a control db/db mouse. The F4/80$^{hi}$ and F4/80$^{lo}$ subsets differed significantly in (C) total amount of macrophages and (D) mean fluorescence intensities (MFI). Panels (E) and (F) are graphs of the MFI's of CCR2 and CCR5-expressing macrophages in each population, respectively. Panel (G) represents the percentage of macrophages in each population expressing either CCR2 or CCR5. Data are presented as least square means.+−.standard error of 10 observations. Data points with an asterisk or number sign indicate a significant difference (P<0.05) between the separate macrophage populations.

The stromal-vascular fraction (SVF) contains two phenotypically distinct macrophage sub-populations FIG. 10 shows phenotypic analyses of macrophage subsets within the stromalvascular fraction (SVF) of white adipose tissue (WAT). Panels (A) and (B) are representative dot plots from a control db/db mouse. The $F4/80^{hi}$ and $F4/80^{lo}$ subsets differed significantly in (C) total amount of macrophages and (D) mean fluorescence intensities (MFI). (E) and (F) are the MFIs of CCR2 and CCR5-expressing macrophages in each population, respectively. (G) represents the percentage of macrophages in each population expressing either CCR2 or CCR5. Data are presented as least square means±standard error of 10 observations. Data points with an asterisk or number sign indicate a significant difference (P<0.05) between the separate macrophage populations.

More specifically, to characterize the phenotypical differences in ATM in the SVF, we examined surface expression of F4/80 and CD11b and chemokine receptors (CCR2 and CCR5). SVCs were isolated from adipocytes by gradient centrifugation and subsequently gated on the immune cell population based on forward versus side scatter (FIG. 10A). We identified two phenotypically distinct sub-populations of $F4/80^+CD11b^+$ macrophages in the SVF of WAT which differed in their mean fluorescence intensity (MFI) for F4/80, yielding a macrophage subset expressing high surface concentrations of the F4/80 molecule ($F4/80^{lo}$) and a subset expressing low surface concentrations of the F4/80 molecule) ($F4/80^{lo}$) (FIG. 10B, 10C). The $F4/80^{hi}$ population was more abundant in WAT than the $F4/80^{lo}$ subset, encompassing approximately 75% of total macrophages versus 25% in control-fed db/db mice, respectively (FIG. 10B). The $F4/80^{hi}$ macrophage subset also expressed higher surface concentrations of CCR2 and CCR5 when compared to the $F4/80^{lo}$ subset (FIG. 10G).

ABA Inhibits F4/80hi Macrophage Infiltration into WAT

Figure 11:
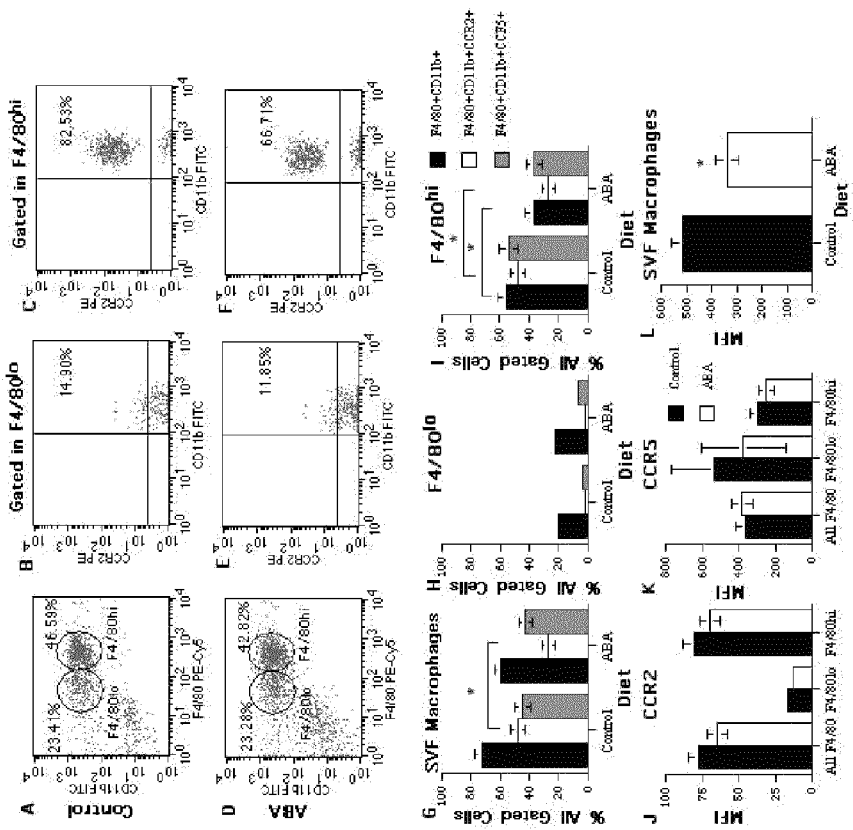
FIG. 11 shows plots and graphs of various characteristics of macrophages in control-fed and ABA-fed mice. The figure illustrates that abscisic acid (ABA) decreases the numbers of F4/80$^{hi}$ macrophages in white adipose tissue. Panels (A), (B), and (C) are representative dot plots for total stromal-vascular fraction (SVF) macrophage infiltration and the percentages of CCR2+ macrophages in the F4/80$^{hi}$ and F4/80$^{lo}$ subsets, respectively, for control-fed db/db mice. Panels (D), (E), and (F) are the respective dot plots for a representative ABA-fed db/db mouse. Panels (G), (H), and (I) indicate the contribution of SVF macrophages, F4/80lo macrophages, and F4/80hi macrophages to the total amount of gated cells. The mean fluorescence intensities (MFIs) of each macrophage subpopulation for (J) CCR2 and (K) CCR5. (L) is the difference in MFI of total SVF macrophages between control and ABA-fed mice. Data are presented as least square means±standard error of 10 observations. Data points with different superscripts are significantly different (P<0.05).

After characterizing these two macrophage sub-populations, we next determined whether ABA targeted one of these populations or both. We found that ABA significantly suppressed $F4/80^{hi}$ macrophage infiltration into WAT (P=0.05) but had no effect on the $F4/80^{lo}$ ATM. The results are shown in FIG. 11. The figure shows that ABA decreases the numbers of $F4/80^{hi}$ macrophages in white adipose tissue. Panels (A), (B), and (C) are representative dot plots for total stromal-vascular fraction (SVF) macrophage infiltration and the percentages of CCR2+ macrophages in the $F4/80^{hi}$ and $F4/80^{lo}$ subsets, respectively, for control-fed db/db mice. Panels (D), (E), and (F) are the respective dot plots for a representative ABA-fed db/db mouse. Panels (G), (H), and (I) indicate the contribution of SVF macrophages, $F4/80^{lo}$ macrophages, and $F4/80^{hi}$ macrophages to the total amount of gated cells. The mean fluorescence intensities (MFIs) of each macrophage sub-population for (J) CCR2 and (K) CCR5. Panel (L) is the difference in MFI of total SVF macrophages between control and ABA-fed mice. Data are presented as least square means±standard error of 10 observations. Data points with different superscripts are significantly different (P<0.05).

In addition, the amount of F4/80 expressed in the surface of $F4/80^{hi}$ macrophages administered ABA, as measured by MFI, was significantly lower than that in mice fed the control diet (FIG. 11L). The differences observed in the $F4/80^{hi}$ population in mice fed ABA were due primarily to a reduction in a subset of F4/80hi $CD11b^+CCR2^+$ATM (P=0.006).

ABA decreases MCP-1 mRNA expression in WAT, MCP-1 protein concentrations in plasma and attenuates liver triglyceride accumulation and hepatic steatosis A significant reduction in the infiltration of the $F4/80^{hi}CD11b^+CCR2^+$ macrophage subset into WAT could be due to attenuated CCR2 surface expression in monocytes, repression of CCR2 ligand expression in WAT, or both. CCR2 and its principal ligand, MCP-1, have been recently linked to the development of obesity-induced insulin resistance (52-54). To determine whether ABA inhibited MCP-1 expression in WAT, we assessed levels of MCP-1 mRNA content in the stromal vascular fraction (i.e., macrophages, T cells, fibroblasts, preadipocytes and endothelial cells) and in the adipocyte fraction. Both WAT fractions produce MCP-1 in obese mice and humans (16).

Figure 12:
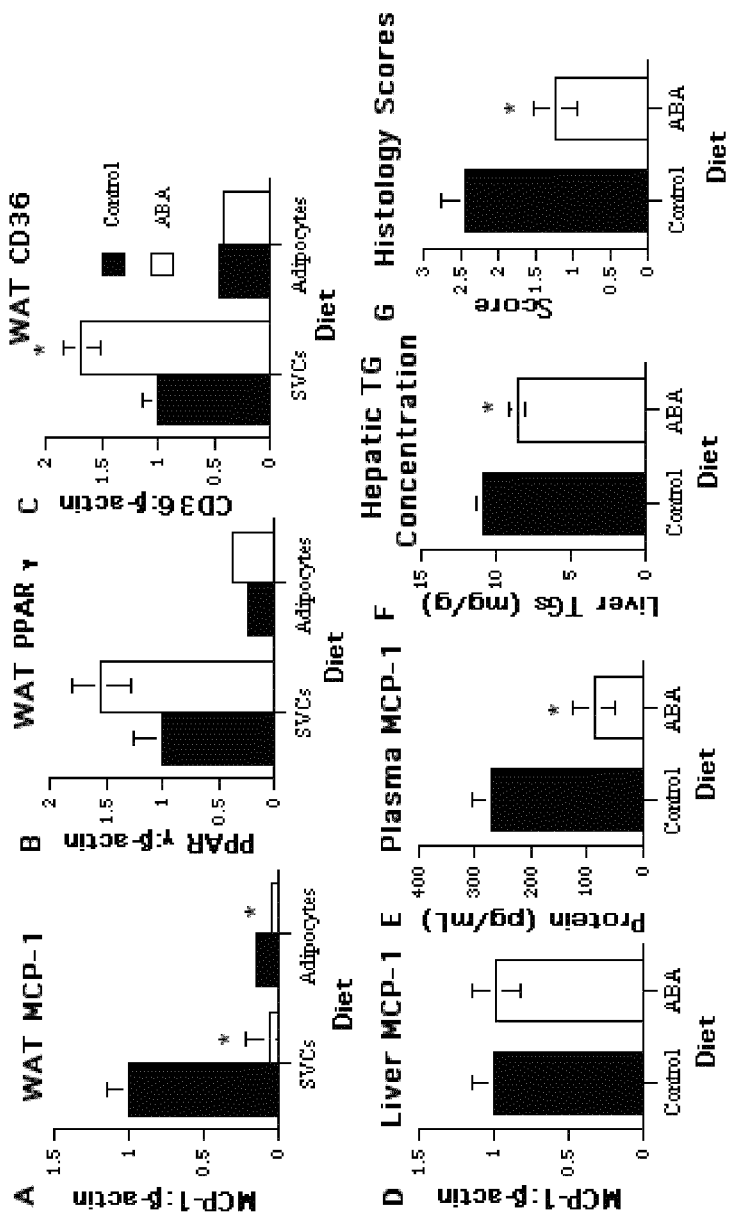
FIG. 12 shows graphs demonstrating the effect of dietary ABA supplementation on white adipose tissue and liver gene expression, MCP-1 protein levels, liver triglyceride concentrations, and hepatic steatosis scores. This figure illustrates that abscisic acid (ABA) induces PPAR gamma and suppresses the expression of MCP-1 in white adipose tissue. Db/db mice were fed high-fat diets with (black bars) or without (empty bars) ABA (100 mg/kg) for 36 days. Gene expression in RNA isolated from stromal-vascular cells (SVCs) and adipocytes was analyzed by real-time qRT-PCR for (A) monocyte chemoattractant protein 1 (MCP-1), (B) peroxisome proliferator-activated receptor gamma (PPAR gamma), and (C) CD36. (D) Liver MCP-1 expression, (E) plasma MCP-1 (picograms/milliliter), and (F) liver triglycerides (TG, mg/gram tissue) were also assessed. Gene expression values are expressed as a relative ratio to the housekeeping gene beta-actin. Data are presented as least square means.+−.standard error of 10 observations. Data points with an asterisk are significantly different (P<0.05). (G) Liver histology scores. (H) and (I) are representative photomicrographs of liver histology specimens stained with hemotoxylin and eosin (H&E).

FIG. 12 shows that ABA induces PPAR γ and suppresses the expression of MCP-1 in white adipose tissue. Specifically, the effect of dietary ABA supplementation on white adipose tissue and liver gene expression, MCP-1 protein levels, liver triglyceride concentrations and hepatic steatosis scores is shown in the figure. Db/db mice were fed high-fat diets with (black bars) or without (empty bars) ABA (100 mg/kg) for 36 days. Gene expression in RNA isolated from stromal-vascular cells (SVCs) and adipocytes was analyzed by real-time qRT-PCR for (A) monocyte chemoattractant protein 1 (MCP-1), (B) peroxisome proliferator-activated receptor γ (PPAR γ), and (C) CD36. (D) Liver MCP-1 expression, (E) plasma MCP-1 (picograms/milliliter), and (F) liver triglycerides (TG, mg/gram tissue) were also assessed. Gene expression values are expressed as a relative ratio to the housekeeping gene p-actin. Data are presented as least square means±standard error of 10 observations. Data points with an asterisk are significantly different (P<0.05). (G) Liver histology scores. (H) and (1) are representative photomicrographs of liver histology specimens stained with hemotoxylin and eosin (H&E).

We found that ABA decreased the concentrations of MCP-1 mRNA by almost 15-fold in SVCs. There was also a significant reduction in MCP-1 mRNA in the adipocyte fraction following ABA-supplementation (P=0.05), though this reduction was not as drastic as the difference we observed in SVCs (see FIG. 12A). PPAR γ mRNA expression was higher in both SVCs and adipocytes (FIG. 12B), but expression of the well-known PPAR γ-responsive gene and fatty acid transporter, CD36, was only significantly elevated in SVCs (FIG. 12C). We did not see significant differences in the mRNA expression of MIP-1α or the innate immune receptor toll-like receptor 4 (TLR-4) in either SVCs or adipocytes.

We next determined whether the suppressed MCP-1 expression observed in WAT of ABA-fed mice resulted in decreased plasma MCP-1 concentrations. MCP-1 protein concentrations were significantly decreased in plasma, but not in liver, from ABA-fed mice (FIGS. 12D and 12E), suggesting that WAT-derived MCP-1 may elicit systemic actions. In a recent study, MCP-1-overexpressing mice under control of the aP2-promoter (i.e., adipose tissue specific) had a significantly elevated risk of developing hepatic steatosis (53). Upon histological examination of liver specimens, we found that the hepatic steatosis was less severe in ABA-fed mice (FIG. 12G). In line with this histological finding, the amount of liver triglycerides was significantly lower in mice fed the ABA-supplemented diet as compared to mice fed the control diet (FIG. 12F).

Targeted deficiency of PPAR γ expression in immune cells impairs the ability of ABA to improve glucose tolerance The greatest differences in MCP-1 and the PPAR γ-responsive gene CD36 induced by ABA occurred in SVCs, suggesting that immune cell PPAR γ (and not adipocyte PPAR γ) is the molecular target for ABA in WAT. To determine whether the ability of ABA to normalize plasma glucose concentrations following a GTT was mediated through immune cell PPAR γ, we next fed high-fat diets supplemented with or without ABA to PPAR Yflfl; MMTV-Cre+ mice, which do not express PPAR Yin hematopoetic cells, and PPAR Yflfl; MMTV-Cre− littermates (wild-type phenotype). After 28 weeks of high-fat feeding, the mice were overweight (FIG. 13A). Similar to our findings with db/db mice, ABA did not increase body weights in either MMTV-Cre+ and MMTV-Cre− and did not effect food intake. The deficiency of PPAR Yin immune cells abrogated ABA-induced normalization of fasting blood glucose concentrations 90 minutes following an intraperitoneal GTT (FIGS. 13B and 13C).

Figure 13:
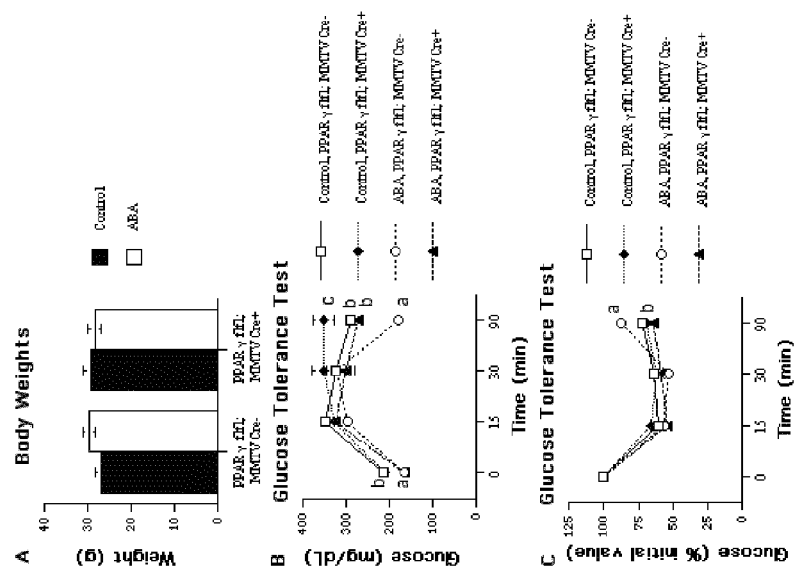
FIG. 13 shows plots that demonstrate the beneficial effects of ABA on insulin resistance are abrogated in immune cell-specific PPAR γ null mice. PPAR gamma flfl; MMTV-Cre+ and PPAR gamma flfl; MMTV-Cre-littermates (wild-type phenotype) were fed high-fat diets with or without ABA (100 mg/kg). (A) Final body weights and (B) response to an intraperitoneal glucose challenge (2 g glucose/kg body weight) in fasted mice (6 h) were assessed after 28 weeks of dietary supplementation. Data are presented as least square means±standard error of 8 mice. The error bars at some time points (FIGS. 13B and C) are smaller than the symbols and cannot be seen in the figure. Data points with different superscripts are significantly different (P<0.05).

More specifically, FIG. 13 shows the beneficial effects of ABA on insulin resistance are abrogated in immune cell-specific PPAR γ null mice. PPAR γ flfl; MMTV-Cre+ and PPAR γ flfl; MMTV-Cre− littermates (wild-type phenotype) were fed high-fat diets with or without ABA (100 mg/kg). (A) Final body weights and (B) response to an intraperitoneal glucose challenge (2 g glucose/kg body weight) in fasted mice (6 h) were assessed after 28 weeks of dietary supplementation. Data are presented as least square means±standard error of 8 mice. The error bars at some time points (FIGS. 13B and C) are smaller than the symbols and cannot be seen in the figure. Data points with different superscripts are significantly different (P<0.05).

Deficient PPAR γ expression in immune cells impairs the ability of ABA to suppress MCP-1 expression and infiltration of the F4/80$^{hi}$ macrophage subset into WAT To determine whether the observed differences in glucose tolerance corresponded to phenotypic changes in SVF macrophage subsets, we investigated the effect of ABA on both F4/80$^{hi}$ and F4/80$^{lo}$ ATM. Dietary ABA-supplementation significantly decreased both total SVF macrophage infiltration and the amount of F4/80$^{hi}$ macrophages in mice expressing PPAR γ in immune cells (i.e., PPAR γ fl/fl; MMTV-Cre−). However, the deficiency of PPAR γ in immune cells (i.e., PPAR γ fl/fl; MMTV-Cre+) abrogated the ability of ABA to suppress infiltration of F4/80$^{hi}$ into WAT. Of note, surface CCR2 was expressed by a greater percentage of ATM from tissue-specific PPAR γ null mice.

Figure 14:
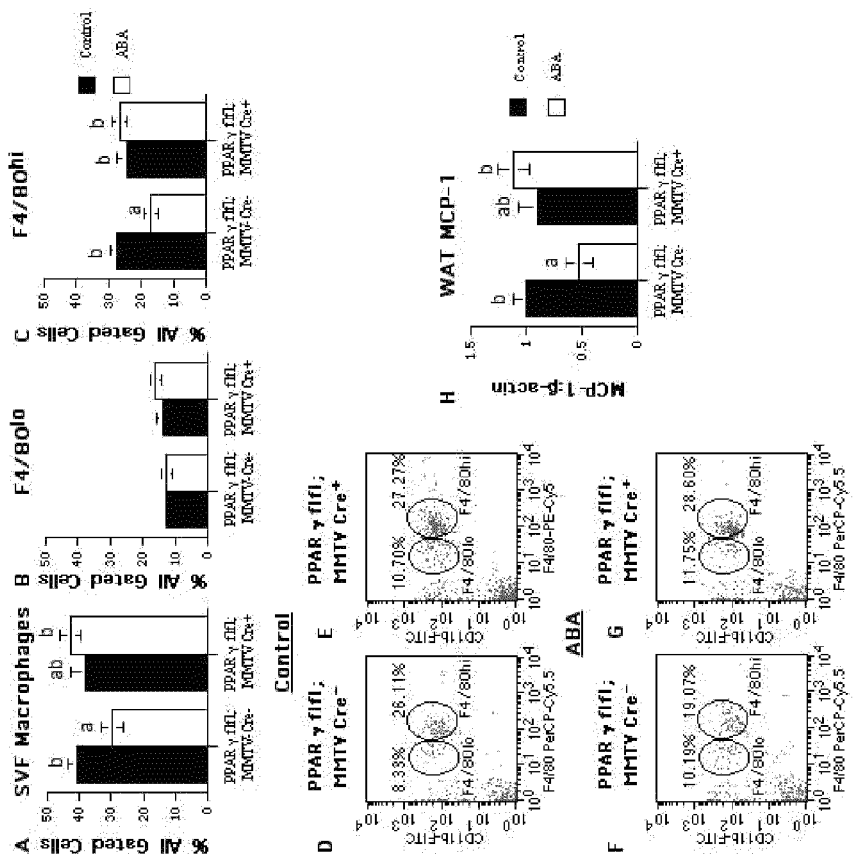
FIG. 14 shows graphs and plots demonstrating that the beneficial effects of ABA on the infiltration of monocytes and chemokine production in white adipose tissue are abrogated in immune cell-specific PPAR γ null mice. Panels (A), (B), and (C) represent the effects of ABA on total macrophage infiltration and the percentage of F4/80$^{lo}$ and F4/80$^{hi}$ ATM in PPAR gamma flfl; MMTV-Cre+ and PPAR gamma flfl; MMTV-Cre− mice. Panels (D) and (E) are representative dot plots for stromal-vascular fraction (SVF) infiltration of ATMs in PPAR gamma flfl; MMTV-Cre+ and PPAR gamma flfl; MMTV-Cre− mice fed the control high-fat diet. Panels (F) and (G) are the respective dot plots for ABA-fed mice. Real-time qRT-PCR was used to assess the expression of monocyte chemoattractant protein 1 (MCP-1) (Panel H). Data are presented as least square means.+−.standard error of 8 mice. The error bars at some time points (FIG. 14B) are smaller than the symbols and cannot be seen in the figure. Data points with different superscripts are significantly different (P<0.05).

In FIG. 14, results are shown that confirm that the beneficial effects of ABA on the infiltration of monocytes and chemokine production in white adipose tissue are abrogated in immune cell-specific PPAR γ null mice. The effect of dietary abscisic acid (ABA) supplementation and tissue-specific deletion of peroxisome proliferator-activated receptor γ (PPAR y) in immune cells on adipose tissue macrophage (ATM) phenotype is shown. (A), (B), and (C) represent the effects of ABA on total macrophage infiltration and the percentage of F4/80$^{lo}$ and F4/80$^{hi}$ ATM in PPAR γ flfl; MMTV-Cre+ and PPAR γ flfl; MMTV-Cre− mice. (D) and (E) are representative dot plots for stromal-vascular fraction (SVF) infiltration of ATMs in PPAR γ flfl; MMTV-Cre+ and PPAR γ flfl; MMTV-Cre− mice fed the control high-fat diet. (F) and (G) are the respective dot plots for ABA-fed mice. Real-time qRT-PCR was used to assess the expression of monocyte chemoattractant protein 1 (MCP-1) (H). Data are presented as least square means±standard error of 8 mice. The error bars at some time points (FIG. 14B) are smaller than the symbols and cannot be seen in the figure. Data points with different superscripts are significantly different (P<0.05).

We examined whether immune cell PPAR γ was required for the suppressive actions of ABA on WAT MCP-1 mRNA expression. ABA decreased both WAT and plasma MCP-1 levels in mice expressing PPAR γ in immune cells (FIG. 14H). However, in line with our findings on F4/80$^{hi}$ macrophage infiltration into WAT, the ability of ABA to suppress the expression of MCP-1 in WAT was significantly impaired in tissue-specific PPAR γ null mice, suggesting that ABA acts through a mechanism requiring the expression of PPAR γ in immune cells. The SVF of WAT contains macrophages, T cells, endothelial cells, fibroblasts and preadipocytes, but the only cell subsets in this fraction lacking the PPAR γ gene in the tissue specific PPAR γ null mouse would be the cells of hematopoietic origin i.e., bone marrow derived macrophages and T cells. Thus, the differences in glucose tolerance observed might be attributed to one or both immune cell subsets.

ABA Inhibits MCP-1 Promoter Activity through PPAR γ

Figure 15:
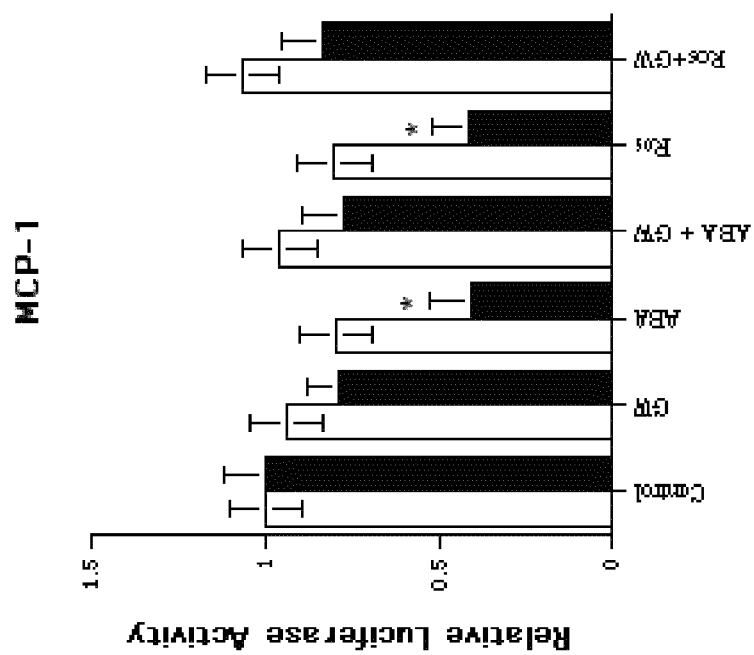
FIG. 15 shows a graph demonstrating that ABA inhibits MCP-1 promoter activity by acting through PPAR γ. 3T3-L1 pre-adipocytes were transfected with a MCP-1 promoter luciferase reporter construct with (black bars) or without (empty bars) co-transfection with a pCMX.PPAR gamma expression plasmid. After 20 hours, cells were treated with the PPAR gamma antagonist GW9662 (GW, 30 µM), ABA (12.5 µM), rosiglitazone (Ros, 1 µM), ABA and GW, or Ros and GW. The results were normalized for Renilla activity. Data are presented as least square means.+−.standard error of 4 observations. Data points with an asterisk are significantly different (P<0.05).

To further examine the effect of ABA on MCP-1 transactivation, 3T3-L1 preadipocytes were transfected with a MCP-1 promoter luciferase reporter construct and also cotransfected with a pCMX PPAR γ expression plasmid to increase endogenous PPAR γ activity. Cells were then treated with ABA (12.5 μM), rosiglitazone (1 μM), the PPAR γ antagonist GW9662 (30 μM), or a combination of agonist and inhibitor. We previously found that ABA (12.5 μM) and rosiglitazone (1 μM) were equally effective in inducing PPAR γ transactivation (48). In this study, co-transfection with the PPAR γ expression vector significantly enhanced the ability of both ABA and rosiglitazone to inhibit MCP-1 promoter activity (FIG. 15). The effects on MCP-1 transactivation by both compounds were significantly inhibited by cotreatment with GW9662.

FIG. 15 thus shows that ABA inhibits MCP-1 promoter activity by acting through PPAR γ. 3T3-L1 pre-adipocytes were transfected with a MCP-1 promoter luciferase reporter construct with (black bars) or without (empty bars) co-transfection with a pCMX.PPAR γ expression plasmid. After 20 hours, cells were treated with the PPAR γ antagonist GW9662 (GW, 30 μM), ABA (12.5 μM), rosiglitazone (Ros, 1 μM), ABA and GW, or Ros and GW. The results were normalized for *Renilla* activity. Data are presented as least square means±standard error of 4 observations. Data points with an asterisk are significantly different (P<0.05).

Discussion of Example 9 and FIGS. 9-15

The obesity and T2D epidemics follow a similar demographic pattern (1, 55), but little is known about the factors linking obesity to insulin resistance and T2D at the cellular and molecular level. The "FFA efflux theory" proposes that adipocyte dysfunction and extra-adipose fat storage are the central components in the pathogenesis of insulin resistance, highlighting the importance of adipocytes as cellular targets (56). In contrast, the "endocrine theory" suggests that pro-inflammatory mediators play an essential immunopathogenic role, favoring immune cells as central cellular targets for therapies against T2D (57). PPAR γ is expressed in both adipocytes and immune cells and has been identified as an important therapeutic target both in insulin resistance and T2D. In this document, we show that PPAR γ and its responsive gene CD36 are expressed at higher concentrations in SVCs than in adipocytes and that treatment with a novel insulin-sensitizing PPAR γ agonist induces PPAR γ-responsive gene expression primarily in SVCs. These results are also suggestive that TZDs may elicit their insulin-sensitizing actions through PPAR γ expressed in immune cells infiltrating the WAT. Hence, PPAR γ activation in immune cells may be considered a central regulator of insulin resistance and obesity-related inflammation. In line with this conclusion, obesity-induced insulin resistance is associated with the infiltration of bone-marrow-derived monocytes into WAT and differentiation into ATM (16,17). The studies presented herein phenotypically characterized the subsets of ATM targeted by ABA and investigated whether this compound ameliorates insulin resistance and obesity-related inflammation through a mechanism dependent upon immune cell PPAR γ.

We have previously found that ABA improves glucose tolerance and reduces total ATM infiltration and TNF-α expression in WAT of db/db mice (58). We report for the first time the presence of two phenotypically distinct subsets of macrophages in the SVF of WAT which differ in the amount of surface F4/80 (e.g., $F4/80^{lo}$ and $F4/80^{hi}$). The newly identified $F4/80^{hi}$ subset is more abundant (e.g., 75% of the macrophages in the SVF) and expresses higher surface concentrations of CCR2 and CCR5 in comparison to the $F4/80^{lo}$ population.

The expression of F4/80 is tightly regulated according to the physiological status of cells. Because the precursor of tissue macrophages, the bone-marrow derived blood monocyte, expresses lower surface F4/80 than its mature counterparts (58), the $F4/80^{hi}$ ATM subset is probably a mature cell type that contributes to obesity-related inflammation, whereas $F4/80^{lo}$ ATM may be monocytes, which have recently transmigrated into the WAT. Alternatively, a difference in the ontogeny of $F4/80^{hi}$ and $F4/80^{lo}$ macrophages could account for these two distinct ATM subsets. The SVF, in addition to containing bone marrow-derived cells of myeloid origin, includes pre-adipocytes that can differentiate into adipocytes or F4/80-expressing macrophages of mesenchymal origin (59). Resident macrophages from different organs differ considerably in the amount of F4/80 expressed on their surfaces (60). Moreover, the limited expression of chemokine receptors on the majority of $F4/80^{lo}$ ATMs may be indicative of a predominantly resident population (61).

After phenotypically characterizing these two ATM subsets, we next examined the ability of ABA to differentially modulate their numbers in WAT. We found that ABA decreased the amount of $F4/80^{hi}$ CCR2+ ATM but had a negligible effect on the $F4/80^{lo}$ population. Although the effect of synthetic PPAR γ ligands on the infiltration of $F4/80^{hi}$ $CCR2^{+}$ ATM has not been studied, the reduction of this subset of ATM by ABA is in line with the well characterized ability of PPAR γ to suppress CCR2 expression. At the molecular level, the CCR2 gene contains two promoters which are both repressed by PPAR (62) and TZDs downregulate the MCP-1-induced chemotactic response in THP-I monocytes (63). Moreover, in obese mice matched for adiposity, Ccr2 deficiency decreased macrophage content and WAT inflammation while ameliorating hepatic steatosis (52). Our data supports the contention that ABA activates PPAR γ in monocytes, which, in turn, suppresses surface CCR2 expression and infiltration of $F4/80^{hi}$ ATM.

We next determined whether ABA downregulated the expression of MCP-1, the main ligand for CCR2, in WAT. Similar to CCR2, MCP-1 is inhibited following TZD treatment in both SVCs and adipocytes (64). We found a 15-fold decrease in MCP-1 mRNA in the SVF of WAT and a 4-fold decrease in plasma MCP-1. The decrease observed in the SVCs was far greater than the approximately 2-fold decrease. Xu et al. obtained following similar short-term intervention with rosiglitazone in ob/ob mice (17). In addition to recruiting macrophages and directly impairing insulin signaling by blocking IRS-1 and Akt phosphorylation (53). In line with the suppressed expression of MCP-1 mRNA in WAT and decreased concentrations of MCP-1 protein in plasma of ABA-fed mice, we observed a decreased severity in high-fat diet induced hepatic steatosis which could not be attributed to differences in MCP-1 mRNA expression in the liver. In addition to the decreased systemic MCP-1 concentrations, the ABA induced reduction in plasma TGs may contribute to the improvement of liver steatosis. To further characterize the role of PPAR γ in mediating ABA-induced repression of MCP-1, we cotransfected 3T3-L1 pre-adipocytes with a MCP-1 reporter construct and a PPAR γ expression vector. The presence of the expression vector significantly enhanced the ability of both ABA and rosiglitazone to inhibit MCP-1 promoter activity. The effects of both compounds were also inhibited by the selective PPAR γ antagonist GW9662, suggesting that the ABA-induced repression of MCP-1 expression in WAT is mediated through the inhibitory actions of activated PPAR γ on the MCP-1 promoter.

Because macrophages are the main producers of MCP-1 in WAT, we next examined whether the deletion of PPAR γ in immune cells would impair the ability of ABA to ameliorate insulin resistance and obesity-related inflammation. For this purpose, we used a mouse model in which the PPAR γ gene has been disrupted in immune cells. While several studies have been performed on muscle specific (65), until now, little was known about the importance of immune cell PPAR γ in the regulation of insulin resistance and T2D. The PPAR γ fl/fl; MMTV-Cre$^+$ mice lack PPAR γ in immune and epithelial cells but express it at normal concentrations in adipocytes. Thus, they represent an excellent model to dissect the immune cell-dependent mechanisms of PPAR γ action. We have previously used this loss-of-function approach to characterize in vivo the mechanism by which conjugated linoleic acid, another natural agonist of PPAR γ, prevents intestinal inflammation (50). Our present findings indicate that the loss of PPAR γ in immune cells impairs the ability of ABA to improve glucose tolerance, suppress $F4/80^{hi}$ ATM infiltration, and down-regulate MCP-1 expression in WAT, suggesting that the protective actions of ABA on insulin resistance are mediated, in part, through a mechanism dependent upon expression of PPAR γ in immune cells.

In summary, we have characterized for the first time two phenotypically distinct subsets of ATM ($F4/80^{hi}$ and $F/4/80^{lo}$) and demonstrated that a novel PPAR γ agonist decreases the infiltration of $F4/80^{hi}$ ATM, MCP-1 expression in WAT, MCP-1 promoter activity, and ameliorates insulin resistance through a mechanism requiring immune cell PPAR γ. These data further support the theory that immune cell-derived pro-inflammatory mediators are components in the pathogenesis of insulin resistance and T2D.

Example 10

Effect of Dietary Abscisic Acid Supplementation on Colitis Severity and Pro-Inflammatory Gene Expression Research Design and Methods
Animal Procedures Six to eight week old C57BL/6J mice (n=20) and were housed at the animal facilities at Virginia Polytechnic Institute and State University in a room maintained at 75° F., with a 12:12 h light-dark cycle starting from 6:00 AM. All experimental procedures were approved by the Institutional Animal Care and Use Committee of Virginia Polytechnic Institute and State University and met or exceeded requirements of the Public Health Service/National Institutes of Health and the Animal Welfare Act. C57BL/6J mice were fed AIN-93G-based diets with or without 100 mg/kg of a racemic ABA mixture for 35 days prior to induction of colitis with water containing 2.5% dextran sodium sulfate (DSS), 36,000-14,000 mol wt (ICN Biomedicals, Aurora, Ohio). After the DSS challenge mice were weighed on a daily basis and examined for clinical signs of disease associated with colitis (i.e., perianal soiling, rectal bleeding, diarrhea, and piloerection). For the DSS challenge, the disease activity indices and rectal bleeding scores were calculated using a modification of a previously published compounded clinical score (50). Briefly, the disease activity index consisted of a scoring for diarrhea and lethargy (0-3), whereas rectal bleeding consisted of a visual observation of blood in feces and the perianal area (0-4). Mice in the DSS study were euthanized on day 7 of the DSS challenge. On day 7 blood mice were euthanized by $CO_2$ asphyxiation and blood was withdrawn from the heart. Spleen and mesenteric lymph nodes (MLN) were scored based on size and macroscopic inflammatory lesions (0-3), excised, and then crushed to produce single-cell suspensions for flow cytometry.

Histopathology

Colonic sections were fixed in 10% buffered neutral formalin, later embedded in paraffin, and then sectioned (5 μm) and stained with H&E stain for histologic examination. Colons were graded with a compounded histologic score including the extent of (1) lymphocyte infiltration, (2) mucosal thickening, and (3) epithelial cell erosion. The sections were graded with a score of 0-4 for each of the previous categories and data were analyzed as a normalized compounded score.

Quantitative Real-Time PCR

Total RNA was isolated from colons using the RNA isolation Minikit (Qiagen) according to the manufacturer's instructions. Total RNA (1 μg) was used to generate complementary DNA (cDNA) template using the iScript cDNA Synthesis Kit (Bio-Rad, Hercules, Calif.). The total reaction volume was 20 μL with the reaction incubated as follows in an MJ MiniCycler: 5 minutes at 25° C., 30 minutes at 52°, 5 minutes at 85° C., and hold at 4° C. PCR was performed on the cDNA using Taq DNA polymerase (Invitrogen, Carlsbad, Calif.) and using previously described conditions (50). Each gene amplicon was purified with the MiniElute PCR Purification Kit (Qiagen) and quantitated on an agarose gel by using a DNA mass ladder (Promega). Those purified amplicons were used to optimize real-time PCR conditions and to generate standard curves in the real-time PCR assay. Primer concentrations and annealing temperatures were optimized for the iCycler iQ system (Bio-Rad) for each set of primers using the system's gradient protocol. PCR efficiencies were maintained between 92 and 105% and correlation coefficients above 0.98 for each primer set during optimization and also during the real-time PCR of sample DNA.

Complementary DNA (cDNA) concentrations for genes of interest were examined by real-time quantitative PCR using an iCycler IQ System and the iQ SYBR green supermix (Bio-Rad). A standard curve was generated for each gene using 10-fold dilutions of purified amplicons starting at 5 pg of cDNA and used later to calculate the starting amount of target cDNA in the unknown samples. SYBR green I is a general double-stranded DNA intercalating dye and may therefore detect nonspecific products and primer/dimers in addition to the amplicon of interest. In order to determine the number of products synthesized during the real-time PCR, a melting curve analysis was performed on each product. Real-time PCR was used to measure the starting amount of nucleic acid of each unknown sample of cDNA on the same 96-well plate. Results are presented as starting quantity of target cDNA (picograms) per microgram of total RNA.

2.6 Statistics

Data were analyzed as a completely randomized design. To determine the statistical significance of the model, analysis of variance (ANOVA) was performed using the general linear model procedure of Statistical Analysis Software (SAS), and probability value (P)<0.05 was considered to be significant. When the model was significant, ANOVA was followed by Fisher's Protected Least Significant Difference multiple comparison method.

Results and Discussion

ABA Reduces Disease Activity and Colonic Inflammation

Figure 16:
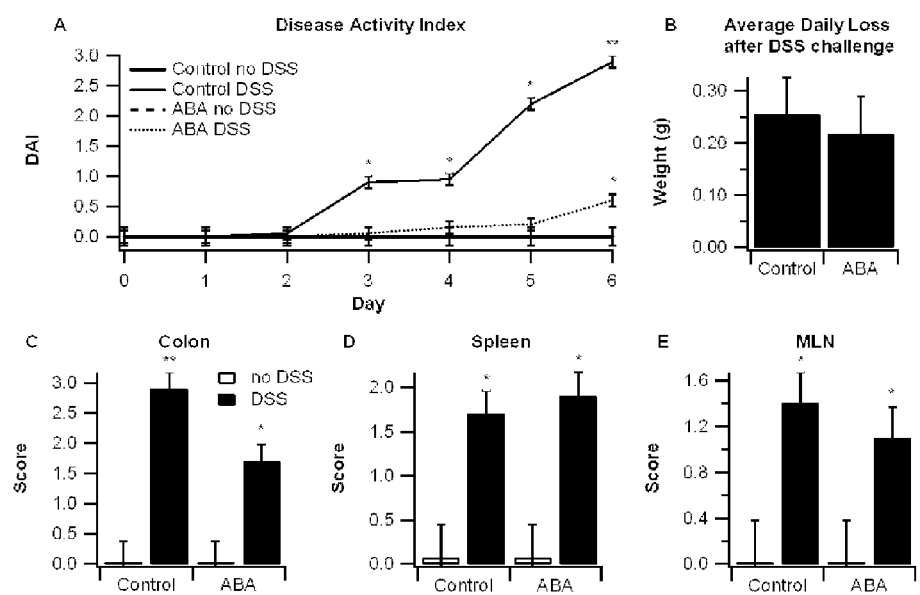
FIG. 16 shows plots and graphs demonstrating the effect of dietary abscisic acid (ABA) supplementation on the severity of colitis. C57BL/6J mice were fed ABA-supplemented (100 mg/kg) or control diets for 35 days and then challenged with 2.5% dextran sodium sulfate (DSS) or water (no DSS) for 7 days. The disease activity index (DAI), a composite score reflecting clinical signs of the disease (i.e. perianal soiling, rectal bleeding, diarrhea, and piloerection) was assessed daily (A) and the average daily loss in body weights (B) were calculated for mice undergoing the DSS challenge. On day 7 mice were euthanized and the colon, spleen, and mesenteric lymph nodes (MLN) (C-E) were macroscopically scored for inflammation. Data are represented as mean±standard error. Points with an asterisk are significantly different from control, non-DSS treatment (P<0.05).

To determine the effect of ABA on colonic inflammation, mice were fed diets with or without ABA (100 mg/kg) for 35 days prior to DSS challenge. After 7 days, mice fed ABA had a significantly reduced disease activity index (DAI) compared to control-fed mice (FIG. 16A). There were no significant differences in body weight loss between the two groups although ABA intake numerically decreased weight loss (FIG. 16B). The colon, spleen, and mesenteric lymph nodes (MLN) from each mouse were scored based on gross anatomical signs of inflammation. The DSS challenge increased the macroscopic score of all three tissues (FIGS. 16C-16E). Based on the anatomical observation, ABA significantly reduced colonic inflammation but had no significant effect on the spleen or MLN.

ABA Improves Colon Histopathology and Reduces Leukocyte Infiltration

Macroscopic and observational data indicated that ABA-supplementation ameliorated IBD severity. To more closely examine the effect of ABA, colon specimens from mice were examined histologically. In line with reduced DAI, mice fed ABA showed significant histological improvements in the colon (FIG. 17). Epithelial erosion, mucosal thickening, and leukocyte infiltration were significantly reduced in ABA-fed mice with DSS colitis (FIG. 17).

ABA Suppresses Colonic Expression of Adhesion Molecules

We have previously shown that ABA activates PPAR γ, and PPAR γ agonists have been successfully used in the treatment of IBD (71). Thus, we sought to determine whether ABA modulates gene expression in a manner that resembled established agonists of PPAR γ such as rosiglitazone or conjugated linoleic acid. Here, we found no evidence of PPAR γ-mediated affect in colons of ABA-fed mice. Neither colonic PPAR γ nor its responsive genes CD36, or FABP4 were significantly affected by ABA.

Despite no increase in PPAR γ, ABA-supplementation significantly lowered the colonic expression of adhesion molecules VCAM-1, muscosal vascular addressin cell adhesion molecule 1 (MAdCAM-1), and E-selectin and had no affect on intracellular adhesion molecule 1 (ICAM-1) or platelet endothelial cell adhesion molecule 1 (PECAM-1). Colons from ABA-treated mice also had significantly attenuated levels of inflammatory proteins IL-6, iNOS, and MMP-9. IL-6 and iNOS are proteins secreted mainly by M1 activated macrophages, while MMP-9 is secreted predominantly by neutrophils and is a key mediator of tissue damage in IBD (76).

Example 11

Effect of Abscisic Acid Supplementation on Colitis Severity in Mice Lacking PPAR γ in CD4+ T-Cells Research Design and Methods Animal Procedures Eight to twelve week old C57BL/6J (n=16) and PPAR γ flfl; CD4 cre+(n=20) mice were housed at the animal facilities at Virginia Polytechnic Institute and State University in a room maintained at 75° F., with a 12:12 h light-dark cycle starting from 6:00 AM. All experimental procedures were approved by the Institutional Animal Care and Use Committee of Virginia Polytechnic Institute and State University and met or exceeded requirements of the Public Health Service/National Institutes of Health and the Animal Welfare Act. C57BL/6J mice were fed AIN-93G-based diets with or without 100 mg/kg of a racemic ABA mixture for 35 days prior to induction of colitis with water containing 2.5% dextran sodium sulfate (DSS), 36,000-44,000 mol wt (ICN Biomedicals, Aurora, Ohio). After the DSS challenge mice were weighed on a daily basis and examined for clinical signs of disease associated with colitis (i.e., perianal soiling, rectal bleeding, diarrhea, and piloerection). For the DSS challenge, the disease activity indices and rectal bleeding scores were calculated using a modification of a previously published compounded clinical score (50). Briefly, disease activity index consisted of a scoring for diarrhea and lethargy (0-3), whereas rectal bleeding consisted of a visual observation of blood in feces and the perianal area (0-4). Mice in the DSS study were euthanized on day 7 of the DSS challenge. On day 7 blood mice were euthanized by $CO_2$ asphyxiation and blood was withdrawn from the heart. Spleen and mesenteric lymph nodes (MLN) were scored based on size and macroscopic inflammatory lesions (0-3), excised, and then crushed to produce single-cell suspensions for flow cytometry.

Immunophenotyping of Blood and Mesenteric Lymph Nodes

MLNs were excised and crushed with frosted slides, washed with PBS, and resuspended in PBS and enumerated with a Coulter Counter (Beckman Coulter, Fullerton, Calif.). MLN-derived cells ($2\times10^5$ cells/well) or whole blood (10 µL/well) were seeded onto 96-well plates, centrifuged at 4° C. at 3000 rpm for 4 minutes, and washed with PBS containing 5% serum and 0.09% sodium azide (FACS buffer). To assess differential monocyte/macrophage infiltration, the cells were then incubated in the dark at 4° C. for 20 minutes in FcBlock (20 µg/ml; BD Pharmingen) for macrophage assessment, and then for an additional 20 minutes with fluorochrome-conjugated primary antibodies anti-F4/80-PE-Cy5 (5 µg/mL, ebioscience), anti-CD11b-Alexa Fluor 700 (2 µg/mL, eBioscience), and anti-Ly6C-biotin, using PE-Texas Red as a secondary antibody. For lymphocyte assessment, cells were incubated with anti-CD4-Alexa Fluor 700 (2 µg/mL; BD Pharmingen), anti-CD8-PerCp-Cy5.5 (2 µg/mL, eBioscience), CD3 PE-Cy5 (2 µg/mL; BD Pharmingen), anti-CD25-FITC (BD), anti-CTLA-4 FITC (BD), or anti-FoxP3-PE (2 µg/mL, eBioscience) as previously shown (77). Flow results were computed with a BD LSR II flow cytometer and data analyses was performed with FACS Diva software (BD).

CTLA-4 Assessment in Cultured Splenocytes

Splenocytes from wild-type mice (n=2) were isolated under sterile conditions and seeded into 96-well plates as described above. Cells were stimulated with anti-CD3 (5 µg/mL; BD Pharmingen) and anti-CD28 (1 µg/mL; BD Pharmingen) to induce proliferation and then treated with DMSO or ABA (10 µM, Sigma). Cells were then placed in a 37° C. incubator with 5% $CO_2$ for 20 hours and immunophenotyped with anti-CD4 Alexa Fluor 700 (BD Pharmingen), anti-CD3-PE-Cy5 (BD Pharmingen), anti-CD8-PerCp-Cy5.5 (eBioscience), and'anti-CD152 (CTLA-4)-biotin (BD). Streptavidin PE-Texas Red (1 µg/mL; BD Pharmingen) was used as a secondary antibody. Flow results were computed with a BD LSR II flow cytometer and data analyses was performed with FACS Diva software (BD).

Results and Discussion

ABA-Induced Improvements in Colitis Severity are Dependent on PPAR γ CD4+ T-Cells We have previously demonstrated that dietary ABA-supplementation protects mice from DSS-induced colitis. With this study our objective was to assess whether those improvements were dependent on PPAR γ. Similar to our previous findings, we found that wild-type (wt) mice who received the ABA-supplemented diet had significantly reduced disease activity and macroscopically observable inflammation than those fed the control diet (FIG. 19). Those improvements by ABA were not present in the CD4cre mice, which lack PPAR γ in CD4+ T cells. Aside from preventing the beneficial effects of ABA, the lack of PPAR γ had no observable effect on the severity of IBD. These clinical findings provide visible evidence that ABA-induced improvements in disease activity are dependent on PPAR γ.

ABA Reduces Blood Monocytes and Increases Regulatory T Cells in Blood and MLN

We found that ABA supplementation significantly decreased F4/80+CD11b+ monocytes in wt mice. This effect was absent in the PPAR γ-deficient mice (FIG. 20). ABA also significantly increased the percent of CD4+CD25+FoxP3+ regulatory T cells in the MLN. An increase in blood monocytes and macrophage-induced inflammation is a hallmark of DSS-induced colitis, and the noted difference between the ABA-induced effects in wt mice versus CD4cre mice show that ABA's actions on lymphocytes, specifically PPAR γ-expressing, CD4+ lymphocytes, are related to decreased monocytes and increased T-regs. These findings indicate that ABA acts as an immunomodulator in lymphocytes and that PPAR γ is required for these effects.

ABA Increases CTLA-4 Expression on CD4+ T Cells

To further examine the immunomodulatory role of ABA we assessed CTLA-4 expression on the surface of CD4+ T cells in blood (FIG. 21). CTLA-4 is an immunomodulating protein on lymphocytes whose genetic polymorphisms have been linked to IBD in humans (78). CTLA-4 expression was significantly increased in ABA-fed wild-type mice, and similar to previous results this increase was abrogated with the lack of PPAR γ.

We also assessed whether stimulation with ABA in vitro would act to upregulated CTLA-4 expression. ABA was added to CD3/CD28-stimulated splenocytes and cultured for 20 hr, and CTLA-4 expression and median fluorescence intensity (MFI) was assessed for CD4+ cells. Treatment with ABA significantly increased the percent of CD4+ T cells expressing CTLA-4 and also increased CTLA-4 MFI, which is indicative of increased protein on the cell surface.

Example 12

Reduction of Cellular Adhesion Molecules and Upregulation of CTLA-4 Expression by ABA for the Treatment of Automimmune Disorders FIG. 3 demonstrates that ABA significantly decreases mRNA of cellular adhesion molecules VCAM-1, MAdCAM-1, and E-selectin in colons of DSS-treated mice. ABA-fed mice also showed significant increases in CTLA-4 expression in blood CD4+ T cells. In addition to their association with IBD, cellular adhesion molecules are associated with increased disease severity in autoimmune disorders such as type I diabetes and rheumatoid arthritis (79, 80). In type I diabetes, the development of retinopathy and other micro- and macrovascular disorders are associated with the increased presence of soluble VCAM-1 and E-selectin (79, 81). With rheumatoid arthritis adhesion molecules play an important role in the pathogenesis of endothelial-leukocyte interactions, angiogenesis and lymphocyte activation (82). Both type I diabetes and rheumatoid arthritis have been linked to polymorphisms in the CTLA-4 gene (83, 84), and the use of CTLA-4 immunoglobulin has already received FDA approval for the treatment of rheumatoid arthritis. Our finding that ABA treatment significantly reduces adhesion molecule expression and increases CTLA-4 expression in CD4+ T cells invites the possibility that these same functions may be applied to other autoimmune disorders, where lymphocytes and adhesion molecules play important pathogenic roles.

Example 13

Reduction of Cellular Adhesion Molecules and Upregulation of CTLA-4 ABA for Improvement of Transplant Outcomes The increased presence of cellular adhesion molecules and enhanced lymphocyte activation are associated with graft rejection in transplant patients (85). Adhesion molecules are believed to play an important role in the infiltration of lymphocytes into the transplanted tissue and in the costimulation of T cell activation (86), and the blockade of cellular adhesion molecules in animal models has been shown to prevent rejection (87). Evidence has also shown that CTLA-4 is critically involved in the regulation of the human immune response to allogeneic grafts (88), and polymorphisms in the CTLA-4 gene are associated with impaired transplant outcomes (75). With our finding that ABA reduces adhesion molecule expression, it is reasonable to assess its applicability in the prevention of graft rejection.

It will be apparent to those skilled in the art that various modifications and variations can be made in the practice of the present invention without departing from the scope of the invention. Other embodiments of the invention will be apparent to those skilled in the art from consideration of the specification and practice of the invention. It is intended that the specification and examples be considered as exemplary only, with a true scope and spirit of the invention being indicated by the following claims.

REFERENCES 1. 2. CDC: National Diabetes Fact Sheet: general information and national estimates on diabetes in the United States, 2005. In *U.S. Department of Health and Human Services, Center for Disease Control and Prevention,* 2005 Atlanta, Ga., 2005, p. 1-10.
3. Narayan K M, Boyle J P, Thompson T J, Sorensen S W, Williamson D F: Lifetime risk for diabetes mellitus in the United States. *JAMA* 290:1884-1890, 2003.
4. Lehmann J M, Moore L B, Smith-Oliver T A, Wilkison W O, Willson T M, Kliewer S A: An antidiabetic thiazolidinedione is a high affinity ligand for peroxisome proliferator-activated receptor gamma (PPAR gamma). *J Biol Chem* 270:12953-12956, 1995.
5. Braissant O, Foufelle F, Scotto C, Dauca M, Wahli W: Differential expression of peroxisome proliferator-activated receptors (PPARs): tissue distribution of PPAR-alpha, -beta, and -gamma in the adult rat. *Endocrinology* 137:354-366, 1996.
6. Chawla A, Schwarz E J, Dimaculangan D D, Lazar M A: Peroxisome proliferator-activated receptor (PPAR) gamma: adipose-predominant expression and induction early in adipocyte differentiation. *Endocrinology* 135:798-800, 1994.
7. Lehrke M, Lazar M A: The many faces of PPARgamma. *Cell* 123:993-999, 2005.
8. McKenna N J, O'Malley B W: Combinatorial control of gene expression by nuclear receptors and coregulators. *Cell* 108:465-474, 2002.
9. Bassaganya-Riera J, A. Guri, J. King, and R. Hontecillas: Peroxisome Proliferator-Activated Receptors: the Nutritionally Controlled Molecular Networks that Integrate Inflammation, Immunity and Metabolism. *Current Nutrition & Food Science.* 1: 179-187, 2005.
10. Olefsky J M: Treatment of insulin resistance with peroxisome proliferator-activated receptor gamma agonists. *J Clin Invest* 106:467-472, 2000.
11. Bogacka I, Xie H, Bray G A, Smith S R: The effect of pioglitazone on peroxisome proliferator-activated receptor-gamma target genes related to lipid storage in vivo. *Diabetes Care* 27:1660-1667, 2004.
12. Rajala M W, Scherer P E: Minireview: The adipocyte—at the crossroads of energy homeostasis, inflammation, and atherosclerosis. *Endocrinology* 144:3765-3773, 2003.
13. Trayhurn P: Endocrine and signalling role of adipose tissue: new perspectives on fat. *Acta Physiol Scand* 184: 285-293, 2005.
14. Yamauchi T, Kamon J, Minokoshi Y, Ito Y, Waki H, Uchida S, Yamashita S, Noda M, Kita S, Ueki K, Eto K, Akanuma Y, Froguel P, Foufelle F, Ferre P, Carling D, Kimura S, Nagai R, Kahn B B, Kadowaki T: Adiponectin stimulates glucose utilization and fatty-acid oxidation by activating AMP-activated protein kinase. *Nat Med* 8:1288-1295, 2002.
15. Zick Y: Insulin resistance: a phosphorylation-based uncoupling of insulin signaling. *Trends Cell Biol* 11:437-441, 2001.
16. Weisberg S P, McCann D, Desai M, Rosenbaum M, Leibel R L, Ferrante A W, Jr.: Obesity is associated with macrophage accumulation in adipose tissue. *J Clin Invest* 112: 1796-1808, 2003.
17. Xu H, Barnes G T, Yang Q, Tan G, Yang D, Chou C J, Sole J, Nichols A, Ross J S, Tartaglia L A, Chen H: Chronic inflammation in fat plays a crucial role in the development of obesity-related insulin resistance. *J Clin Invest* 112: 1821-1830, 2003.
18. de Souza C J, Eckhardt M, Gagen K, Dong M, Chen W, Laurent D, Burkey B F: Effects of pioglitazone on adipose tissue remodeling within the setting of obesity and insulin resistance. *Diabetes* 50:1863-1871, 2001.
19. Yamauchi T, Kadowaki T: [The molecular mechanisms by which PPAR gamma/RXR inhibitors improve insulin resistance]. *Nippon Rinsho* 59:2245-2254, 2001.
20. Nesto R W, Bell D, Bonow R O, Fonseca V, Grundy S M, Horton E S, Le Winter M, Porte D, Semenkovich C F, Smith S, Young L H, Kahn R: Thiazolidinedione use, fluid retention, and congestive heart failure: a consensus statement from the American Heart Association and American Diabetes Association. Oct. 7, 2003. *Circulation* 108:2941-2948, 2003.
21. Wysowski D K, Armstrong G, Governale L: Rapid increase in the use of oral antidiabetic drugs in the United States, 1990-2001. *Diabetes Care* 26:1852-1855, 2003.
22. Lin B L, Wang H J, Wang J S, Zaharia L I, Abrams S R: Abscisic acid regulation of heterophylly in Marsilea quadrifolia L.: effects of R-(−) and S-(+) isomers. *J Exp Bot* 56:2935-2948, 2005.

23. Yin M, Bradford B U, Wheeler M D, Uesugi T, Froh M, Goyert S M, Thurman R G: Reduced early alcohol-induced liver injury in CD 14-deficient mice. *J Immunol* 166:4737-4742, 2001.
24. Hontecillas R, Wannemeulher M J, Zimmerman D R, Hutto D L, Wilson J H, Aim D U, Bassaganya-Riera J: Nutritional regulation of porcine bacterial-induced colitis by conjugated linoleic acid. *J Nutr* 132:2019-2027, 2002.
25. Bassaganya-Riera J, Pogranichniy R M, Jobgen S C, Halbur P G, Yoon K J, O'Shea M, Mohede I, Hontecillas R: Conjugated linoleic acid ameliorates viral infectivity in a pig model of virally induced immunosuppression. *J Nutr* 133:3204-3214, 2003.
26. Guan Y, Hao C, Cha D R, Rao R, Lu W, Kohan D E, Magnuson M A, Redha R, Zhang Y, Breyer M D: Thiazolidinediones expand body fluid volume through PPAR-gamma stimulation of ENaC-mediated renal salt absorption. *Nat Med* 11:861-866, 2005.
27. Desvergne B, Wahli W: Peroxisome proliferator-activated receptors: nuclear control of metabolism. *Endocr Rev* 20:649-688, 1999.
28. Nagy L, Tontonoz P, Alvarez J G, Chen H, Evans R M: Oxidized LDL regulates macrophage gene expression through ligand activation of PPARgamma. *Cell* 93:229-240, 1998.
29. McIntyre T M, Pontsler A V, Silva A R, St Hilaire A, Xu Y, Hinshaw J C, Zimmerman G A, Hama K, Aoki J, Arai H, Prestwich G D: Identification of an intracellular receptor for lysophosphatidic acid (LPA): LPA is a transcellular PPARgamma agonist. *Proc Natl Acad Sci USA* 100:131-136, 2003.
30. Ouchi N, Kihara S, Arita Y, Okamoto Y, Maeda K, Kuriyama H, Hotta K, Nishida M, Takahashi M, Muraguchi M, Ohmoto Y, Nakamura T, Yamashita S, Funahashi T, Matsuzawa Y: Adiponectin, an adipocyte-derived plasma protein, inhibits endothelial NF-kappaB signaling through a cAMP-dependent pathway. *Circulation* 102:1296-1301, 2000.
31. Berg A H, Combs T P, Du X, Brownlee M, Scherer P E: The adipocyte-secreted protein Acrp30 enhances hepatic insulin action. *Nat Med* 7:947-953, 2001.
32. Fruebis J, Tsao T S, Javorschi S, Ebbets-Reed D, Erickson M R, Yen F T, Bihain B E, Lodish H F: Proteolytic cleavage product of 30-kDa adipocyte complement-related protein increases fatty acid oxidation in muscle and causes weight loss in mice. *Proc Natl Acad Sci USA* 98:2005-2010, 2001.
33. Trayhum P, Wood I S: Adipokines: inflammation and the pleiotropic role of white adipose tissue. *Br J Nutr* 92:347-355, 2004.
34. Mudaliar S, Chang A R, Henry R R: Thiazolidinediones, peripheral edema, and type 2 diabetes: incidence, pathophysiology, and clinical implications. *Endocr Pract* 9:406-416, 2003.
35. Page R L, 2nd, Gozansky W S, Ruscin J M: Possible heart failure exacerbation associated with rosiglitazone: case report and literature review. *Pharmacotherapy* 23:945-954, 2003.
36. Tai T A, Jennermann C, Brown K K, Oliver B B, MacGinnitie M A, Wilkison W O, Brown H R, Lehmann J M, Kliewer S A, Morris D C, Graves R A: Activation of the nuclear receptor peroxisome proliferator-activated receptor gamma promotes brown adipocyte differentiation. *J Biol Chem* 271:29909-29914, 1996.
37. Watkins S M, Reifsnyder P R, Pan H J, German J B, Leiter E H: Lipid metabolome-wide effects of the PPARgamma agonist rosiglitazone. *J Lipid Res* 43: 1809-1817, 2002.
38. Xu A, Wang Y, Keshaw H, Xu L Y, Lam K S, Cooper G J: The fat-derived hormone adiponectin alleviates alcoholic and nonalcoholic fatty liver diseases in mice. *J Clin Invest* 112:91-100, 2003.
39. Gomez-Cadenas A, Tadeo F R, Talon M, Primo-Millo E: Leaf Abscission Induced by Ethylene in Water-Stressed Intact Seedlings of Cleopatra Mandarin Requires Previous Abscisic Acid Accumulation in Roots. *Plant Physioll* 12:401-408, 1996.
40. Gubler F, Millar A A, Jacobsen J V: Dormancy release, ABA and pre-harvest sprouting. *Curr Opin Plant Biol* 8: 183-187, 2005.
41. Goliber T E, Feldman L J: Osmotic stress, endogenous abscisic acid and the control of leaf morphology in *Hippuris vulgaris* L. *Plant Cell Environ* 12:163-171, 1989.
42. Finkelstein R R, Gibson S I: ABA and sugar interactions regulating development: crosstalk or voices in a crowd? *Curr Opin Plant Biol* 5:26-32, 2002.
43. Arenas-Huertero F, Arroyo A, Zhou L, Sheen J, Leon P: Analysis of *Arabidopsis* glucose insensitive mutants, gin5 and gin6, reveals a central role of the plant hormone ABA in the regulation of plant vegetative development by sugar. *Genes Dev* 14:2085-2096, 2000.
44. Le Hir R, Leduc N, Jeannette E, Viemont J D, Pelleschi-Travier S: Variations in sucrose and ABA concentrations are concomitant with heteroblastic leaf shape changes in a rhythmically growing species (Quercus robur). *Tree Physiol* 26:229-238, 2005.
45. Hill, R. D. et al., *Plant Physiol.* 108:573-579 (1995).
46. Loveys, B. R. and H. M. van Dijk (1988) Improved Extraction of ABA from Plant Tissue. Aust. J. Plant Physiol. 15: 421-427.
47. Zhou, R. et al (2004) A new abscisic acid catabolic pathway. Plant Physiol 134: 361-369.
48. Guri A J, Hontecillas R, Si H, Liu D, Bassaganya-Riera J. Dietary abscisic acid ameliorates glucose tolerance and obesity-related inflammation in db/db mice fed high-fat diets. Clin Nutr 2006; doi:10.1016/j.clnu.2006.07.008.
49. Akiyama T E, Sakai S, Lambert G, Nicol C J, Matsusue K, Pimprale S, Lee Y H, Ricote M, Glass C K, Brewer H B, Jr., Gonzalez F J. Conditional disruption of the peroxisome proliferator activated receptor gamma gene in mice results in lowered expression of ABCA1, ABCG1, and apoE in macrophages and reduced cholesterol efflux. Mol Cell Biol 2002; 22: 2607-19.
50. Bassaganya-Riera J, Reynolds K, Martino-Catt S, Cui Y, Hennighausen L, Gonzalez F, Rohrer J, Benninghoff A U, Hontecillas R. Activation of PPAR gamma and delta by conjugated linoleic acid mediates protection from experimental inflammatory bowel disease. Gastroenterology 2004; 127: 777-91.
51. Kutlu B, Darville M I, Cardozo A K, Eizirik D L. Molecular regulation of monocyte chemoattractant protein-1 expression in pancreatic beta-cells. Diabetes 2003; 52: 348-55.
52. Weisberg S P, Hunter D, Huber R, Lemieux J, Slaymaker S, Vaddi K, Charo I, Leibel R L, Ferrante A W, Jr. CCR2 modulates inflammatory and metabolic effects of high-fat feeding. J Clin Invest 2006; 116: 115-24.
53. Kanda H, Tateya S, Tamori Y, Kotani K, Hiasa K, Kitazawa R, Kitazawa S, Miyachi H, Maeda S, Egashira K, Kasuga M. MCP-1 contributes to macrophage infiltration into adipose tissue, insulin resistance, and hepatic steatosis in obesity. J Clin Invest 2006; 116: 1494-505.
54. Kamei N, To be K, Suzuki R, Ohsugi M, Watanabe T, Kubota N, Ohtsuka-Kowatari N, Kumagai K, Sakamoto K, Kobayashi M, Yamauchi T, Ueki K, Oishi Y, Nishimura S, Manabe I, Hashimoto H, Ohnishi Y, Ogata H, Tokuyama K, Tsunoda M, Ide T, Murakami K, Nagai R, Kadowaki T. Overexpression of monocyte chemoattractant protein-1 in adipose tissues causes macrophage recruitment and insulin resistance. J Biol Chem 2006; 281: 26602-14.
55. Mokdad A H, Bowman B A, Ford E S, Vinicor F, Marks J S, Koplan J P. The continuing epidemics of obesity and diabetes in the United States. Jama 2001; 286: 1195-200.
56. Amer P. Regional adipocity in man. J Endocrinol 1997; 155: 191-2; Holness M J, Bulmer K, Smith N D, Sugden M C. Investigation of potential mechanisms regulating protein expression of hepatic pyruvate dehydrogenase kinase isoforms 2 and 4 by fatty acids and thyroid hormone. Biochem J 2003; 369: 687-95; Boden G. Fatty acid-induced inflammation and insulin resistance in skeletal muscle and liver. Curr Diab Rep 2006; 6: 177-81.
57. Shoelson S E, Lee J, Goldfine A B. Inflammation and insulin resistance. J Clin Invest 2006; 116: 1793-801.
58. Lin H H, Faunce D E, Stacey M, Terajewicz A, Nakamura T, Zhang-Hoover J, Kerley M, Mucenski M L, Gordon S, Stein-Streilein J. The macrophage F4/80 receptor is required for the induction of antigen-specific efferent regulatory T cells in peripheral tolerance. J Exp Med 2005; 201: 1615-25.
59. Charriere G, Cousin B, Arnaud E, Andre M, Bacou F, Penicaud L, Casteilla L. Preadipocyte conversion to macrophage. Evidence of plasticity. J Biol Chem 2003; 278: 9850-5.
60. Nibbering P H, Leijh P C, van Furth R. Quantitative immunocytochemical characterization of mononuclear phagocytes. 1. Monoblasts, promonocytes, monocytes, and peritoneal and alveolar macrophages. Cell Immunol 1987; 105: 374-85.
61. Phillips R J, Lutz M, Premack B. Differential signaling mechanisms regulate expression of CC chemokine receptor-2 during monocyte maturation. J Inflamm (Lond) 2005; 2: 14.
62. Chen Y, Green S R, Ho J, Li A, Almazan F, Quehenberger O. The mouse CCR2 gene is regulated by two promoters that are responsive to plasma cholesterol and peroxisome proliferator-activated receptor gamma ligands. Biochem Biophys Res Commun 2005; 332: 188-93.
63. Tanaka T, Fukunaga Y, Itoh H, Doi K, Yamashita J, Chun T H, Inoue M, Masatsugu K, Saito T, Sawada N, Sakaguchi S, Arai H, Nakao K. Therapeutic potential of thiazolidinediones in activation of peroxisome proliferator-activated receptor gamma for monocyte recruitment and endothelial regeneration. Eur J Pharmacol 2005; 508: 255-65.
64. Tsuchida A, Yamauchi T, Takekawa S, Hada Y, Ito Y, Maki T, Kadowaki T. Peroxisome proliferator-activated receptor (PPAR)alpha activation increases adiponectin receptors and reduces obesity-related inflammation in adipose tissue: comparison of activation of PPAR alpha, PPAR gamma, and their combination. Diabetes 2005; 54: 3358-70.
65. He W, Barak Y, Hevener A, Olson P, Liao D, Le J, Nelson M, Ong E, Olefsky J M, Evans R M. Adipose-specific peroxisome proliferator-activated receptor gamma knockout causes insulin resistance in fat and liver but not in muscle. Proc Natl Acad Sci USA 2003; 100: 15712-7.
66. Hanauer S B. Inflammatory bowel disease: epidemiology, pathogenesis, and therapeutic opportunities. Inflamm Bowel Dis 2006; 12 Suppl 1:S3-9.
67. Hanauer S B, Present D H. The state of the art in the management of inflammatory bowel disease. Rev Gastroenterol Disord 2003; 3:81-92.
68. Mackner L M, Sisson D P, Crandall W V. Review: psychosocial issues in pediatric inflammatory bowel disease. J Pediatr Psychol 2004; 29:243-57.
69. Odegaard J I, Ricardo-Gonzalez R R, Goforth M H, et al. Macrophage-specific PPARgamma controls alternative activation and improves insulin resistance. Nature 2007; 447:1116-20.
70. Guri A J, Hontecillas R, Si H, Liu D, Bassaganya-Riera J. Dietary abscisic acid ameliorates glucose tolerance and obesity-related inflammation in db/db mice fed high-fat diets. Clin Nutr 2007; 26:107-16.
71. Guri A J, Hontecillas R, Ferrer G, et al. Loss of PPAR gamma in immune cells impairs the ability of abscisic acid to improve insulin sensitivity by suppressing monocyte chemoattractant protein-1 expression and macrophage infiltration into white adipose tissue. J Nutr Biochem 2008; 19:216-28.
72. Guri A J, Misyak S, Hontecillas R, et al. Abscisic acid ameliorates atherosclerosis by suppressing macrophage and CD4+ T cell recruitment into the aortic wall. Journal of Nutritional Biochemistry 2009; In Press.
73. Bruzzone S, Bodrato N, Usai C, et al. Abscisic acid is an endogenous stimulator of insulin release from human pancreatic islets with cyclic ADP ribose as second messenger. J Biol Chem 2008; 283:32188-97.
74. Magnone M, Bruzzone S, Guida L, et al. Abscisic acid released by human monocytes activates monocytes and vascular smooth muscle cell responses involved in atherogenesis. J Biol Chem 2009.
75. Marder B A, Schroppel B, Lin M, et al. The impact of costimulatory molecule gene polymorphisms on clinical outcomes in liver transplantation. Am J Transplant 2003; 3:424-31.
76. Garg P, Vijay-Kumar M, Wang L, Gewirtz A T, Merlin D, Sitaraman S V. Matrix metalloproteinase-9-mediated tissue injury overrides the protective effect of matrix metalloproteinase-2 during colitis. Am J Physiol Gastrointest Liver Physiol 2009; 296:G 175-84.
77. Bassaganya-Riera J, Misyak S, Guri A J, Hontecillas R. PPAR gamma is highly expressed in F4/80(hi) adipose tissue macrophages and dampens adipose-tissue inflammation. Cell Immunol 2009; 258:138-146.
78. Luo Y, Xia B, Li C, et al. Cytotoxic T lymphocyte antigen-4 promoter-658CT gene polymorphism is associated with ulcerative colitis in Chinese patients. Int J Colorectal Dis 2009; 24:489-93.
79. Soedamah-Muthu S S, Chaturvedi N, Schalkwijk C G, Stehouwer C D, Ebeling P, Fuller J H. Soluble vascular cell adhesion molecule-1 and soluble E-selectin are associated with micro- and macrovascular complications in Type 1 diabetic patients. J Diabetes Complications 2006; 20:188-95.
80. Klimiuk P A, Sierakowski S, Domyslawska I, Chwiecko J. Effect of etanercept on serum levels of soluble cell adhesion molecules (sICAM-1, sVCAM-1, and sE-selectin) and vascular endothelial growth factor in patients with rheumatoid arthritis. Scand J Rheumatol 2009; 38:439-44.
81. Nowak M, Wielkoszynski T, Marek B, et al. Blood serum levels of vascular cell adhesion molecule (sVCAM-1), intercellular adhesion molecule (sICAM-1) and endothelial leucocyte adhesion molecule-1 (ELAM-1) in diabetic retinopathy. Clin Exp Med 2008; 8:159-64.
82. Kuryliszyn-Moskal A, Klimiuk P A, Sierakowski S. [Serum soluble adhesion molecules—sICAM-1, sVCAM-1, sE-selectin—in patients with systemic rheumatoid arthritis]. Pol Merkur Lekarski 2004; 17:353-6.
83. Douroudis K, Laine A P, Heinonen M, et al. Association of CTLA4 but not ICOS polymorphisms with type 1 diabetes in two populations with different disease rates. Hum Immunol 2009; 70:536-9.
84. Sakthivel P. Bench to bedside of CTLA-4: a novel immuno-therapeutic agent for inflammatory disorders. Recent Pat Inflamm Allergy Drug Discov 2009; 3:84-95.

85. Song G, Zhao X, Xu J, Song H. Increased expression of intercellular adhesion molecule-1 and vascular cell adhesion molecule-1 in rat cardiac allografts. Transplant Proc 2008; 40:2720-3.
86. Kamoun M. Cellular and molecular parameters in human renal allograft rejection. Clin Biochem 2001; 34:29-34.
87. Dedrick R L, Bodary S, Garovoy M R. Adhesion molecules as therapeutic targets for autoimmune diseases and transplant rejection. Expert Opin Biol Ther 2003; 3:85-95.
88. Perkins J D. The influence of CTLA-4 gene polymorphisms on liver transplant outcomes. Liver Transpl 2006; 12:1552-3.

What is claimed is:

1. A method for treating inflammatory bowel disease in a mammal, the method comprising administering to the mammal a composition comprising:

a substantially pure preparation of one or more compounds selected from: abscisic acid (ABA) in its free acid form and pharmaceutically suitable salts thereof, in amounts that are sufficient to alter the expression or activity of PPAR γ in a cell of the mammal.

2. The method of claim 1, wherein the composition further comprises a carrier that has substantially no effect on the expression or activity of PPAR γ in a cell of the mammal.

3. The method of claim 2, wherein the carrier is a pharmaceutical carrier.

4. The method of claim 2, wherein the carrier is a nutritional supplement, functional food, or dietary aid.

5. The method of claim 1, wherein the purity of the substantially pure preparation is greater than about 95%.

6. The method of claim 1, wherein the one or more compounds is abscisic acid in its free acid form.

7. The method of claim 1, wherein the abcisic acid in its free acid form is chemically synthesized.

8. The method of claim 1, wherein the amount that is sufficient to alter the expression or activity of PPAR γ in a cell of the mammal is between about 1 mg/day and about 5,000 mg/day.

* * * * *

UNITED STATES PATENT AND TRADEMARK OFFICE
CERTIFICATE OF CORRECTION

PATENT NO. : 8,367,727 B2
APPLICATION NO. : 12/712899
DATED : February 5, 2013
INVENTOR(S) : Josep Bassaganya-Biera et al.

It is certified that error appears in the above-identified patent and that said Letters Patent is hereby corrected as shown below:

In the specification

Column 1, line 13-14 after the Title please add the following:

--STATEMENT OF GOVERNMENT INTEREST

This invention was made with government support under Grant No. AT004308 awarded by the National Institutes of Health. The government has certain rights in the invention.--

Signed and Sealed this
Thirteenth Day of October, 2015

Michelle K. Lee
*Director of the United States Patent and Trademark Office*